US010617735B2

(12) United States Patent
Vavvas et al.

(10) Patent No.: US 10,617,735 B2
(45) Date of Patent: *Apr. 14, 2020

(54) METHODS AND COMPOSITIONS FOR PRESERVING RETINAL GANGLION CELLS

(71) Applicant: Massachusetts Eye and Ear Infirmary, Boston, MA (US)

(72) Inventors: Demetrios G. Vavvas, Boston, MA (US); Joan W. Miller, Winchester, MA (US); Maki Kayama, Tokyo (JP)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/956,133

(22) Filed: Apr. 18, 2018

(65) Prior Publication Data
US 2019/0099467 A1 Apr. 4, 2019

Related U.S. Application Data

(63) Continuation of application No. 15/093,480, filed on Apr. 7, 2016, now Pat. No. 9,993,517, which is a continuation of application No. 13/882,932, filed as application No. PCT/US2011/057327 on Oct. 21, 2011, now abandoned.

(60) Provisional application No. 61/472,144, filed on Apr. 5, 2011, provisional application No. 61/414,862, filed on Nov. 17, 2010, provisional application No. 61/409,055, filed on Nov. 1, 2010.

(51) Int. Cl.
| | |
|---|---|
| *A61K 31/40* | (2006.01) |
| *A61K 31/4178* | (2006.01) |
| *A61K 38/00* | (2006.01) |
| *A61K 38/05* | (2006.01) |
| *A61K 38/55* | (2006.01) |
| *A61K 38/06* | (2006.01) |
| *A61K 31/195* | (2006.01) |
| *A61K 31/403* | (2006.01) |
| *A61K 31/4166* | (2006.01) |
| *A61K 9/00* | (2006.01) |

(52) U.S. Cl.
CPC ............ *A61K 38/06* (2013.01); *A61K 9/0048* (2013.01); *A61K 31/195* (2013.01); *A61K 31/40* (2013.01); *A61K 31/403* (2013.01); *A61K 31/4166* (2013.01); *A61K 31/4178* (2013.01); *A61K 38/005* (2013.01)

(58) Field of Classification Search
None
See application file for complete search history.

(56) References Cited

U.S. PATENT DOCUMENTS

| | | |
|---|---|---|
| 5,443,505 A | 8/1995 | Wong et al. |
| 5,766,242 A | 6/1998 | Wong et al. |
| 6,245,523 B1 | 6/2001 | Altieri |
| 6,251,090 B1 | 6/2001 | Avery et al. |
| 6,299,895 B1 | 10/2001 | Hammang et al. |
| 6,375,972 B1 | 4/2002 | Guo et al. |
| 6,413,540 B1 | 7/2002 | Yaacobi |
| 6,416,777 B1 | 7/2002 | Yaacobi |
| 7,622,106 B1 | 11/2009 | Wang et al. |
| 9,492,432 B2 | 11/2016 | Vavvas et al. |
| 9,993,517 B2 | 6/2018 | Vavvas et al. |
| 10,022,419 B2 | 7/2018 | Vavvas et al. |
| 10,149,884 B2 | 12/2018 | Vavvas et al. |
| 2003/0103945 A1 | 6/2003 | Chen et al. |
| 2007/0049565 A1 | 3/2007 | Gwag et al. |
| 2007/0298129 A1 | 12/2007 | Gwag et al. |
| 2009/0099242 A1 | 4/2009 | Cuny et al. |
| 2009/0220570 A1 | 9/2009 | He et al. |
| 2011/0071088 A1 | 3/2011 | Benowitz |
| 2013/0137642 A1 | 5/2013 | Vavvas et al. |
| 2014/0024598 A1 | 1/2014 | Vavvas et al. |
| 2014/0357570 A1 | 12/2014 | Vavvas |
| 2016/0151442 A1 | 6/2016 | Vavvas |
| 2016/0250189 A1 | 9/2016 | Vavvas et al. |
| 2016/0367619 A1 | 12/2016 | Vavvas et al. |
| 2017/0216393 A1 | 8/2017 | Vavvas et al. |
| 2019/0117724 A1 | 4/2019 | Vavvas et al. |
| 2019/0216881 A1 | 7/2019 | Vavvas et al. |

FOREIGN PATENT DOCUMENTS

| | | |
|---|---|---|
| WO | WO-2000/040089 A1 | 7/2000 |
| WO | WO-2001/028474 A1 | 4/2001 |
| WO | WO-2001/028493 A2 | 4/2001 |

(Continued)

OTHER PUBLICATIONS

Ambati et al., (2000), 'Diffusion of High Molecular Weight Compounds through Sclera,' Invest Ophthamol Vis Sci, 41(5):1181-5.
Ambati et al., (2000), 'Transscleral Delivery of Bioactive Protein to the Choroid and Retina,' Invest Opthalmol Vis Sci, 41(4):1186-91.
Arimura et al., (2009) 'Intraocular Expression and Release of High-Mobility Group Box 1 Protein in Retinal Detachment,' Lab Invest, 89(3):278-89.
Arroyo et al., (2005), 'Photoreceptor Apoptosis in Human Retinal Detachment,' Am J Opthalmol,139(4):605-10.

(Continued)

*Primary Examiner* — Christine J Saoud
*Assistant Examiner* — Jon M Lockard
(74) *Attorney, Agent, or Firm* — Goodwin Procter LLP

(57) ABSTRACT

Provided are methods and compositions for maintaining the viability of retinal ganglion cells in a subject with an ocular disorder including, for example, glaucoma and optic nerve injury. The viability of the retinal ganglion cells can be preserved by administering a necrosis inhibitor either alone or in combination with an apoptosis inhibitor to a subject having an eye with the ocular condition. The compositions, when administered, maintain the viability of the cells and/or promote axon regeneration, thereby minimizing the loss of vision or visual function associated with the ocular disorder.

30 Claims, 27 Drawing Sheets

Specification includes a Sequence Listing.

(56) References Cited

FOREIGN PATENT DOCUMENTS

| WO | WO-2001/039792 A2 | 6/2001 |
|---|---|---|
| WO | WO-2002/089767 | 11/2002 |
| WO | WO-2003/061519 | 7/2003 |
| WO | WO-2005/077344 A2 | 8/2005 |
| WO | WO-2007/071448 A2 | 6/2007 |
| WO | WO-2007/075772 A2 | 7/2007 |
| WO | WO-2008/045406 A2 | 4/2008 |
| WO | WO-2009/023272 A1 | 2/2009 |
| WO | WO-2010/022140 A1 | 2/2010 |
| WO | WO-2010/075290 A1 | 7/2010 |
| WO | WO-2011/071088 A1 | 6/2011 |
| WO | WO-2011/133964 A2 | 10/2011 |
| WO | WO-2012/061045 A2 | 5/2012 |
| WO | WO-2013/059791 A2 | 4/2013 |

OTHER PUBLICATIONS

Balkwill, (2009) 'Tumor Necrosis Factor and Cancer,' Nat Rev Cancer, 9(5):361-71.
Barber et al., (1998), 'Neural Apoptosis in the Retina During Experimental and Human Diabetes, Early Onset and Effect of Insulin' J Clin Invest, 102(4):783-91.
Beattie, et al. (2000) "Review of Current Evidence for Apoptosis after Spinal Cord Injury," Journal of Neurotrauma, 17(10): 915-925.
Campo et al., (1999), 'Pars Plana Vitrectomy Without Scleral Buckle for Pseudophakic Retinal Detachments,' Ophthalmology, 106(9):1811-5.
Candé et al., (2004) 'Apoptosis-Inducing Factor (AIF): Caspase-Independent After All,' Cell Death Differ, 11(6):591-5.
Cavassani et al., (2008) 'TLR3 is an Endogenous Sensor of Tissue Necrosis During Acute Inflammatory Events,' J Exp Med, 205(11):2609-21.
Chan, et al., (2011) "Rescue of Cybids Containing Leber Hereditary Optic Neuropathy (Ihon) Mutation Using Necrostatin-1 and Pancaspase Inhibitor Combination," Annual Meeting of the Association-for-Research-in-Vision-and-Ophthalmology (ARVO), May 1, 2011, (ABSTRACT).
Chang et al., (2002), 'Retinal Degeneration Mutants in the Mouse,' Vis Res, 42(4):517-25.
Chaudhary et al., (1999), 'Caspase Inhibitors Block the Retinal Ganglion Cell Death Following Optic Nerve Transection,' Mol Brain Res, 67(1):36-45.
Chauvier (2007), 'Broad-Spectrum Caspase Inhibitors: From Myth to Reality?,' Cell Death Differ, 14(2),387-91.
Cho et al., (2009), 'Phosphorylation-Driven Assembly of the RIP1-RIP3 Complex Regulates Programmed Necrosis and Virus-Induced Inflammation,' Cell, 137(6):1112-23.
Chua et al., (2006) 'Necrostatin-1 is a Novel Protector of Myocardial Infarction,' 79th Annual Scientific Session of the American Heart Association, Chicago, IL, 114(18):212. (Abstract).
Chua et al., (2010), 'Neuroprotective Agents in Glaucoma Therapy: Recent Developments and Future Directions,' Exp Rev Ophthalmol, 5(5):627-36.
Cook et al., (1995), 'Apoptotic Photoreceptor Degeneration in Experimental Retinal Detachment,' Invest Ophthamol Vis Sci, 36(6):990-6.
Cuervo and Dice, (1996) 'A Receptor for the Selective Uptake and Degradation of Proteins by Lysosomes,' Science, 273(5274):501-3.
Cui et al., (1999), 'CNTF, not Other Trophic Factors, Promotes Axonal Regeneration of Axotomized Retinal Ganglion Cells in Adult Hamsters,' Invest Ophthalmol Vis Sci, 40(3):760-6.
Cuny et al., (2008), 'Necroptosis-A Novel Cell Death Mechanism,' Drugs Future, 33(3):225-33.
Côté, et al. (2011) "Peripheral Nerve Grafts Support Regeneration after Spinal Cord Injury," The Journal of the American Society for Experimental Neuro Therapeutics, 8:294-303.
D'Onofrio et al., (2011), 'Involvement of Caspase-6 and Caspase-8 in Neuronal Apoptosis and the Regenerative Failure of Injured Retinal Ganglion Cells,' Invest Ophthalmol Vis Sci, 52(14):5448 (Abstract).

Degterev et al., (2005) 'Chemical Inhibitor of Nonapoptotic Cell Death with Therapeutic Potential for Ischemic Brain Injury,' Nat Chem Biol, 1(2):112-9.
Degterev et al., (2008) 'Identification of RIP1 Kinase as a Specific Cellular Target of Necrostatins,' Nat Chem Biol, 4(5):313-21.
Deveraux et al., (1998) 'IAPs Block Apoptotic Events Induces by Capase-8 and Cytochrome C by Direct Inhibition of Distinct Caspases,' EMBO J, 17(8):2215-23.
Dice (2007), 'Chaperone-Mediated Autophagy,' Autophagy, 3(4):295-9.
Donovan and Cotter, (2009) 'Caspase-Independent Photoreceptor Apoptosis in vivo and Differential Expression of Apoptotic Protease Activating Factor-1 and Caspase-3 During Retinal Development,' Cell Death Differ, 9(11):1220-31.
Dreyer et al., (1996) 'Elevated Glutamate Levels in the Vitreous Body of Humans and Monkeys with Glaucoma,' Arch Ophthalmol, 114(3):299-305.
Duan et al., (2015), 'Subtype-Specific Regeneration of Retinal Ganglion Cells Following Axotomy: Effects of Osteopontin and mTOR Signaling,' Neuron, 85(6):1244-56.
Dunaief et al., (2002) 'The Role of Apoptosis in Age-Related Macular Degeneration,' Arch Ophthalmol, 120(11):1435-42.
Ekert et al., (1999) 'Caspase Inhibitors,' Cell Death Differ, 6(11):1081-6.
Erickson et al., (1983) 'Retinal Detchment in the Cat: The Outer Nuclear and Outer Plexiform Layers,' Invest Ophthalmol Vis Sci, 24(7):927-42.
Festjens et al., (2006) 'Necrosis, a Well-Orchestrated Form of Cell Demise: Signalling Cascades, Important Mediators and Concomitant Immune Response,' Biochim Biophys Acta, 1757(9-10):1371-87.
Festjens et al., (2007), 'RIP1, A Kinase on the Crossroads of a Cell's Decision to Live or Die,' Cell Death Differ, 14(3):400-10.
Finn et al., (2000), 'Evidence that Wallerian Degeneration and Localized Axon Degeneration Induced by Local Neurotrophin Deprivation do not Involve Caspases,' J Neurosci, 20(4):1333-41.
Fulton et al., (2001), 'The Rod Photoreceptors in Retinopathy of Prematurity, An Electroretinographic Study,' Arch Ophthalmol, 119(4):499-505.
Galluzzi and Kroemer, (2008), 'Necroptosis: A Specialized Pathway of Programmed Necrosis,' Cell, 135(7):1161-3.
Galluzzi et al., (2009), 'RIP Kinases Initiate Programmed Necrosis,' J Mol Cell Biol, 1(1):8-10.
Gerth et al., (2008) "Retinal morphology in patients with BBS1 and BBS10 Related Bardet-Biedl Syndrome evaluated by Fourier-domain optical coherence tomography", Vision Research, 48:392-399.
Golstein and Kroemer, (2006), 'Cell Death by Necrosis: Towards a Molecular Definition,' Trends Biochem Sci, 32(1):37-43.
Grasl-Kraupp et al., (1995) "In Situ Detection of Fragmented DNA (TUNEL Assay) Fails to Discriminate Among Apoptosis, Necrosis, and Autolytic Cell Death: A Cautionary Note," Hepatology, 21(5):1465-8.
Hagimura et al., (2002), 'Persistent Foveal Retinal Detachment After Successful Rhegmatogenous Retinal Detachment Surgery,' Am J Ophthalmol, 133(4):516-20.
He et al., (2009), 'Receptor Interacting Protein Kinase-3 Determines Cellular Necrotic Response to TNF-$\alpha$,' Cell, 137(6):1100-11.
Hisatomi et al., (2001), 'Relocalization of Apoptosis-Inducing Factor in Photoreceptor Apoptosis Induced by Retinal Detachment In Vivo,' Am J Pathol, 158(4):1271-8.
Hisatomi, et al. (2003) "Elimination of Apoptotic Debris into the Subretinal Space and Macrophage-Mediated Phagocytosis via Phosphatidylserine Receptor and Integrin $\alpha v\beta 3$," American Journal of Pathology, 162:1869-1879.
Histatomi et al., (2008), 'HIV Protease Inhibitors Provide Neuroprotection Through Inhibition of Mitochondrial Apoptosis in Mice,' J Clin Invest, 118(6):2025-8.
Hoglen et al., (2004), 'Characterization of IDN-6556 (3-{2-(2-tert-Butyl-Phenylaminooxalyl)-Amino]-Propionylamino}-4-oxo-5-(2,3,5,6-Tetrafluoro-Phenoxy-Pentanoic Acid): A Liver-Targeted Caspase Inhibitor,' J Pharmacol Exp Therapeut, 309(2):634-40.

(56) References Cited

OTHER PUBLICATIONS

Holler et al., (2000), 'Fas Triggers an Alternative, Caspase-8-Independent Cell Death Pathway Using the Kinase RIP as Effector Molecule,' Nat Immunol, 1(6):489-95.
Hu et al., (2012), 'Differential Effects of Unfolded Protein Response Pathways on Axon Injury-Induced Death of Ganglion Cells,' Neuron, 73(3):445-52.
Ichimura et al., (2000), 'A Ubiquitin-Like System Mediates Protein Lipidation,' Nature, 408(6811):488-92.
International Search Report and Written Opinion for PCT/US2011/033704, dated Jun. 22, 2012, (14 pages).
International Search Report and Written Opinion for PCT/US2011/057327, dated May 21, 2013, (15 pages).
International Search Report and Written Opinion for PCT/US2012/061324 dated May 16, 2013 (17 pages).
Jones (2005), 'Neurodegenerative Disorders: Blocking a Path to Cell Death,' [online], retrieved on Mar. 12, 2015 from <22.signaling-gateway.org/Update/Updates/200508/nrn1732.html> (2 pages).
Kabeya et al., (2000), 'LC3, a Mammalian Homologue of Yeast Apg8p, is Localized in Autophagosome Membrances After Processing,' EMBO, 19(21):5720-8.
Kaiser et al., (2008), 'Receptor-Interacting Protein Homotypic Interaction Motif-Dependent Control of NF-β Activation via the DNA-Dependent Activator of IFN Regulatory Factors,' J Immunol, 181(9):6427-34.
Karl, et al. (2008) "Stimulation of Neural Regeneration in the Mouse Retina," Proc. Natl. Acad. Sci. U.S.A. 105(49):19508-13.
Kayama et al., (2010), 'Transfection with pax6 Gene of Mouse Embryonic Stem Cells and Subsequent Cell Cloning Induced Retinal Neuron Progenitors, including Retinal Ganglion Cell-Like Cells, In Vitro,' Opthal Res, 43(2):79-91.
Kelliher et al., (1998), 'The Death Domain Kinase RIP Mediates the TNF-Induced NF-κβ Signal,' Immunity, 8(3):297-303.
Kermer et al., (1998). 'Inhibition of CPP32-Like Proteases Rescues Axotomized Retinal Ganglion Cells from Secondary Cell Death in vivo,' J Neurosci, 18(12):4656-62.
Kermer et al., (2000), 'Caspase-9: Involvement in Secondary Death of Axotomized Rat Retinal Ganglion Cells In Vivo,' Mol Brain Res, 85(1-2):144-50.
Kerrigan et al., (1997), 'TUNEL-Positive Ganglion Cells in Human Primary Open-Angle Glaucoma,' Arch Ophthalmol, 115(8):1031-5.
Kim et al., (2007), 'TNF-Induced Activation of the Nox1 NADPH Oxidase and Its Role in the Induction of Necrotic Cell Death,' Mol Cell, 26(5):675-87.
Knöferle et al., (2010), 'Mechanisms of Acute Axonal Degeneration in the Optic Nerve in vivo,' Proc Natl Acad Sci USA., 107(13):6064-9.
Kong J et al., (2009), 'Rescue of Motor Neurons in ALS by Targeting the BNIP3 Cell Death Pathway,' Abstract P25, 20th International Symposium on ALS/MND, *Amyotrophic Lateral Sclerosis,* (Supp 1):10:78-9.
Kourtis and Tavernarakis, (2009) 'Autophagy and Cell Death in Model Organisms,' Cell Death Differ, 16(1):21-30.
Krantic et al., (2007), 'Apoptosis-Inducing Factor: A Matter of Neuron Life and Death,' Prog Neurobiol, 81(3):179-6.
Kroemer et al., (2009), Classification of Cell Death: Recommendations of the Nomenclature Committee on Cell Death 2009, Cell Death Differ, 16(1):3-11.
Kubay et al., (2005), 'Retinal Detachment Neuropathology and Potential Strategies for Neuroprotection,' Surv Opthalmol, 50(5):463-75.
Lee et al., (2004), 'The Kinase Activity of Rip1 is Not Required for Tumor Necrosis Factor-α-Induced Iκβ Kinase or p38 MAP Kinase Activation or for the Ubiquitination of Rip1 by Traf2,' The J Biol Chem, 279(32):33185-91.
Leon et al., (2000), 'Lens Injury Stimulates Axon Regeneration in the Mature Rat Optic Nerve,' J Neurosci, 20(12):4615-26.
Levine and Klionsky, (2004), 'Development by Self-Digestion: Molecular Mechanisms and Biological Functions of Autophagy,' Dev Cell, 6(4):463-77.
Levine et al., (2005) 'Autophagy in Cell Death: An Innocent Convict?,' J Clin Invest, 115(10):2679-88.
Levkovitch-Verbin, (2004), 'Animal Models of Optic Nerve Disease,' Eye (Lond), 18(11):1066-74.
Li et al., (2006), 'Ubiquitination of RIP is Required for Tumor Necrosis Factor α-Induced NF-κβActivation,' J Biol Chem, 281(19):13636-43.
Libby et al., (2005), 'Susceptibility to Neurodegeneration in a Glaucoma is Modified by Bax Gene Dosage,' PLoS Genet, 1(1):0017-0026.
Lin et al., (1999), 'Cleavage of the Death Domain Kinase RIP by Caspase-8 Prompts TNF-induced Apoptosis,' Genes Dev, 13(19):2514-26.
Lin et al., (2004), 'Tumor Necrosis Factor-Induced Nonapoptotic Cell Death Requires Receptor-Interacting Protein-Mediated Cellular Reactive Oxygen Species Accumulation,' J Biol Chem, 279(11):10822-8.
Linton, (2005) 'Caspase Inhibitors: A Pharmaceutical Industry Perspective,' Curr Top Med Chem, 5(16):1697-717.
Mahoney et al., (2008), Both cIAP1 and cIAP2 Regulate TNFα-Mediated NF-κβ Activation, Proc Natl Acad Sci USA.,105(33):11778-83.
Mann et al., (1948) 'The Perception of the Vertical: I. Visual and Non-Labyrinthine Cues,' Investigation conducted jointly with the School of Aviation Medicine and Research with the Office of Naval Research, J Exp Psych, 39(4):538-47.
Merfeld, (2011) 'Signal Detection Theory and Vestibular Thresholds: I. Basic Theory and Practical Considerations,' Exp Brain Res, 210(3-4):389-405.
Miyoshi T, (2005), 'Recovery of Central Nerve Function in View of Regeneration of Optic Nerve Function', Molecular Cerebrovascular Medicine, 4(1):32-7.
Moubarak et al., (2007), 'Sequential Activation of Poly(ADP-Ribose) Polymerase 1, Calpains, and Bax is Essential in Apoptosis-Inducing Factor-Mediated Programmed Necrosis,' Mol Cell Biol, 27(13):4844-62.
Murakami et al., (2008), Cell Injury, Repair, Aging and Apoptosis, Inhibition of Nuclear Translocation of Apoptosis-Inducing Factor is an Essential Mechanism of the Neuroprotective Activity of Pigment Epithelium-Derived Factor in a Rat Model of Retinal Degeneration, Am J Pathol, 173(5):1326-38.
Murakami et al., (2010), 'Receptor Interacting Protein 1 Kinase is an Essential Mediator of Programmed Photoreceptor Necrosis After Retinal Detachment,' Association for Research in Vision and Ophthalmology (ARVO) 2010 Annual Meeting, Ft. Lauderdal, FL May 2-6, 2010, Program #/Poster #:4034/A427, (2 pages) (Abstract available online Apr. 23, 2010).
Murakami et al., (2011), 'RIP Kinase-Mediated Necrosis as an Alternative Mechanism of Photoreceptor Death,' Oncotarget, 2(6):497-509.
Nakazawa et al., (2006), 'Characterization of Cytokine Responses to Retinal Detachment in Rats,' Mol Vis, 12:867-78.
Nakazawa et al., (2006), 'Tumor Necrosis Factor-α Mediates Oligodendrocyte Death and Delayed Retinal Ganglion Cell Loss in a Mouse Model of Glaucoma,' J Neurosci, 26(49):12633-41.
Nakazawa et al., (2007), 'Monocyte Chemoattractant Protein 1 Mediates Retinal Detachment-Induced Photoreceptor Apoptosis,' Proc Natl Acad Sci USA., 104(7):2425-30.
Newton et al., (2004), 'Kinase RIP3 Is Dispensable for Normal NF-κβs, Signaling by the B-Cell and T-Cell Receptors, Tumor Necrosis Factor Receptor 1, and Toll-Like Receptors 2 and 4,' Mol Cell Biol, 24(4):1464-9.
Norsworthy et al., (2017), '*Sox11* Expression Promotes Regeneration of Some Retinal Ganglion Cell Types but Kills Others,' Neuron, 94(6):1112-20.
Papapetropoulos et al., (2000), 'Angiopoietin-1 Inhibits Endothelial Cell Apoptosis via the Akt/Survivin Pathway' J Biol Chem, 275(13):9102-5.
Park et al., (2009), 'Cytokine-Induced SOCS Expression is Inhibited by cAMP Analogue: Impact on Regeneration in Injured Retina,' Mol Cell Neurosci, 41(3):313-24.

(56) References Cited

OTHER PUBLICATIONS

Rosenbaum et al., (2009), 'Necroptosis, a Novel Form of Caspase-Independent Cell Death, Contributes to Neuronal Damage in a Retinal Ischemia-Reperfusion Injury Model,' J Neurosci Res, 88(7):1569-76.
Saggu et al., (2010), Wallerian-like Axonal Degeneration in the Optic Nerve After Excitotoxic Retinal Insult: An Ultrastructural Study, BMC Neurosci, 11:97 (14 pages).
Sanges et al., (2006), 'Apoptosis in Retinal Degeneration Involves Cross-Talk Between Apoptosis-Inducing Factor (AIF) and Caspase-12 and is Blocked by Calpain Inhibitors,' Proc Natl Acad Sci USA, 103(46):17366-71.
Scaffidi et al., (2002) 'Release of Chromatin Protein HMGB1 by Necrotic Cells Triggers Inflammation,' Nature, 418(6894):191-5.
Schwartz (2004) "Optic Nerve Crush: Protection and Regeneration," Brain Research Bulletin, 62:467-471.
Seglen and Gordon, (1982) '3-Methyladenine: Specific Inhibitor of Autophagic/Lysosomal Protein Degradation in Isolated Rat Hepatocytes,' Proc Natl Acad Sci USA, 79(6):1889-92.
Sintzel et al., (1996), 'Biomaterials in Ophthalmic Drug Delivery,' Eur J Pharmaceut Biopharmaceut, 42(6):358-74.
Susin et al., (1999), 'Molecular Characterization of Mitochondrial Apoptosis-Inducing Factor,' Nature, 397(6718):441-6.
Tatton et al., (2001), 'Maintaining Mitochondrial Membrane Impermeability: An Opportunity for New Therapy in Glaucoma?,' Surv Ophthalmol, 45(3):S277-83.
Teng et al., (2007),'Structure-Activity Relationship Study of [1,2,3] Thiadiazole Necroptosis Inhibitors,' Bioorg Med Chem Lett, 17(24):6836-40.
Teng et al., (2008), 'Structure-Activity Relationship and Liver Microsome Stability Studies of Pyrrole Necroptosis Inhibitors,' Bioorg Med Chem Lett, 18(11):3219-23.
Tezel et al., (2001), 'TNF-$\alpha$ and TNF-$\alpha$ Receptor-1 in the Retina of Normal and Glaucomatous Eyes,' Invest Ophthalmol Vis Sci, 42(8):1787-94.
Trichonas et al., (2009), 'Identification of Necroptosis as a Mechanism of Photoreceptor Damage After Retinal Detachment and Nec-1 as a Potential Treatment,' Invest Ophthalmol Vis Sci, 50(13):5187 (e-Abstract) (2 pages) (Abstract).
Trichonas et al., (2010), 'Receptor Interacting Protein Kinases Mediate Retinal Detachment-Induced Photoreceptor Necrosis and Compensate for Inhibition of Apoptosis,' Proc Natl Acad Sci USA, 107(50):21695-700.
Tuo et al., (2007), 'Murine Ccl2/Cx3cr1 Deficiency Results in Retinal Lesions Mimicking Human Age-Related Macular Degeneration,' Invest Ophthalmol Vis Sci, 48(8):3827-36.
Vandenabeele et al., (2010), 'The Role of the Kinases RIP1 and RIP3 in TNF-Induced Necrosis,' Sci Signal, 3(115):re4.
Vanlangenakker et al., (2011), 'cIAP1 and TAK1 Protect Cells from TNF-Induced Necrosis by Preventing RIP1/RIP3-Dependent Reactive Oxygen Species Production,' Cell Death Differ,18(4):656-65.
Vavvas et al., (2008), 'Identification of Necroptosis as a Mechanism of Photoreceptor Damage after Retinal Detachment and Nec-1 as a Potential Treatment,' 41st Annual Meeting of the Retina Society, Sep. 25-28, 2008, Scottsdate, AZ (1 page) (Abstract first available online Jun. 1, 2008).
Vercammen et al., (1998), 'Dual Signaling of the Fas Receptor: Initiation of Both Apoptotic and Necrotic Cell Death Pathways,' J Exp Med, 188(5):919-30.
Wang et al., (2008), 'TNF-$\alpha$ Induces Two Distinct Caspase-8 Activation Pathways,' Cell, 133(4):693-703.
Xu et al., (2010), 'Synergistic Protective Effects of Humanin and Necrostatin-1 on Hypoxia and Ischemia/Reperfusion Injury,' Brain Res, 1355:189-94 (NIH Public Access author manuscript) (10 pages).
Yan et al., (2000), 'Matrix Metalloproteinases and Tumor Necrosis Factor-$\alpha$ in Glaucomatous Optic Nerve Head,' Arch Ophthalmol, 118(5):666-73.
Yang et al., (2008), 'Toll-Like Receptor 3 and Geographic Atrophy in Age-Related Macular Degeneration,' N Eng J Med, 359(14):1456-63.
Yu et al., (2004), 'Regulation of an ATG7-Beclin 1 Program of Autophagic Cell Death by Caspase-8,' Science, 304(5676):1500-2.
Yuan et al., (2000) 'Tumor Necrosis Factor-$\alpha$: A Potentially Neurodestructive Cytokine Produced by Glia in the Human Glaucomatous Optic Nerve Head,' Glia, 32(1):42-50.
Zacks et al., (2003), 'Caspase Activation in an Experimental Model of Retinal Detachment,' Invest Ophthalmol Vis Sci, 44(3):1262-7.
Zacks et al., (2004), 'FAS-Mediated Apoptosis and Its Relation to Intrinsic Pathway Activation in an Experimental Model of Retinal Detachment,' Invest Ophthalmol Vis Sci, 45(12):4563-9.
Zacks et al., (2007), Role of the Fas-Signaling Pathway in Photoreceptor Neuroprotection, Arch Ophthamol, 125(10):1389-95.
Zhang et al., (2009), 'RIP3, an Energy Metabolism Regulator that Switches TNF-Induced Cell Death from Apoptosis to Necrosis,' Science, 325(5938):332-6.
Zheng et al., (2008), 'Structure-Activity Relationship Study of a Novel Necroptosis Inhibitor, Necrostatin-7,' Bioorg Med Chem Lett, 18(18):4932-5.
Zhu et al., (2000), 'Stabilization of Proteins Encapsulated in Injectable Poly (Lactide-co-glycolide),' Nature Biotech, 18(1):52-7.
Zhu et al., (2011), 'Necrostatin-1 Ameliorates Symptoms in R6/2 Transgenic Mouse Model of Huntington's Disease,' Cell Death Dis, 2:e115 (4 pages).
Zitvogel et al., (2010), 'Decoding Cell Death Signals in Inflammation and Immunity,' Cell, 140(6):798-804.
Susin (2000) 'Two Distinct Pathways Leading to Nuclear Apoptosis,' J Exp Med. 192(4):571-80.

ONC

ONC Nec1  x3(D0,D3,D7)

ONC ZVAD  x3(D0,D3,D7)

ONC Nec1+ZVAD x1(D0)

ONC Nec1+ZVAD x3(D0,D3,D7)

SEQUENCE LISTING

```
<160> NUMBER OF SEQ ID NOS: 55

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde

<400> SEQUENCE: 1

Ala Ala Val Ala Leu Leu Pro Ala Val Leu Leu Ala Leu Leu Pro Tyr
1               5                   10                  15

Val Ala Asp

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde

<400> SEQUENCE: 2

Ala Ala Val Ala Leu Leu Pro Ala Val Leu Leu Ala Leu Leu Ala Pro
1               5                   10                  15

Asp Glu Val Asp
            20

<210> SEQ ID NO 3
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde

<400> SEQUENCE: 3

Ala Ala Val Ala Leu Leu Pro Ala Val Leu Leu Ala Leu Leu Ala Pro
1               5                   10                  15

Leu Glu Val Pro
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde

<400> SEQUENCE: 4

Ala Ala Val Ala Leu Leu Pro Ala Val Leu Leu Ala Leu Leu Ala Pro
1               5                   10                  15

Val Glu Ile Asp
            20

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde

<400> SEQUENCE: 5

Ala Ala Val Ala Leu Leu Pro Ala Val Leu Leu Ala Leu Leu Ala Pro
1               5                   10                  15

Ile Glu Thr Asp
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde

<400> SEQUENCE: 6

Ala Ala Val Ala Leu Leu Pro Ala Val Leu Leu Ala Leu Leu Ala Pro
1               5                   10                  15
```

Leu Glu His Asp
            20

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: N-Me-Tyr
<220> FEATURE:
<223> OTHER INFORMATION: C-term aldehyde

<400> SEQUENCE: 7

Tyr Val Ala Asp
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde

<400> SEQUENCE: 8

Trp Glu His Asp
1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: N-Me-Val
<220> FEATURE:
<221> NAME/KEY: MOD_RES
<222> LOCATION: (4)..(4)
<223> OTHER INFORMATION: N-Me-Asp
<220> FEATURE:
<223> OTHER INFORMATION: C-term aldehyde

<400> SEQUENCE: 9

Tyr Val Ala Asp
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac

```
<220> FEATURE:
<223> OTHER INFORMATION: C-term aldehyde

<400> SEQUENCE: 10

Tyr Val Ala Asp
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term chloromethylketone

<400> SEQUENCE: 11

Tyr Val Ala Asp
1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term 2,6-dimethylbenzoyloxymethylketone

<400> SEQUENCE: 12

Tyr Val Ala Asp
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Asp(OtBu)
<220> FEATURE:
<223> OTHER INFORMATION: C-term aldehyde-dimethyl acetol

<400> SEQUENCE: 13

Tyr Val Ala Asp
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde
```

```
<400> SEQUENCE: 14

Tyr Val Lys Asp
1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: Lys(biotinyl)
<220> FEATURE:
<223> OTHER INFORMATION: C-term 2,6-dimethylbenzoyloxymethylketone

<400> SEQUENCE: 15

Tyr Val Lys Asp
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotinyl
<220> FEATURE:
<223> OTHER INFORMATION: C-term chloromethylketone

<400> SEQUENCE: 16

Tyr Val Ala Asp
1

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term ethoxycarbonyl
<220> FEATURE:
<223> OTHER INFORMATION: C-term aldehyde (pseudo acid)

<400> SEQUENCE: 17

Ala Tyr Val Ala Asp
1               5

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term benzyloxycarbonyl
<220> FEATURE:
<223> OTHER INFORMATION: C-term chloromethylketone

<400> SEQUENCE: 18

Tyr Val Ala Asp
```

```
<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term benzyloxycarbonyl
<220> FEATURE:
<221> NAME/KEY: MOD_RES
<222> LOCATION: (4)..(4)
<223> OTHER INFORMATION: D/L-Asp
<220> FEATURE:
<223> OTHER INFORMATION: C-term fluoromethlyketone

<400> SEQUENCE: 19

Tyr Val Ala Asp
1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin
<220> FEATURE:
<223> OTHER INFORMATION: C-term fluoroacyloxymethylketone

<400> SEQUENCE: 20

Tyr Val Ala Asp
1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term acyloxymethylketone

<400> SEQUENCE: 21

Tyr Val Ala Asp
1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term benzyloxycarbonyl
<220> FEATURE:
<223> OTHER INFORMATION: C-term fluoromethylketone

<400> SEQUENCE: 22

Tyr Val Ala Asp
1
```

```
<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde

<400> SEQUENCE: 23

Val Asp Val Ala Asp
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term benzyloxycarbonyl
<220> FEATURE:
<223> OTHER INFORMATION: C-term fluoromethlyketone

<400> SEQUENCE: 24

Val Asp Val Ala Asp
1               5

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde (pseudo acid)

<400> SEQUENCE: 25

Glu Ser Met Asp
1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde (pseudo acid)

<400> SEQUENCE: 26

Ile Glu Thr Asp
1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Ac
<220> FEATURE:
<223> OTHER INFORMATION: C-term aldehyde

<400> SEQUENCE: 27

Asp Glu Val Asp
1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde

<400> SEQUENCE: 28

Asp Met Gln Asp
1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotinyl
<220> FEATURE:
<223> OTHER INFORMATION: C-term aldehyde

<400> SEQUENCE: 29

Asp Glu Val Asp
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term benzyloxycarbonyl
<220> FEATURE:
<223> OTHER INFORMATION: C-term chloromethylketone

<400> SEQUENCE: 30

Asp Glu Val Asp
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term benzyloxycarbonyl
<220> FEATURE:
<221> NAME/KEY: MOD_RES
<222> LOCATION: (1)..(1)
<223> OTHER INFORMATION: Asp(OMe)
<220> FEATURE:
```

```
<221> NAME/KEY: MOD_RES
<222> LOCATION: (2)..(2)
<223> OTHER INFORMATION: Glu(OMe)
<220> FEATURE:
<221> NAME/KEY: MOD_RES
<222> LOCATION: (4)..(4)
<223> OTHER INFORMATION: D/L-Asp(OMe)
<220> FEATURE:
<223> OTHER INFORMATION: C-term fluoromethlyketone

<400> SEQUENCE: 31

Asp Glu Val Asp
1

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin
<220> FEATURE:
<221> NAME/KEY: MOD_RES
<222> LOCATION: (1)..(1)
<223> OTHER INFORMATION: Any amino acid
<220> FEATURE:
<223> OTHER INFORMATION: C-term fluoromethlyketone

<400> SEQUENCE: 32

Xaa Asp Glu Val Asp
1               5

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term chloromethylketone

<400> SEQUENCE: 33

Asp Glu Val Asp
1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term N-benzyloxycarbonal
<220> FEATURE:
<221> NAME/KEY: MOD_RES
<222> LOCATION: (1)..(1)
<223> OTHER INFORMATION: Asp(OMe)
<220> FEATURE:
<221> NAME/KEY: MOD_RES
<222> LOCATION: (2)..(2)
<223> OTHER INFORMATION: Glu(OMe)
<220> FEATURE:
<221> NAME/KEY: MOD_RES
<222> LOCATION: (4)..(4)
<223> OTHER INFORMATION: Asp(OMe)
<220> FEATURE:
<223> OTHER INFORMATION: C-term fluoromethylketone
```

-continued

```
<400> SEQUENCE: 34

Asp Glu Val Asp
1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde

<400> SEQUENCE: 35

Leu Glu Val Asp
1

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term benzyloxycarbonyl
<220> FEATURE:
<221> NAME/KEY: MOD_RES
<222> LOCATION: (4)..(4)
<223> OTHER INFORMATION: D/L-Asp
<220> FEATURE:
<223> OTHER INFORMATION: C-term fluoromethlyketone

<400> SEQUENCE: 36

Tyr Val Ala Asp
1

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term benzyloxycarbonyl
<220> FEATURE:
<223> OTHER INFORMATION: C-term fluoromethlyketone

<400> SEQUENCE: 37

Trp His Glu Asp
1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde

<400> SEQUENCE: 38
```

Trp Glu His Asp
1

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term benzyloxycarbonyl
<220> FEATURE:
<221> NAME/KEY: MOD_RES
<222> LOCATION: (2)..(2)
<223> OTHER INFORMATION: Glu(OMe)
<220> FEATURE:
<221> NAME/KEY: MOD_RES
<222> LOCATION: (4)..(4)
<223> OTHER INFORMATION: Asp(OMe)
<220> FEATURE:
<223> OTHER INFORMATION: C-term fluoromethlyketone

<400> SEQUENCE: 39

Trp Glu His Asp
1

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde

<400> SEQUENCE: 40

Val Glu Ile Asp
1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term benzyloxycarbonyl
<220> FEATURE:
<223> OTHER INFORMATION: C-term fluoromethlyketone

<400> SEQUENCE: 41

Val Glu Ile Asp
1

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term benzyloxycarbonyl
<220> FEATURE:
<221> NAME/KEY: MOD_RES
<222> LOCATION: (1)..(1)
<223> OTHER INFORMATION: Asp(OMe)

```
<220> FEATURE:
<221> NAME/KEY: MOD_RES
<222> LOCATION: (4)..(4)
<223> OTHER INFORMATION: Asp(OMe)
<220> FEATURE:
<223> OTHER INFORMATION: C-term fluoromethlyketone

<400> SEQUENCE: 42

Asp Gln Met Asp
1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde

<400> SEQUENCE: 43

Asp Glu Val Asp
1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin
<220> FEATURE:
<223> OTHER INFORMATION: C-term fluoromethlyketone

<400> SEQUENCE: 44

Asp Glu Val Asp
1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term benzyloxycarbonyl
<220> FEATURE:
<223> OTHER INFORMATION: C-term fluoromethlyketone

<400> SEQUENCE: 45

Asp Glu Val Asp
1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde
```

```
<400> SEQUENCE: 46

Asp Glu Val Asp
1

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde

<400> SEQUENCE: 47

Ile Glu Pro Asp
1

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde

<400> SEQUENCE: 48

Ile Glu Thr Asp
1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde

<400> SEQUENCE: 49

Trp Glu His Asp
1

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Boc
<220> FEATURE:
<223> OTHER INFORMATION: C-term aldehyde

<400> SEQUENCE: 50

Ala Glu Val Asp
1

<210> SEQ ID NO 51
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term benzyloxycarbonyl
<220> FEATURE:
<223> OTHER INFORMATION: C-term fluoromethlyketone

<400> SEQUENCE: 51

Ile Glu Thr Asp
1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde

<400> SEQUENCE: 52

Asp Glu Val Asp
1

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term aldehyde

<400> SEQUENCE: 53

Leu Glu His Asp
1

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term chloromethylketone

<400> SEQUENCE: 54

Leu Glu His Asp
1

<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: N-term benzyloxycarbonyl
<220> FEATURE:
<223> OTHER INFORMATION: C-term fluoromethlyketone

<400> SEQUENCE: 55

Leu Glu His Asp
1
```

METHODS AND COMPOSITIONS FOR PRESERVING RETINAL GANGLION CELLS

CROSS-REFERENCE TO RELATED APPLICATIONS

This application is a continuation of U.S. patent application Ser. No. 15/093,480, filed Apr. 7, 2016 (issued as U.S. Pat. No. 9,993,517, on Jun. 12, 2018), which is a continuation of U.S. patent application Ser. No. 13/882,932, filed Sep. 30, 2013 (now abandoned), which is the national stage filing under 35 U.S.C. § 371 of International Patent Application No. PCT/US2011/057327, filed Oct. 21, 2011, which claims the benefit of and priority to U.S. Provisional Application No. 61/409,055, filed Nov. 1, 2010; U.S. Provisional Application No. 61/414,862, filed Nov. 17, 2010; and U.S. Provisional Application No. 61/472,144, filed Apr. 5, 2011; the disclosures of each application are hereby incorporated by reference in their entirety.

GOVERNMENT FUNDING

The work described in this application was sponsored, in part, by the National Eye Institute under Grant No. EY14104. The United States Government has certain rights in the invention.

FIELD OF THE INVENTION

The field of the invention relates generally to methods and compositions for preserving the viability of retinal ganglion cells (RGCs), for example, in a subject affected with an ocular disorder wherein a symptom of the ocular disorder is loss of retinal ganglion cell viability. More particularly, the invention relates to the use of a necrosis inhibitor, e.g., a RIP kinase inhibitor, e.g., a necrostatin, either alone or in combination with an apoptosis inhibitor, e.g., a pan-caspase inhibitor, for preserving the viability of retinal ganglion cells for the treatment of the ocular disorder. The invention further relates to the use a necrosis inhibitor, either alone or in combination with an apoptosis inhibitor, for promoting axon regeneration with retinal ganglion cells.

BACKGROUND OF THE INVENTION

The retina is a delicate neural tissue lining the back of the eye that converts light stimuli into electric signals for processing by the brain. The optic nerve is a cable of retinal ganglion cells that carry the electric signals from the retina to the brain. Diseases affecting the retina and optic nerve, including, for example, glaucoma, and optic nerve injury can lead to vision loss and blindness. Early detection and treatment are critical in correcting problems before vision is lost in preventing further deterioration of vision.

In the United States, glaucoma is the second leading cause of blindness overall. Glaucoma is a progressive disease which leads to optic nerve damage and, ultimately, total loss of vision. The causes of this disease have been the subject of extensive studies for many years, but are still not fully understood. The principal symptom of and/or risk factor for the disease is elevated intraocular pressure or ocular hypertension due to excess aqueous humor in the anterior chamber of the eye. Unfortunately, many of the drugs conventionally used to treat ocular hypertension have a variety of problems. For instance, miotics such as pilocarpine can cause blurring of vision and other visual side effects, which may lead either to decreased patient compliance or to termination of therapy.

Thus, there is a continuing need for therapies that control elevated intraocular pressure associated with glaucoma without the degree of undesirable side-effects attendant to most conventional therapies.

Damage to the optic nerve (ON) typically causes permanent and potentially severe loss of vision. Like most pathways in the mature central nervous system, the optic nerve cannot regenerate if injured. Optic nerve injury can be the result of glaucoma, trauma, toxicity, inflammation, ischemia, congenital diseases, or compression from tumors or aneurysms. To date, few effective treatments have been discovered to restore visual function and/or axon regeneration following optic nerve injury.

Apoptosis and necrosis represent two different mechanisms of cell death. Apoptosis is a highly regulated process involving the caspase family of cysteine proteases, and characterized by cellular shrinkage, chromatin condensation, and DNA degradation. In contrast, necrosis is associated with cellular and organelle swelling and plasma membrane rupture with ensuing release of intracellular contents and secondary inflammation (Kroemer et al., (2009) CELL DEATH DIFFER 16:3-11). Necrosis has been considered a passive, unregulated form of cell death; however, recent evidence indicates that some necrosis can be induced by regulated signal transduction pathways such as those mediated by receptor interacting protein (RIP) kinases, especially in conditions where caspases are inhibited or cannot be activated efficiently (Golstein P & Kroemer G (2007) TRENDS BIOCHEM. SCI. 32:37-43; Festjens et al. (2006) BIOCHIM. BIOPHYS. ACTA 1757:1371-1387). Stimulation of the Fas and TNFR family of death domain receptors (DRs) is known to mediate apoptosis in most cell types through the activation of the extrinsic caspase pathway. In addition, in certain cells deficient for caspase-8 or treated with pan-caspase inhibitor Z-VAD, stimulation of death domain receptors (DR) causes a RIP-1 kinase dependent programmed necrotic cell death instead of apoptosis (Holler et al. (2000) NAT. IMMUNOL. 1:489-495; Degterev et al. (2008) NAT. CHEM. BIOL. 4:313-321). This novel mechanism of cell death is termed "programmed necrosis" or "necroptosis" (Degterev et al., (2005) NAT CHEM BIOL 1:112-119).

Receptor Interacting Protein kinase 1 (RIP-1) is a serine/threonine kinase that contains a death domain and forms a death signaling complex with the Fas-associated death domain and caspase-8 in response to death receptor (DR) stimulation (Festjens et al. (2007) CELL DEATH DIFFER. 14:400-410). During death domain receptor-induced apoptosis, RIP-1 is cleaved and inactivated by caspase-8, the process of which is prevented by caspase inhibition (Lin et al. (1999) GENES. DEV. 13:2514-2526). It has been unclear how RIP-1 kinase mediates programmed necrosis, but recent studies revealed that the expression of RIP-3 and the RIP-1-RIP-3 binding through the RIP homotypic interaction motif is a prerequisite for RIP-1 kinase activation, leading to reactive oxygen species (ROS) production and necrotic cell death (He et al., (2009) CELL 137:1100-1111; Cho et. al., (2009) CELL 137:1112-1123; Zhang et al., (2009) SCIENCE 325:332-336).

There is still an ongoing need to minimize or eliminate cell death, e.g., retinal ganglion cell death, in certain ocular disorders, e.g., in glaucoma and optic nerve injury. It is contemplated that minimizing retinal ganglion cell death and/or promoting axon regeneration in the retinal ganglion cells will reduce the loss of vision or the loss of visual function associated with these various ocular disorders.

SUMMARY OF THE INVENTION

The invention is based, in part, on the discovery that a necrosis inhibitor, e.g., RIP kinase inhibitor, e.g., a necrostatin, e.g., necrostatin-1, can be used to reduce or prevent the loss of retinal ganglion cell viability, especially when the necrosis inhibitor is combined with an apoptotic inhibitor (e.g., a pan-caspase inhibitor, e.g., Z-VAD and/or IDN-6556). It was previously understood that retinal ganglion cell death associated with glaucoma and optic nerve injury was primarily caused by apoptosis. However, studies have shown that the administration of Z-VAD, an apoptosis inhibitor (i.e., a pan-caspase inhibitor), fails to thoroughly prevent retinal ganglion cell loss in glaucoma and optic nerve injury. The studies described hereinbelow indicate that, in the presence of an apoptosis inhibitor (e.g., a pan-caspase inhibitor), retinal ganglion cells die by necrosis, including necroptosis (or programmed necrosis). These studies show that programmed necrosis is a critical mechanism for ocular disorders wherein a symptom of the disorder is the loss of retinal ganglion cell viability in the presence of a pan-caspase inhibitor. As a result, it is possible to reduce the loss of visual function associated with an ocular disorder, in particular while the ocular disorder is being treated, by reducing the loss of retinal ganglion cell viability.

In one aspect, provided herein is a method preserving the visual function of an eye of a subject with an ocular condition, wherein a symptom of the ocular condition is the loss of retinal ganglion cell viability in the retina of the eye with the condition. The method comprises (a) administering to the eye of the subject an effective amount of a necrosis inhibitor and an effective amount of an apoptosis inhibitor thereby preserving the viability of the retinal ganglion cells disposed within the retina of the eye, and (b) then measuring the visual function (e.g., visual acuity) of the eye after the administration of the necrosis inhibitor and the apoptosis inhibitor. After administration of the necrosis inhibitor and the apoptosis inhibitor the visual function (e.g., visual acuity) of the eye may be preserved or improved relative to the visual function of the eye prior to administration of the necrosis inhibitor and the apoptosis inhibitor. The ocular condition may include, but is not limited to, glaucoma, optic nerve injury, optic neuritis, optic neuropathies, central retinal artery occlusion, central retinal vein occlusion and diabetic retinopathy. In an exemplary embodiment, the ocular condition is glaucoma or optic nerve injury.

In another aspect, provided herein is a method of preserving the viability of retinal ganglion cells within the retina of a subject with an ocular condition. A symptom of the ocular condition may be the loss of retinal ganglion cells in the retina of the eye with the condition. The ocular condition may be glaucoma, optic nerve injury, optic neuritis, optic neuropathies, central retinal artery occlusion, central retinal vein occlusion and diabetic retinopathy. The method comprises administering to the eye of the subject an effective amount of a necrosis inhibitor and an apoptosis inhibitor thereby preserving the viability of the retinal ganglion cells with the retina of the subject with the condition. After the administration of the necrosis inhibitor and the apoptosis inhibitor, the retinal ganglion cell is capable of supporting axonal regeneration.

In another aspect, provided herein is a method of preserving visual function of an eye of a subject affected with an ocular condition such as glaucoma or optic nerve injury, wherein a symptom of the ocular condition is loss of retinal ganglion cell viability, e.g., glaucoma, optic nerve injury, optic neuritis, optic neuropathies, central retinal artery occlusion, central retinal vein occlusion and diabetic retinopathy. The method comprises reducing the production and/or activity of a RIP-1 kinase and/or RIP-3 kinase in the eye thereby preserving the viability of the retinal ganglion cells disposed with the retina of the eye. In certain embodiments, the reduction in the production or activity of the RIP-1 kinase and/or the RIP-3 kinase can be achieved by administering an effective amount of RIP kinase (RIPK) inhibitor, e.g., a necrostatin.

In another aspect, provided herein is a method of preserving the visual function of an eye of a subject affected with an ocular condition wherein a symptom of the ocular condition is loss of retinal ganglion cell viability in the retina of the eye. The method comprises (a) reducing the production or activity of a RIP-1 kinase and/or a RIP-3 kinase in the eye thereby to preserve the viability of the retinal ganglion cells disposed within the retina of the eye; and (b), after treatment, measuring visual function (e.g., visual acuity) of the eye. In certain embodiments, the reduction in the production or activity of the RIP-1 kinase and/or the RIP-3 kinase can be achieved by administering an effective amount of RIPK inhibitor, e.g., a necrostatin. After administration of the RIPK inhibitor the visual function of the eye may be preserved or improved relative to the visual function of the eye prior to administration of the RIPK inhibitor.

In another aspect, the provided herein is a method for promoting axonal regeneration in an eye of a subject with an ocular condition, wherein a symptom of the ocular condition is the loss of retinal ganglion cell viability in the retina of an eye with the condition. The method comprises administering to the eye of the subject with the condition an effective amount of a necrosis inhibitor and an effective amount of an apoptosis inhibitor thereby to promote the regeneration of a retinal ganglion cell axon within the retina of the eye. The method may further comprise, after administration of the necrosis inhibitor and the apoptosis inhibitor, measuring visual function of the eye. After administration of the necrosis inhibitor and the apoptosis inhibitor the visual function of the eye may be preserved or improved relative to the visual function of the eye prior to administration of the necrosis inhibitor and the apoptosis inhibitor. Visual function may be an indication of axon regeneration in the retinal ganglion cell. The ocular condition may include, but is not limited to, glaucoma, optic nerve injury, optic neuritis, optic neuropathies, central retinal artery occlusion, central retinal vein occlusion and diabetic retinopathy.

In another aspect, provided herein is a combination of a necrosis inhibitor (e.g., a RIPK inhibitor, e.g., a necrostatin) and an apoptosis inhibitor (e.g., a pan-caspase inhibitor, e.g., Z-VAD or IDN-6556), for use in preserving visual function of an eye of a subject affected with an ocular condition wherein a symptom of the ocular condition is loss of retinal ganglion cell viability in the retina of the eye with the condition. The ocular condition may be glaucoma, optic nerve injury, optic neuritis, optic neuropathies, central retinal artery occlusion, central retinal vein occlusion and diabetic retinopathy.

In another aspect, provided herein is a combination of a necrosis inhibitor (e.g., a RIPK inhibitor, e.g., a necrostatin) and an apoptosis inhibitor (e.g., a pan-caspase inhibitor, e.g., Z-VAD or IDN-6556), for use in preserving the viability of retinal ganglion cells disposed in the eye of a subject with an ocular condition, wherein a symptom of the ocular condition is the loss of retinal ganglion cell viability in the retina of the eye with the condition. The ocular condition may be glaucoma, optic nerve injury, optic neuritis, optic neuropathies, central retinal artery occlusion, central retinal vein occlusion and diabetic retinopathy.

In addition, provided herein is a combination of a necrosis inhibitor (e.g., a RIPK inhibitor, e.g., a necrostatin) and an apoptosis inhibitor (e.g., a pan-caspase inhibitor, e.g., Z-VAD or IDN-6556), for use in promoting axon regeneration mediated via retinal ganglion cells in a subject with an ocular condition, for example, optic nerve injury.

In each of the foregoing aspects and methods, the necrosis inhibitor can be a RIP kinase inhibitor, for example, a necrostatin. In certain embodiments of the foregoing methods, the necrostatin is necrostatin-1, necrostatin-2, necrostatin-3, necrostatin-4, necreostatin-5, necrostatin-7, or a combination thereof.

In certain embodiments, when a necrostatin is administered, the necrostatin is administered to provide a final concentration of necrostatin in the eye greater than about 5 µM. For example, the final concentration of necrostatin in the eye may range from about 5 µM to about 1000 µM, about 10 µM to about 1000 µM, about 100 µM to about 1000 µM, about 150 µM to about 1000 µM, from about 200 µM to about 800 µM or from about 200 µM to about 600 µM. In certain embodiments, the final concentration of necrostatin in the eye is about 400 µM. In other embodiments when a necrostatin is administered, from about 0.05 mg to about 2 mg, 0.1 mg to about 1 mg, from about 0.2 mg to about 1 mg, or from about 0.2 mg to about 0.8 mg, of necrostatin can be administered locally to the eye of a mammal. In an exemplary embodiment, about 0.5 mg of necrostatin can be administered locally to the eye of a mammal.

In certain embodiments, when a pan-caspase inhibitor is administered, the pan-caspase inhibitor is administered to provide a final concentration of the pan-caspase inhibitor in eye greater than about 3 µM. For example, the final concentration of pan-caspase inhibitor in the eye may range from about 3 µM to about 500 µM, about 10 µM to about 500 µM, about 100 µM to about 500 µM, about 150 µM to about 500 µM, or from about 200 µM to about 400 µM. In certain embodiments, the final concentration of the pan-caspase inhibitor in the eye is about 300 µM. Exemplary pan-caspase inhibitors include zVAD, IDN-6556 or a combination thereof. In other embodiments, from about 0.05 mg to about 1.5 mg, from about 0.15 mg to about 1.5 mg, from about 0.2 mg to about 1 mg, from about 0.2 mg to about 0.8 mg, from about 0.4 mg to about 1 mg, or from about 0.5 mg to about 0.8 mg, of the pan-caspase inhibitor can be administered locally to the eye of a mammal. In an exemplary embodiment, about 0.7 mg of a pan-caspase inhibitor can be administered locally to the eye of a mammal.

The necrosis inhibitor, e.g., a necrostatin, and/or the apoptosis inhibitor may be administered to the eye by intraocular, intravitreal, subretinal or trasscleral administration. The necrosis inhibitor, e.g., a necrostatin, and/or the apoptosis inhibitor may be solubilized in a viscoelastic carrier that is introduced into the eye. In other embodiments, the necrosis inhibitor, e.g., a necrostatin, and/or the apoptosis inhibitor may be administered systemically.

It is understood that the necrosis inhibitor, e.g., a necrostatin, and/or the apoptosis inhibitor may be administered sequentially or simultaneously. The necrosis inhibitor, e.g., a necrostatin, and the apoptosis inhibitor may be administered in the same or different carriers.

In each of the foregoing methods and compositions, the necrostatin can be selected from one or more of the following necrostatins. For example, in certain embodiments, the necrostatin is a Nec-1 related compound of Formula I:

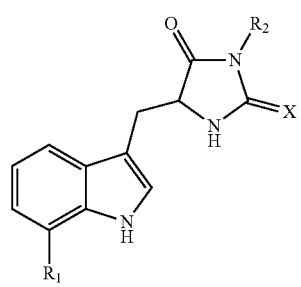

(I)

or a pharmaceutically acceptable salt, ester, or prodrug thereof, wherein

X is O or S;

$R_1$ is hydrogen, $C_1$-$C_6$alkyl, $C_1$-$C_6$alkoxyl, or halogen; and $R_2$ is hydrogen or $C_1$-$C_6$alkyl.

In each of the foregoing methods and compositions, the necrostatin can be a Nec-1 related compound of Formula I-A:

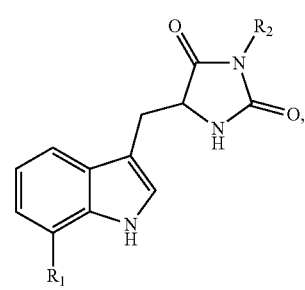

(I-A)

or a pharmaceutically acceptable salt, ester, or prodrug thereof, or optical isomers or racemic mixtures thereof, wherein $R_1$ is H, alkyl, alkoxyl, or a halogen and $R_2$ is H or an alkyl.

In each of the foregoing methods and compositions, the necrostatin can be a Nec-1 related compound of Formula I-B:

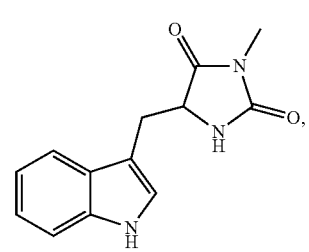

(I-B)

or a pharmaceutically acceptable salt, ester, or prodrug thereof.

In each of the foregoing methods and compositions, the necrostatin can be a Nec-1 related compound of Formula I-C:

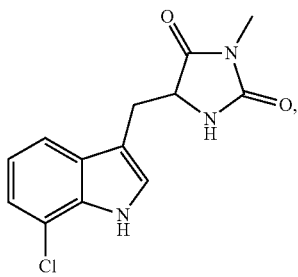

(I-C)

or a pharmaceutically acceptable salt, ester, or prodrug thereof.

In each of the foregoing methods and compositions, the necrostatin can be a Nec-1 related compound of Formula I-D:

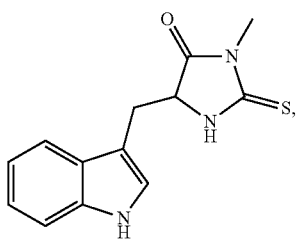

(I-D)

or a pharmaceutically acceptable salt, ester, or prodrug thereof.

In each of the foregoing methods and compositions, the necrostatin can be a Nec-1 related compound of Formula I-E:

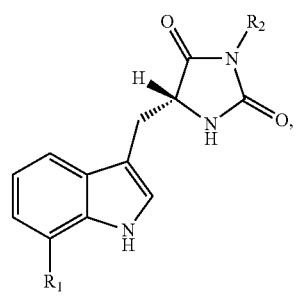

(I-E)

or a pharmaceutically acceptable salt, ester, or prodrug thereof, wherein $R_1$ is H, alkyl, alkoxyl, or a halogen (for example, F, Cl, Br or I) and $R_2$ is H or an alkyl.

In each of the foregoing methods and compositions, the necrostatin can be a Nec-1 related compound of Formula I-F:

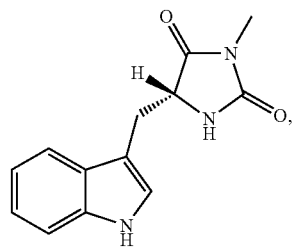

(I-F)

or a pharmaceutically acceptable salt, ester, or prodrug thereof.

In each of the foregoing methods and compositions, the necrostatin can be a Nec-1 related compound of Formula I-G:

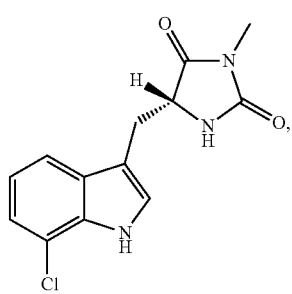

(I-G)

or a pharmaceutically acceptable salt, ester, or prodrug thereof.

In each of the foregoing methods and compositions, the necrostatin can be a Nec-2 related compound of Formula II:

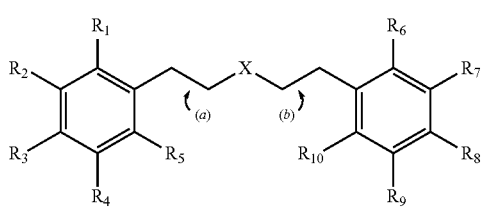

(II)

or a pharmaceutically acceptable salt, ester, or prodrug thereof, wherein:

X is —CH$_2$—, —C(H)(R$_{14}$)—, —C(=S)—, —C(=NH)—, or —C(O)—;

$R_1$, $R_2$, $R_3$, $R_4$, $R_5$, $R_6$, $R_7$, $R_8$, $R_9$, and $R_{10}$ each represent independently hydrogen, acyl, acetyl, alkyl, halogen, amino, $C_1$-$C_6$alkoxyl, nitro, —C(O)R$_{12}$, —C(S)R$_{12}$, —C(O)OR$_{12}$, —C(O)NR$_{12}$R$_{13}$, —C(S)NR$_{12}$R$_{13}$, or —S(O$_2$)R$_{12}$;

$R_{11}$ is hydrogen, acyl, acetyl, alkyl, or acylamino;

$R_{12}$ and $R_{13}$ each represent independently hydrogen, an optionally substituted alkyl, an optionally substituted aryl, an optionally substituted heteroaryl, an optionally substituted aralkyl, or an optionally substituted heteroaralkyl;

$R_{14}$ is acyl, acetyl, alkyl, halogen, amino, acylamino, nitro, —SR$_{11}$, —N(R$_{11}$)$_2$, or —OR$_{11}$;

the bond indicated by (a) can be a single or double bond; and the bond indicated by (b) can be a single or double bond.

In each of the foregoing methods and compositions, the necrostatin can be a Nec-2 related compound of Formula IIA:

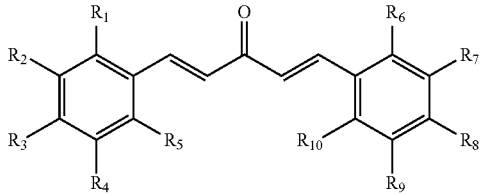

(II-A)

or a pharmaceutically acceptable salt thereof, wherein:

$R_1$, $R_2$, $R_5$, $R_6$, $R_7$, and $R_{10}$ each represent independently hydrogen, alkyl, halogen, amino, or methoxyl; and $R_3$, $R_4$, $R_8$, and $R_9$ are $C_1$-$C_6$alkoxy.

In each of the foregoing methods and compositions, the necrostatin can be a Nec-3 related compound of Formula III:

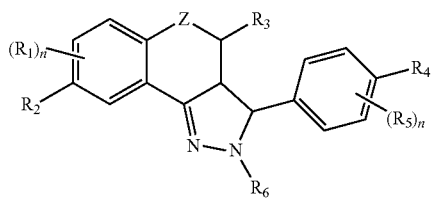

(III)

or a pharmaceutically acceptable salt, ester, or prodrug thereof, wherein:

Z is —$CH_2$—, —$CH_2CH_2$—, —O—, —S—, —S(O)—, —$S(O_2)$—, or —$N(R_7)$—;

$R_1$, $R_3$, and $R_5$ each represent independently for each occurrence hydrogen, halogen, hydroxyl, amino, $C_1$-$C_6$alkyl, $C_1$-$C_6$alkoxy, $C_1$-$C_6$alkoxy-$C_1$-$C_6$alkyl, $C_1$-$C_6$alkanoyl, $C_1$-$C_6$alkylsulfinyl, $C_1$-$C_6$alkylsulfinyl-$C_1$-$C_6$alkyl, $C_1$-$C_6$alkylsulfonyl, $C_1$-$C_6$alkylsulfonyl-$C_1$-$C_6$alkyl, aryl, aralkyl, heterocycloalkyl, heteroaryl, or heteroaralkyl;

$R_2$ and $R_4$ are $C_1$-$C_6$alkoxy;

$R_6$ is —$C(O)R_8$, —$C(S)R_8$, —$C(O)OR_8$, —$C(O)NR_8R_9$, —$C(S)NR_8R_9$, —$C(NH)R_8$, or —$S(O_2)R_8$;

$R_7$ is alkyl, aralkyl, or heteroaralkyl;

$R_8$ and $R_9$ each represent independently hydrogen, $C_1$-$C_6$alkyl, heteroalkyl, aryl, heteroaryl, aralkyl, or heteroaralkyl; and n represents independently for each occurrence 0, 1, or 2.

In each of the foregoing methods and compositions, the necrostatin can be a Nec-4 related compound of Formula IV:

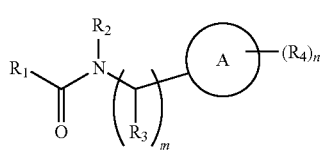

(IV)

or a pharmaceutically acceptable salt, ester, or prodrug thereof, wherein:

$R_1$ is

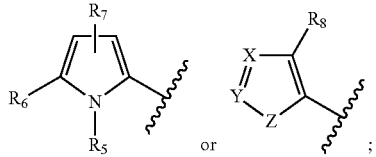

$R_2$ and $R_3$ each represent independently for each occurrence hydrogen or methyl;

$R_4$ represents independently for each occurrence halogen, hydrogen, $C_1$-$C_6$alkyl, $C_2$-$C_6$alkenyl, or $C_2$-$C_4$alkynyl;

$R_5$ is $C_1$-$C_4$alkyl;

$R_6$ is hydrogen, halogen, or —CN;

$R_7$ is hydrogen or $C_1$-$C_4$alkyl;

$R_8$ is $C_1$-$C_6$alkyl, or $R_8$ taken together with $R_9$, when present, forms a carbocyclic ring;

$R_9$ is hydrogen or $C_1$-$C_6$alkyl, or $R_9$ taken together with $R_8$ forms a carbocyclic ring;

$R_{10}$ is hydrogen or $C_1$-$C_6$alkyl;

A is phenylene or a 5-6 membered heteroarylene;

X is N or —$C(R_9)$—;

Y is N or —$C(R_{10})$—;

Z is S or O; and m and n each represent independently 1, 2, or 3.

In each of the foregoing methods and compositions, the necrostatin can be a Nec-4 related compound of Formula IV-A:

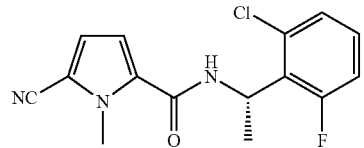 [SMILES: C[C@H](NC(=O)c1ccc(C#N)n1C)c1c(F)cccc1Cl]

or a pharmaceutically acceptable salt thereof.

In each of the foregoing methods and compositions, the necrostatin can be a Nec-5 related compound of Formula V:

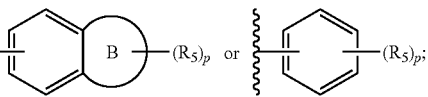

(V)

or a pharmaceutically acceptable salt, ester, or prodrug thereof, wherein:

A is a saturated or unsaturated 5-6 membered carbocyclic ring;

X is a bond or $C_1$-$C_4$alkylene;

$R_1$ is $C_1$-$C_6$ alkyl, halogen, hydroxyl, $C_1$-$C_6$alkoxyl, —$N(R_4)_2$, —$C(O)R_4$, $CO_2R_4$, or $C(O)N(R_4)_2$;

$R_2$ is

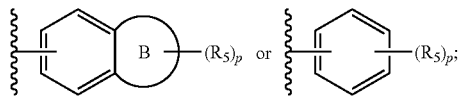

$R_3$ is —$C_1$-$C_6$alkylene-CN, —CN, $C_1$-$C_6$alkyl, or $C_2$-$C_6$alkenyl;

$R_4$ represents independently for each occurrence hydrogen, $C_1$-$C_6$alkyl, aryl, or aralkyl;

$R_5$ represents independently for each occurrence $C_1$-$C_6$alkyl, halogen, hydroxyl, $C_1$-$C_6$alkoxyl, —$N(R_4)_2$, —$C(O)R_4$, $CO_2R_4$, or $C(O)N(R_4)_2$;

B is a 5-6 membered heterocyclic or carbocylic ring; and n and p each represent independently 0, 1, or 2.

In each of the foregoing methods and compositions, the necrostatin can be a Nec-5 related compound of Formula V-A:

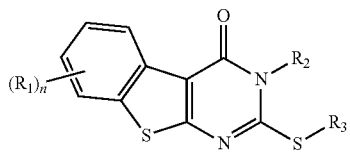

(V-A)

or a pharmaceutically acceptable salt, ester, or prodrug thereof, wherein:

$R_1$ is $C_1$-$C_6$alkyl, halogen, hydroxyl, $C_1$-$C_6$alkoxyl, or —$N(R_4)_2$;

$R_2$ is

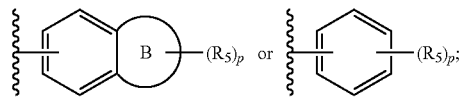

$R_3$ is —$C_1$-$C_6$alkylene-CN;

$R_4$ represents independently for each occurrence hydrogen, $C_1$-$C_6$alkyl, aryl, or aralkyl;

$R_5$ represents independently for each occurrence $C_1$-$C_6$alkyl, halogen, hydroxyl, $C_1$-$C_6$alkoxyl, —$N(R_4)_2$, —$C(O)R_4$, $CO_2R_4$, or $C(O)N(R_4)_2$;

B is a 5-6 membered heterocyclic or carbocylic ring; and n and p each represent independently 0, 1, or 2.

In each of the foregoing methods and compositions, the necrostatin can be a Nec-7 related compound of Formula VII:

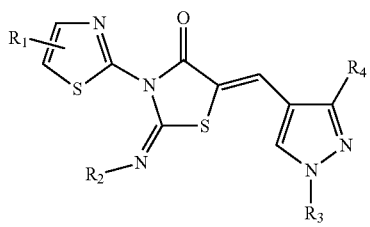

(VII)

or a pharmaceutically acceptable salt, ester, or prodrug thereof, wherein:

$R_1$, $R_2$, and $R_3$ each represent independently hydrogen or $C_1$-$C_4$alkyl;

$R_4$ is

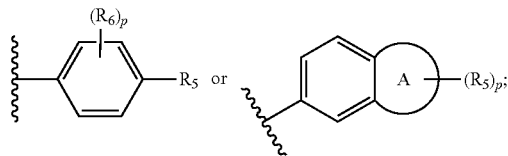

$R_5$ and $R_6$ each represent independently for each occurrence halogen, $C_1$-$C_6$alkyl, hydroxyl, $C_1$-$C_6$alkoxyl, —$N(R_7)_2$, —$NO_2$, —S—$C_1$-$C_6$alkyl, —S-aryl, —$SO_2$—$C_1$-$C_6$alkyl, —$SO_2$-aryl, —$C(O)R_7$, —$CO_2R_7$, —$C(O)N(R_7)_2$, heterocycloalkyl, aryl, or heteroaryl;

$R_7$ represents independently for each occurrence hydrogen, $C_1$-$C_6$alkyl, aryl, or aralkyl; or two occurrences of $R_7$ attached to the same nitrogen atom are taken together with the nitrogen atom to which they are attached to form a 3-7 membered heterocyclic ring;

A is a 5-6 membered heterocyclic ring; and p is 0, 1, or 2.

In each of the foregoing methods and compositions, the necrostatin can be a Nec-7 related compound of Formula VIII:

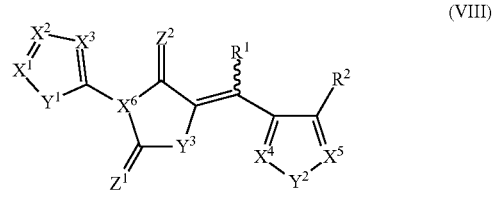

(VIII)

or a pharmaceutically acceptable salt, ester, or prodrug thereof, wherein:

each $X^1$, $X^2$, $X^3$, $X^4$, $X^5$, and $X^6$ is selected, independently, from N or $CR^{X1}$;

each $Y^1$, $Y^2$, and $Y^3$ is selected, independently, from O, S, $NR^{Y1}$, or $CR^{Y2}R^{Y3}$;

each $Z^1$ and $Z^2$ is selected, independently, from O, S, or $NR^{Z1}$;

each $R^{Y1}$ and $R^{Z1}$ is selected, independently, from H, optionally substituted $C_{1-6}$alkyl, optionally substituted $C_{2-6}$alkenyl, optionally substituted $C_{2-6}$alkynyl, optionally substituted cycloalkyl, optionally substituted heterocyclyl, optionally substituted aryl, optionally substituted heteroaryl, —$C(=O)R^{5A}$, —$C(=O)OR^{5A}$, or —$C(=O)NR^{5A}R^{6A}$;

each $R^{X1}$, $R^{Y2}$, and $R^{Y3}$ is selected, independently, from H, halogen, CN, NC, $NO_2$, $N_3$, $OR^3$, $SR^3$, $NR^3R^4$, —$C(=O)R^{5A}$, —$C(=O)OR^{5A}$, —$C(=O)NR^{5A}R^{6A}$, —$S(=O)R^{5A}$, —$S(=O)_2OR^{5A}$, —$S(=O)_2OR^{5A}$, —$S(=O)_2OR^{5A}R^{6A}$, optionally substituted $C_{1-6}$alkyl, optionally substituted $C_{2-6}$alkenyl, optionally substituted $C_{2-6}$alkynyl, optionally substituted cycloalkyl, optionally substituted heterocyclyl, optionally substituted aryl, or optionally substituted heteroaryl;

each $R^1$, $R^2R^{5A}$, $R^{5B}$, $R^{6A}$, and $R^{6B}$ is selected from H, optionally substituted $C_{1-6}$ alkyl, optionally substituted $C_{2-6}$alkenyl, optionally substituted $C_{2-6}$alkynyl, optionally substituted cycloalkyl, optionally substituted heterocyclyl, optionally substituted aryl, or optionally substituted heteroaryl; or $R^{5A}$ and $R^{6A}$, or $R^{5B}$ and $R^{6B}$ combine to form a heterocyclyl; and each $R^3$ and $R^4$ is selected from H, optionally substituted $C_{1-6}$ alkyl, optionally substituted cycloalkyl, optionally substituted heterocyclyl, optionally substituted aryl, optionally substituted heteroaryl, —C(=O)R$^{5B}$, —C(=S)R$^{5B}$, —C(=NR$^{6B}$)R$^{5B}$, —C(=O)OR$^{5B}$, —C(=O)NR$^{5B}$R$^{6B}$, —S(=O)R$^{5B}$, —S(=O)$_2$R$^{5B}$, —S(=O)$_2$OR$^{5B}$, or —S(=O)$_2$NR$^{5B}$R$^{6B}$. In certain embodiments when R$^1$ is H, X$^1$, X$^2$, and X$^4$ are each CH, X$^3$, X$^5$, and X$^6$ are each N, Y$^1$ and Y$^3$ are each S, Y$^2$ is NH, Z$^1$ is NH, and Z$^2$ is O, then R$^2$ is not 4-fluorophenyl.

In each of the foregoing methods and compositions, the necrostatin can be a Nec-4 related compound of Formula IX:

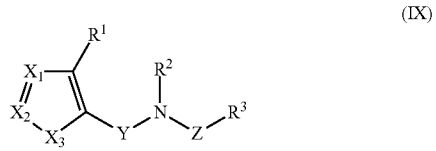

(IX)

or a pharmaceutically acceptable salt, ester, or prodrug thereof, wherein:

X$_1$ and X$_2$ are, independently, N or CR$^4$;

X$_3$ is selected from O, S, NR$^5$, or —(CR$^5$)$_2$;

Y is selected from C(O) or CH$_2$; and

Z is (CR$^6$R$^7$)$_n$;

R$^1$ is selected from H, halogen, optionally substituted C$_{1-6}$alkyl, or optionally substituted C$_{1-6}$cycloalkyl, or optionally substituted aryl;

R$^2$ is selected from H or optionally substituted C$_{1-6}$alkyl;

R$^3$ is optionally substituted aryl;

each R$^4$ is selected from H, halogen, carboxamido, nitro, cyano, optionally substituted C$_{1-6}$alkyl, or optionally substituted aryl;

R$^5$ is selected from H, halogen, optionally substituted C$_{1-6}$alkyl, or optionally substituted aryl;

each R$^6$ and R$^7$ is, independently, selected from H, optionally substituted C$_{1-6}$alkyl, or aryl; and n is 0, 1, 2, or 3. In certain embodiments, when X$_1$ and X$_2$ are N, X$_3$ is S, Y is C(O), Z is CH$_2$, R$^2$ is H, and R$^3$ is 2-chloro-6-fluoro-phenyl, then R$^1$ is not methyl.

The foregoing aspects and embodiments of the invention may be more fully understood by reference to the following figures, detailed description and claims.

BRIEF DESCRIPTION OF THE DRAWINGS

The objects and features of the invention may be more fully understood by reference to the drawings described herein.

FIG. 8B indicates formation of autophagosomes (black arrows) and autolysosome (black arrowheads) in necrotic cells with cellular swelling (left and middle panel) and swollen axons (right panel).

FIGS. 12A-12E show longitudinal sections of the optic nerve stained with an antibody against βIII-tubulin, following optic nerve crush injury. The vertical arrows denote the locations of the injury sites, and the horizontal reference lines denote regions where axon regeneration were detected following treatment with Nec-1 and ZVAD (FIGS. 12D-12E versus FIGS. 12A, 12B, and 12C).

DETAILED DESCRIPTION

The invention relates to methods and composition for preserving the viability of retinal ganglion cells disposed within a retina of an eye of a subject with certain ocular condition, e.g., glaucoma, optic nerve injury, optic neuritis, optic neuropathies, diabetic retinopathy, central retinal artery occlusion, and central retinal vein occulusion, wherein the viability of the retinal ganglion cells are affected by the ocular condition. Using the methods and compositions described herein, it may be possible to preserve or improve visual function in the eye by maintaining retinal ganglion cell viability while the underlying ocular condition is being treated. The methods and compositions described herein may further promote axon regeneration in the retinal ganglion cells and reduce the loss of vision or the loss of visual function associated with the various ocular conditions.

Figure 1:
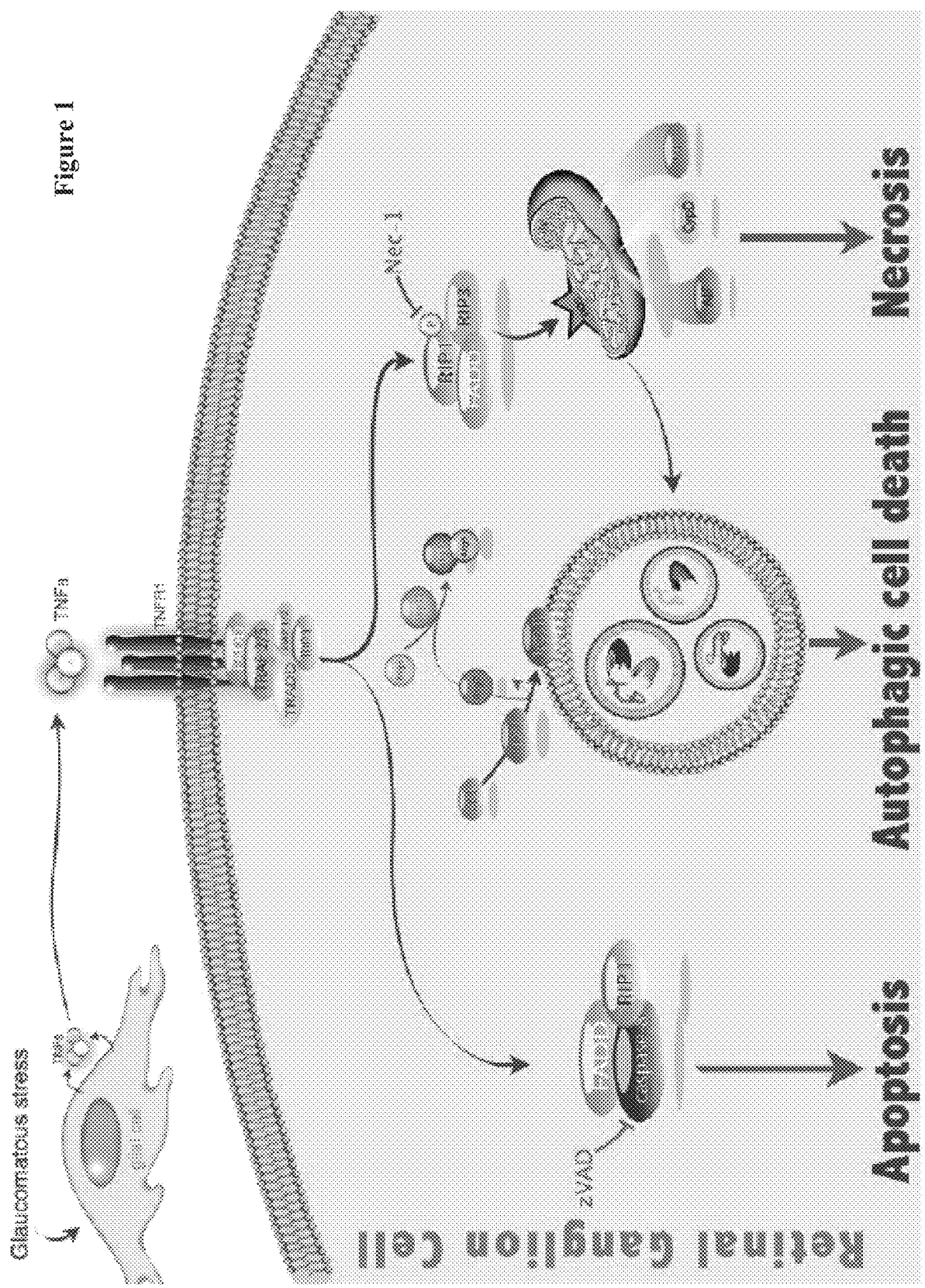
FIG. 1 provides a schematic diagram of retinal ganglion cell death.

As demonstrated herein, programmed necrosis appears to be a critical mechanism of retinal ganglion cell death in certain ocular conditions, for example, glaucoma or optic nerve injury in the presence of an apoptosis inhibitor, e.g., a pan-caspase inhibitor. As depicted in FIG. 1, there are two pathways for cell death (apoptosis and necrosis), which appear to be mediated by RIP-1, a serine/threonine kinase. RIP1 forms a death inducing signaling complex with Fas-associated domain (FADD) and caspase-8, thereby activating caspase-8 and the downstream cascade leading to apoptosis. On the other hand, when caspase pathway is blocked (for example, with a caspase inhibitor such as ZVAD), RIP1 kinase is activated in a RIP1-RIP3 complex and promotes RGC necrosis. Although autophagy is also activated during RGC death, it is mainly associated with necrotic RGC death. Thus, RIP kinases act as common intermediaries for various upstream death signals, and their blockade in addition to caspases is likely necessary for effective neuroprotection.

The methods and compositions described herein are directed to therapies that target both the necrotic and apoptotic pathways of programmed cell death. In particular, the methods and compositions disclosed herein facilitate a combination therapy where a necrosis inhibitor, e.g., a necrostatin (e.g., necrostatin-1 or necrostatin-4), can be administered either alone or in combination (either sequentially or simultaneously) with an apoptosis inhibitor e.g., a pan-caspase inhibitor (e.g., Z-VAD or IDN-6556). In certain embodiments, the disclosed methods surprisingly use necrostatins at concentrations higher than those previously thought to be clinically tolerable. Moreover, it has been demonstrated that the combination of a necrostatin, e.g., necrostatin-1 or necrostatin-4, and a pan-caspase inhibitor, e.g., Z-VAD or IDN-6556, produce a superior effect in reducing retinal ganglion cell death, compared to either drug alone. It has been further demonstrated that the combination treatment of a necrostain and a pan-caspase inhibitor promotes axon regeneration in the retinal ganglion cells following optic nerve injury.

For convenience, certain terms in the specification, examples, and appended claims are collected in this section.

As used herein, the term "cell death" is understood to mean the death of a cell, e.g., by apoptosis or necrosis.

As used herein, the term "apoptosis" is understood to mean caspase-dependent cell death, which is characterized by any of the following properties: cell shrinkage, nuclear condensation, DNA fragmentation or membrane blebbing.

As used herein, the term "apoptosis inhibitor" is understood to mean any agent that, when administered to a mammal, reduces apoptotic cell death in retinal ganglion cells. For example, it is understood that certain useful apoptosis inhibitors act by reducing or eliminating the activity of one or more members of the intrinsic or extrinsic or common apoptotic pathways. Furthermore, it is understood that an agent that either directly or indirectly affects the activity of one or more caspases (e.g., a pan-caspase inhibitor) is considered to be an apoptosis inhibitor. It is understood that a caspase inhibitor can affect the activity of a caspase either directly by modulating a specific caspase in the apoptotic pathway or indirectly by modulating a downstream caspase present in the apoptotic pathway.

As used herein, the term "pan-caspase inhibitor" is understood to mean a broad-spectrum caspase inhibitor that inhibits at least two, preferably at least three different caspases (e.g., caspase-1, caspase-2, caspase-3, caspase-4, caspase-5, caspase-6, caspase-7, caspase-8, caspase-9, caspase-10, caspase-11, caspase-12, caspase-13, and/or caspase-14. Z-VAD (also known as Benzyloxycarbonyl-Val-Ala-Asp(OMe)-fluoromethylketone and carbobenzoxy-valyl-alanyl-aspartyl-[O-methyl]-fluoromethylketone) is an exemplary pan-caspase inhibitor and is available from R&D Systems (Cat. No. FMK001) and Promega (Cat. No. G7231). Other exemplary pan-caspase inhibitors that may be used include IDN-6556 (also known as "PF-3,491,390") available from Conatus Pharmaceuticals, Inc. (formerly Idun Pharmaceuticals, Inc.), VX-799 available from Vertex Pharmaceuticals, Inc., MX1013 available Maxim Pharmaceuticals, Inc., Xyz033mp available from LG Chemical, Inc., all of which are described, for example, in Linton, S. D. (2005) CURRENT TOPICS IN MEDICAL CHEM. 5:1697-1717. It is understood that a "pan-caspase inhibitor" may also be a cocktail (e.g., a combination) of caspase inhibitors including two or more of specific caspase inhibitors (e.g., synthetic or endogenous caspase inhibitors).

As used herein, the term "necrosis" is understood to mean caspase-independent cell death characterized by any of the following properties: cellular and/or organelle swelling, plasma membrane rupture, or discontinuity in plasma, nuclear and/or organelle membranes. As used herein, the terms "necroptosis" and "programmed necrosis" refer to a form of necrosis and is understood to mean one form of programmed or regulated necrosis, and in certain embodiments, necroptosis is mediated by the serine/threonine kinase activity of receptor interacting protein (RIP) kinases, for example, RIP-1 kinase and/or RIP-3 kinase.

As used herein, the term "necrosis inhibitor" is understood to mean an agent, which, when administered to a mammal, reduces necrotic cell death in retinal ganglion cells. For example, it is understood that certain necrosis inhibitors act by reducing or inhibiting necroptosis or programmed necrosis. A necrosis inhibitor can be an agent that modulates the production and/or activity of one or more RIP kinases (e.g., RIP-1 kinase and/or RIP-3 kinase). For example, an inhibitor of RIP-1 kinase is understood to modulate the activity of RIP-1 kinase as well as downstream RIP kinases, e.g., RIP-3 kinase, in the necrosis cascade. Accordingly, a RIP-1 kinase inhibitor is also understood to modulate RIP-3 kinase activity.

As used herein, the term "necrostatin" or "nec" is understood to mean an inhibitor of caspase-independent cell death or necroptosis. Exemplary necrostatins include necrostatin-1

("Nec-1"), necrostatin-2 ("Nec-2"), necrostatin-3 ("Nec-3"), necrostatin-4 ("Nec-4"), necrostatin-5 ("Nec-5") and necrostatin-7 ("Nec-7").

In certain embodiments, the necrostatin is a Nec-1 related compound of Formula I:

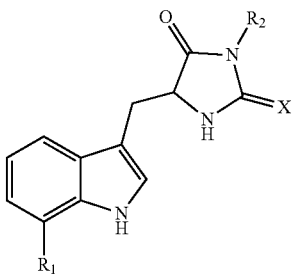

(I)

or a pharmaceutically acceptable salt, ester, or prodrug thereof, wherein
X is O or S;
$R_1$ is hydrogen, $C_1$-$C_6$alkyl, $C_1$-$C_6$alkoxyl, or halogen; and
$R_2$ is hydrogen or $C_1$-$C_6$alkyl.

In certain embodiments, X is O. In certain embodiments, $R_1$ is hydrogen or halogen (such as chlorine). In certain embodiments, $R_2$ is a methyl or ethyl. In certain other embodiments, $R_1$ is hydrogen or Cl, and $R_2$ is a methyl.

In certain embodiments, the necrostatin is a Nec-1 related compound of Formula I-A, shown below:

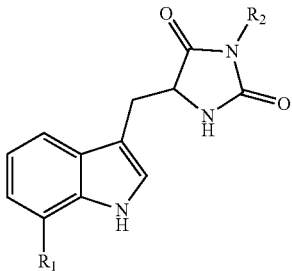

(I-A)

or a pharmaceutically acceptable salt, ester, or prodrug thereof, or optical isomers or racemic mixtures thereof, wherein $R_1$ is H, alkyl, alkoxyl, or a halogen (for example, F, Cl, Br or I) and $R_2$ is H or an alkyl. In certain embodiments, $R_1$ is H or Cl. In certain other embodiments, $R_2$ is a methyl or ethyl. In certain other embodiments, $R_1$ is H or Cl, and $R_2$ is a methyl.

In certain other embodiments, the necrostatin is a Nec-1 related compound of Formula I-B, shown below:

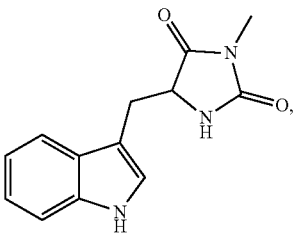

(I-B)

or a pharmaceutically acceptable salt, ester, or prodrug thereof.

In certain other embodiments, the necrostatin is a Nec-1 related compound of Formula I-C, shown below:

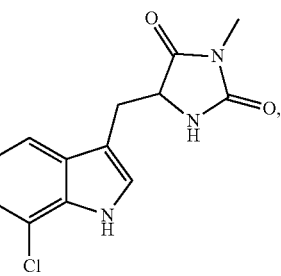

(I-C)

or a pharmaceutically acceptable salt, ester, or prodrug thereof.

In certain other embodiments, the necrostatin is a Nec-1 related compound of Formula I-D, shown below:

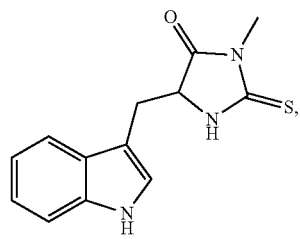

(I-D)

or a pharmaceutically acceptable salt, ester, or prodrug thereof.

In certain other embodiments, the necrostatin is a Nec-1 related compound of Formula I-E, shown below:

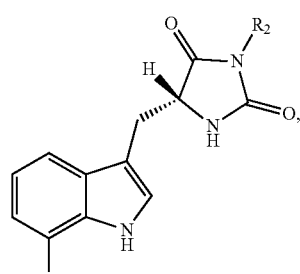

(I-E)

or a pharmaceutically acceptable salt, ester, or prodrug thereof, wherein $R_1$ is H, alkyl, alkoxyl, or a halogen (for example, F, Cl, Br or I) and $R_2$ is H or an alkyl. In certain embodiments, $R_1$ is H or Cl. In certain other embodiments, $R_2$ is a methyl or ethyl. In certain other embodiments, $R_1$ is H or Cl, and $R_2$ is a methyl.

In certain other embodiments, the necrostatin is a Nec-1 related compound of Formula I-F, shown below:

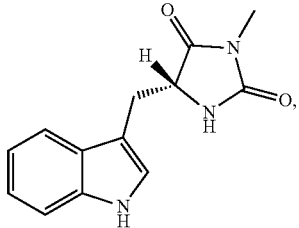

(I-F)

or a pharmaceutically acceptable salt, ester, or prodrug thereof. In certain other embodiments, the necrostatin is a Nec-1 related compound of Formula I-G, shown below:

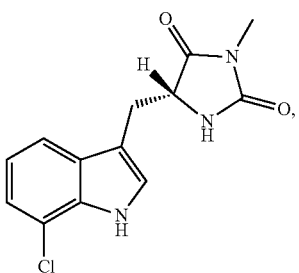

(I-G)

or a pharmaceutically acceptable salt, ester, or prodrug thereof.

The Nec-1 related compounds described above can be prepared based on synthetic procedures described in the literature, such as in Degterev et al., (2005) NAT CHEM BIOL 1:112-119; Degterev et al., (2008) NAT CHEM BIOL 4:313-321; and International Patent Application Publication No. WO 2007/075772, all of which are hereby incorporated by reference.

In certain embodiments, the necrostatin is a Nec-2 related compound of Formula II:

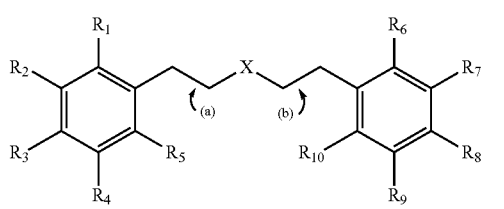

(II)

or a pharmaceutically acceptable salt, ester, or prodrug thereof, wherein:

X is —CH$_2$—, —C(H)(R$_{14}$)—, —C(=S)—, —C(=NH)—, or —C(O)—;

R$_1$, R$_2$, R$_3$, R$_4$, R$_5$, R$_6$, R$_7$, R$_8$, R$_9$, and R$_{10}$ each represent independently hydrogen, acyl, acetyl, alkyl, halogen, amino, C$_1$-C$_6$alkoxyl, nitro, —C(O)R$_{12}$, —C(S)R$_{12}$, —C(O)OR$_{12}$, —C(O)NR$_{12}$R$_{13}$, —C(S)NR$_{12}$R$_{13}$, or —S(O$_2$)R$_{12}$;

R$_{11}$ is hydrogen, acyl, acetyl, alkyl, or acylamino;

R$_{12}$ and R$_{13}$ each represent independently hydrogen, an optionally substituted alkyl, an optionally substituted aryl, an optionally substituted heteroaryl, an optionally substituted aralkyl, or an optionally substituted heteroaralkyl;

R$_{14}$ is acyl, acetyl, alkyl, halogen, amino, acylamino, nitro, —SR$_{11}$, —N(R$_{11}$)$_2$, or —OR$_{11}$;

the bond indicated by (a) can be a single or double bond; and the bond indicated by (b) can be a single or double bond.

In certain embodiments, X is —C(O)—. In certain embodiments, R$_1$, R$_2$, R$_5$, R$_6$, R$_7$, and R$_{10}$ each represent independently hydrogen, acyl, alkyl, halogen, or amino. In certain embodiments, R$_3$, R$_4$, R$_8$, and R$_9$ are C$_1$-C$_6$alkoxyl. In certain embodiments, the bond indicated by (a) is a double bond; and the bond indicated by (b) is a double bond. In certain embodiments, when each of R$_1$, R$_4$, R$_5$, R$_6$, R$_9$ and R$_{10}$ is hydrogen and each of R$_2$, R$_3$, R$_7$, and R$_8$ is methoxyl, then X is not —C(O)—, —CH$_2$—, or —CH(OH)—.

In certain other embodiments, the necrostatin is a Nec-2 related compound of Formula II-A:

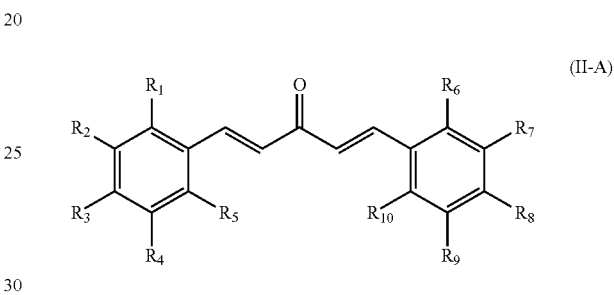

(II-A)

or a pharmaceutically acceptable salt thereof, wherein:

R$_1$, R$_2$, R$_5$, R$_6$, R$_7$, and R$_{10}$ each represent independently hydrogen, alkyl, halogen, amino, or methoxyl; and R$_3$, R$_4$, R$_8$, and R$_9$ are C$_1$-C$_6$alkoxyl.

In certain other embodiments, the Nec-2 related compound is

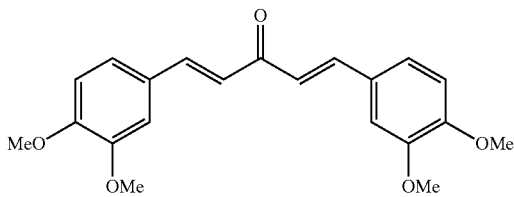 [SMILES: COc1ccc(/C=C/C(=O)/C=C/c2ccc(OC)c(OC)c2)cc1OC]

or a pharmaceutically acceptable salt thereof.

The Nec-2 related compounds described above can be prepared based on synthetic procedures described in the literature, such as in International Patent Application Publication No. WO 2007/075772, which is hereby incorporated by reference.

In certain embodiments, the necrostatin is a Nec-3 related compound of Formula III:

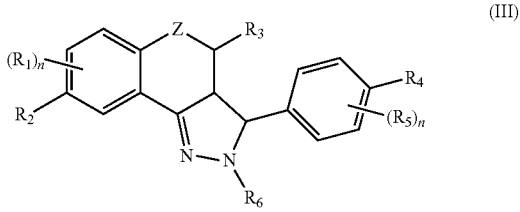

(III)

or a pharmaceutically acceptable salt, ester, or prodrug thereof, wherein:

Z is —CH$_2$—, —CH$_2$CH$_2$—, —O—, —S—, —S(O)—, —S(O$_2$)—, or —N(R$_7$)—;

R$_1$, R$_3$, and R$_5$ each represent independently for each occurrence hydrogen, halogen, hydroxyl, amino, C$_1$-C$_6$alkyl, C$_1$-C$_6$alkoxy, C$_1$-C$_6$alkoxy-C$_1$-C$_6$alkyl, C$_1$-C$_6$alkanoyl, C$_1$-C$_6$alkylsulfinyl, C$_1$-C$_6$alkylsulfinyl-C$_1$-C$_6$alkyl, C$_1$-C$_6$alkylsulfonyl, C$_1$-C$_6$alkylsulfonyl-C$_1$-C$_6$alkyl, aryl, aralkyl, heterocycloalkyl, heteroaryl, or heteroaralkyl;

R$_2$ and R$_4$ are C$_1$-C$_6$alkoxy;

R$_6$ is —C(O)R$_8$, —C(S)R$_8$, —C(O)OR$_8$, —C(O)NR$_8$R$_9$, —C(S)NR$_8$R$_9$, —C(NH)R$_8$, or —S(O$_2$)R$_8$;

R$_7$ is alkyl, aralkyl, or heteroaralkyl;

R$_8$ and R$_9$ each represent independently hydrogen, C$_1$-C$_6$alkyl, heteroalkyl, aryl, heteroaryl, aralkyl, or heteroaralkyl; and n represents independently for each occurrence 0, 1, or 2.

In certain embodiments, Z is —CH$_2$—. In certain embodiments, R$_1$, R$_3$, and R$_5$ each represent independently for each occurrence hydrogen, halogen, hydroxyl, amino, or C$_1$-C$_6$alkyl. In certain embodiments, R$_2$ and R$_4$ are methoxy. In certain embodiments, R$_6$ is C(O)R$_8$, and R$_8$ is C$_1$-C$_6$alkyl. In certain embodiments, R$_7$ is alkyl. In certain embodiments, R$_8$ and R$_9$ each represent independently hydrogen or C$_1$-C$_6$alkyl. In certain embodiments, n is 0.

In certain embodiments, the Nec-3 related compound is

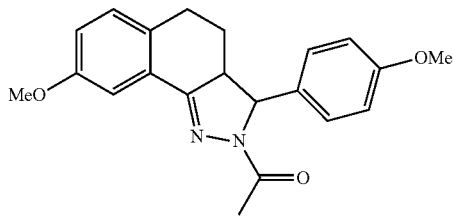 [SMILES: COc1ccc(C2C3CCc4ccc(OC)cc4C3=NN2C(C)=O)cc1]

or a pharmaceutically acceptable salt thereof.

In certain other embodiments, the Nec-3 related compound is

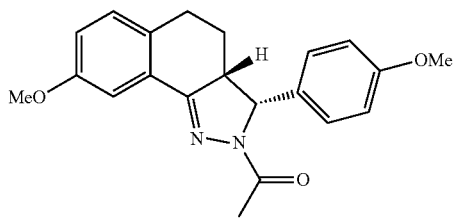 [SMILES: COc1ccc([C@H]2[C@H]3CCc4ccc(OC)cc4C3=NN2C(C)=O)cc1]

or a pharmaceutically acceptable salt thereof.

The Nec-3 related compounds described above can be prepared based on synthetic procedures described in the literature, such as in Degterev et al., (2008) NAT CHEM BIOL 4:313-321; and International Patent Application Publication No. WO 2007/075772, both of which is hereby incorporated by reference.

In certain embodiments, the necrostatin is a Nec-4 related compound of Formula IV:

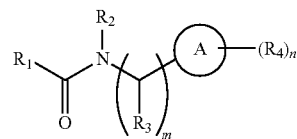

or a pharmaceutically acceptable salt, ester, or prodrug thereof, wherein:

R$_1$ is

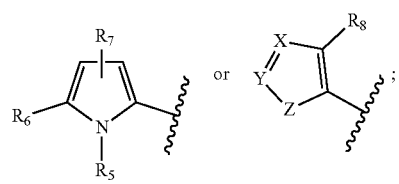

R$_2$ and R$_3$ each represent independently for each occurrence hydrogen or methyl;

R$_4$ represents independently for each occurrence halogen, hydrogen, C$_1$-C$_6$alkyl, C$_2$-C$_6$alkenyl, or C$_2$-C$_4$alkynyl;

R$_5$ is C$_1$-C$_4$alkyl;

R$_6$ is hydrogen, halogen, or —CN;

R$_7$ is hydrogen or C$_1$-C$_4$alkyl;

R$_8$ is C$_1$-C$_6$alkyl, or R$_8$ taken together with R$_9$, when present, forms a carbocyclic ring;

R$_9$ is hydrogen or C$_1$-C$_6$alkyl, or R$_9$ taken together with R$_8$ forms a carbocyclic ring;

R$_{10}$ is hydrogen or C$_1$-C$_6$alkyl;

A is phenylene or a 5-6 membered heteroarylene;

X is N or —C(R$_9$)—;

Y is N or —C(R$_{10}$)—;

Z is S or O; and m and n each represent independently 1, 2, or 3.

In certain embodiments, R$_1$ is

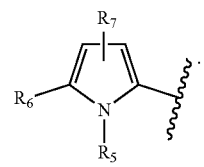

In certain other embodiments, R$_1$ is

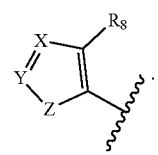

In certain embodiments, R$_2$ is hydrogen. In certain embodiments, R$_3$ is methyl. In certain other embodiments, R$_3$ is hydrogen. In certain embodiments, R$_4$ is halogen, such as fluorine or chlorine. In certain embodiments, R$_4$ is halogen. In certain embodiments, R$_5$ is methyl or ethyl. In certain embodiments, R$_6$ is CN. In certain embodiments, A is phenylene. In certain embodiments, X is N. In certain embodiments, Y is N. In certain embodiments, Z is S. In certain embodiments, A is phenylene. In certain embodiments, $R_1$ is $C_1$-$C_6$alkyl, such as methyl. In certain embodiments, m is 1. In certain embodiments, n is 2.

In certain embodiments, the necrostatin is a Nec-4 related compound of Formula IV-A:

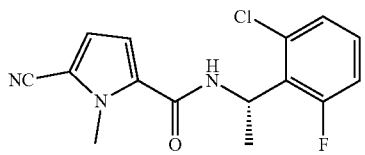 [SMILES: C[C@H](NC(=O)c1ccc(C#N)n1C)c1c(F)cccc1Cl]

or a pharmaceutically acceptable salt thereof.

In certain embodiments, the necrostatin is a Nec-4 related compound of Formula IV-B:

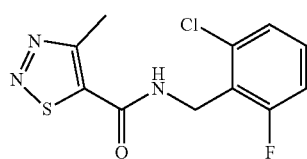 [SMILES: Cc1nnsc1C(=O)NCc1c(F)cccc1Cl]

or a pharmaceutically acceptable salt thereof.

The Nec-4 related compounds described above can be prepared based on synthetic procedures described in the literature, such as in Teng et al., (2007) BIOORG MED CITEM LETT, 17: 6836-6840; and Teng et al., (2008) BIOORG MED CHEM LETT, 18: 3219-3223, both of which are incorporated herein by reference.

In certain embodiments, the necrostatin is a Nec-5 related compound of Formula V:

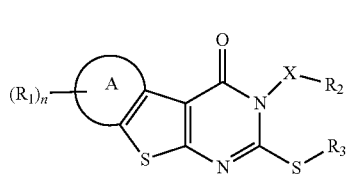

or a pharmaceutically acceptable salt, ester, or prodrug thereof, wherein:

A is a saturated or unsaturated 5-6 membered carbocyclic ring;

X is a bond or $C_1$-$C_4$alkylene;

$R_1$ is $C_1$-$C_6$alkyl, halogen, hydroxyl, $C_1$-$C_6$alkoxyl, —$N(R_4)_2$, —$C(O)R_4$, $CO_2R_4$, or $C(O)N(R_4)_2$;

$R_2$ is

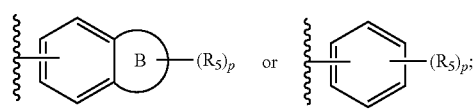

$R_3$ is —$C_1$-$C_6$alkylene-CN, —CN, $C_1$-$C_6$alkyl, or $C_2$-$C_6$alkenyl;

$R_4$ represents independently for each occurrence hydrogen, $C_1$-$C_6$alkyl, aryl, or aralkyl;

$R_5$ represents independently for each occurrence $C_1$-$C_6$alkyl, halogen, hydroxyl, $C_1$-$C_6$alkoxyl, —$N(R_4)_2$, —$C(O)R_4$, $CO_2R_4$, or $C(O)N(R_4)_2$;

B is a 5-6 membered heterocyclic or carbocyclic ring; and n and p each represent independently 0, 1, or 2.

In certain embodiments, X is a bond. In certain embodiments, A is an unsaturated 6-membered carbocyclic ring. In certain embodiments, $R_1$ is $C_1$-$C_6$alkyl, halogen, hydroxyl, or $C_1$-$C_6$alkoxyl. In certain embodiments, $R_2$ is

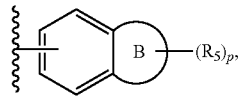

such as

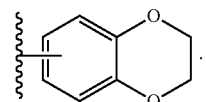

In certain embodiments, $R_3$ is —$C_1$-$C_6$alkylene-CN, such as —$CH_2$—CN. In certain embodiments, $R_4$ represents independently for each occurrence hydrogen or $C_1$-$C_6$alkyl. In certain embodiments, $R_5$ represents independently for each occurrence $C_1$-$C_6$alkyl, halogen, hydroxyl, or $C_1$-$C_6$alkoxyl. In certain embodiments, B is a 5-6 membered heterocyclic ring. In certain embodiments, n is 0. In certain embodiments, p is 0.

In certain embodiments, the necrostatin is a Nec-5 related compound of Formula V-A:

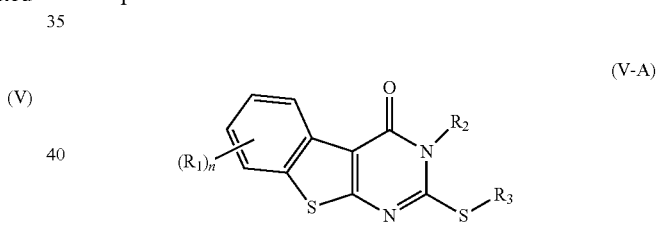

or a pharmaceutically acceptable salt, ester, or prodrug thereof, wherein:

$R_1$ is $C_1$-$C_6$alkyl, halogen, hydroxyl, $C_1$-$C_6$alkoxyl, or —$N(R_4)_2$;

$R_2$ is

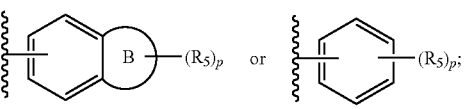

$R_3$ is —$C_1$-$C_6$alkylene-CN;

$R_4$ represents independently for each occurrence hydrogen, $C_1$-$C_6$alkyl, aryl, or aralkyl;

$R_5$ represents independently for each occurrence $C_1$-$C_6$alkyl, halogen, hydroxyl, $C_1$-$C_6$alkoxyl, —$N(R_4)_2$, —$C(O)R_4$, $CO_2R_4$, or $C(O)N(R_4)_2$;

B is a 5-6 membered heterocyclic or carbocyclic ring; and n and p each represent independently 0, 1, or 2.

In certain embodiments, the Nec-5 compound is

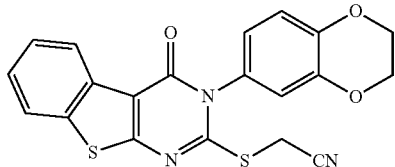 [SMILES: N#CCSc1nc2sc3ccccc3c2c(=O)n1-c1ccc2c(c1)OCCO2]

or a pharmaceutically acceptable salt thereof.

The Nec-5 related compounds described above can be prepared based on synthetic procedures described in the literature, such as in Degterev et al., (2008) NAT CHEM BIOL 4:313-321; and International Patent Application Publication No. WO 2008/045406, both of which is hereby incorporated by reference.

In certain embodiments, the necrostatin is a Nec-7 related compound of Formula VII:

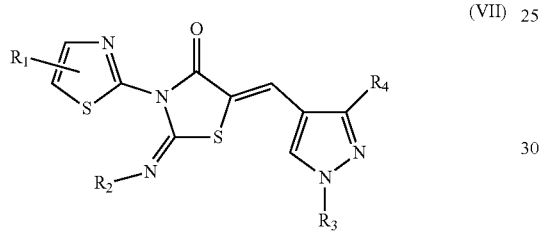

(VII)

or a pharmaceutically acceptable salt, ester, or prodrug thereof, wherein:

$R_1$, $R_2$, and $R_3$ each represent independently hydrogen or $C_1$-$C_4$alkyl;

$R_4$ is

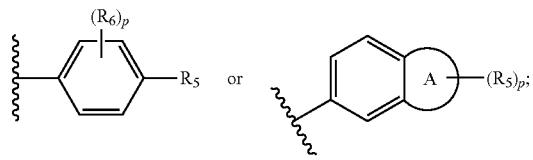

$R_5$ and $R_6$ each represent independently for each occurrence halogen, $C_1$-$C_6$alkyl, hydroxyl, $C_1$-$C_6$alkoxyl, —$N(R_7)_2$, —$NO_2$, —S—$C_1$-$C_6$alkyl, —S-aryl, —$SO_2$—$C_1$-$C_6$alkyl, —$SO_2$— aryl, —$C(O)R_7$, —$CO_2R_7$, —$C(O)N(R_7)_2$, heterocycloalkyl, aryl, or heteroaryl;

$R_7$ represents independently for each occurrence hydrogen, $C_1$-$C_6$alkyl, aryl, or aralkyl; or two occurrences of $R_7$ attached to the same nitrogen atom are taken together with the nitrogen atom to which they are attached to form a 3-7 membered heterocyclic ring;

A is a 5-6 membered heterocyclic ring; and p is 0, 1, or 2.

In certain embodiments, $R_1$ is hydrogen. In certain embodiments, $R_2$ is hydrogen. In certain embodiments, $R_3$ is hydrogen. In certain embodiments, $R_4$ is

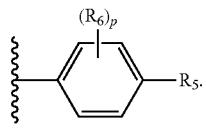

In certain embodiments, $R_5$ is halogen, $C_1$-$C_6$alkyl, hydroxyl, $C_1$-$C_6$alkoxyl, or —$N(R_7)_2$. In certain other embodiments, $R_5$ is halogen, such as fluorine or chlorine. In certain embodiments, p is 0. In certain other embodiments, $R_4$ is

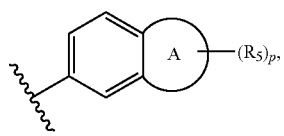

such as

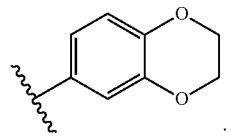 [SMILES: *c1ccc2c(c1)OCCO2]

In certain embodiments, the Nec-7 related compound is

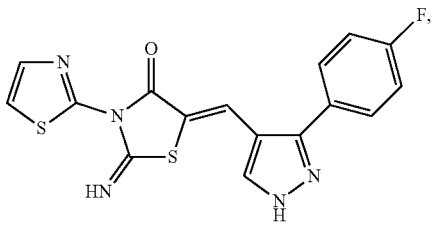 [SMILES: N=C1S/C(=C\c2c[nH]nc2-c2ccc(F)cc2)C(=O)N1c1nccs1]

or a pharmaceutically acceptable salt thereof.

The Nec-7 related compounds described above can be prepared based on synthetic procedures described in the literature, such as in Zheng et al., in BIOORG MED CITEM LETT, 2008, vol. 18, 4932-4935, which is incorporated herein by reference.

In certain embodiments, the necrostatin is a Nec-7 related compound of Formula VIII:

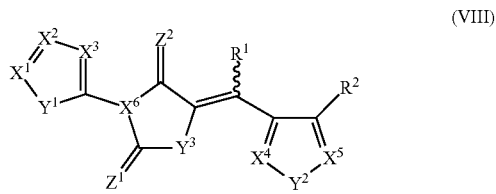

(VIII)

or a pharmaceutically acceptable salt, ester, or prodrug thereof, wherein:

each $X^1$, $X^2$, $X^3$, $X^4$, $X^5$, and $X^6$ is selected, independently, from N or $CR^{X1}$;

each $Y^1$, $Y^2$, and $Y^3$ is selected, independently, from O, S, $NR^{Y1}$, or $CR^{Y2}R^{Y3}$;

each $Z^1$ and $Z^2$ is selected, independently, from O, S, or $NR^{Z1}$;

each $R^{Y1}$ and $R^{Z1}$ is selected, independently, from H, optionally substituted $C_{1-6}$alkyl, optionally substituted $C_{2-6}$alkenyl, optionally substituted $C_{2-6}$alkynyl, optionally substituted cycloalkyl, optionally substituted heterocyclyl, optionally substituted aryl, optionally substituted heteroaryl, —C(=O)$R^{5A}$, —C(=O)O$R^{5A}$, or —C(=O)N$R^{5A}R^{6A}$;

each $R^{X1}$, $R^{Y2}$, and $R^{Y3}$ is selected, independently, from H, halogen, CN, NC, $NO_2$, $N_3$, $OR^3$, $SR^3$, $NR^3R^4$, —C(=O)$R^{5A}$, —C(=O)O$R^{5A}$, —C(=O)N$R^{5A}R^{6A}$, —S(=O)$R^{5A}$, —S(=O)$_2R^{5A}$, —S(=O)$_2OR^{5A}$, —S(=O)$_2NR^{5A}R^{6A}$, optionally substituted $C_{1-6}$alkyl, optionally substituted $C_{2-6}$alkenyl, optionally substituted $C_{2-6}$alkynyl, optionally substituted cycloalkyl, optionally substituted heterocyclyl, optionally substituted aryl, or optionally substituted heteroaryl;

each $R^1$, $R^2R^{5A}$, $R^{5B}$, $R^{6A}$, and $R^{6B}$ is selected from H, optionally substituted $C_{1-6}$ alkyl, optionally substituted $C_{2-6}$alkenyl, optionally substituted $C_{2-6}$alkynyl, optionally substituted cycloalkyl, optionally substituted heterocyclyl, optionally substituted aryl, or optionally substituted heteroaryl; or $R^{5A}$ and $R^{6A}$, or $R^{5B}$ and $R^{6B}$ combine to form a heterocyclyl; and each $R^3$ and $R^4$ is selected from H, optionally substituted $C_{1-6}$ alkyl, optionally substituted cycloalkyl, optionally substituted heterocyclyl, optionally substituted aryl, optionally substituted heteroaryl, —C(=O)$R^{5B}$, —C(=S)$R^{5B}$, —C(=N$R^{6B}$)$R^{5B}$, —C(=O)O$R^{5B}$, —C(=O)N$R^{5B}R^{6B}$, —S(=O)$R^{5B}$, —S(=O)$_2R^{5B}$, —S(=O)$_2OR^{5B}$, or —S(=O)$^2NR^{5B}R^{6B}$. In certain embodiments, when $R^1$ is H, $X^1$, $X^2$, and $X^4$ are each CH, $X^3$, $X^5$, and $X^6$ are each N, $Y^1$ and $Y^3$ are each S, $Y^2$ is NH, $Z^1$ is NH, and $Z^2$ is O, then $R^2$ is not 4-fluorophenyl.

In certain embodiments, the necrostatin is a Nec-7 related compound of Formula VIII-A:

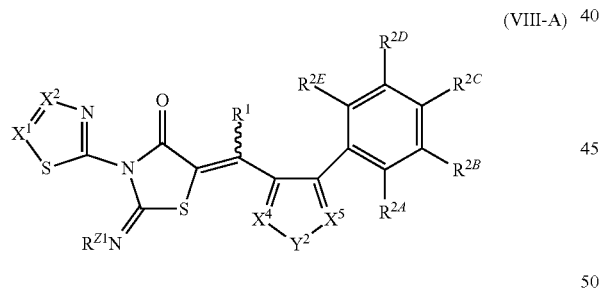

(VIII-A)

or a pharmaceutically acceptable salt, ester, or prodrug thereof, wherein:

$X^1$, $X^2$, $X^4$, $X^5$, $R^1$, $Y^2$, and $R^{Z1}$ are as defined for Formula (VIII);

each $R^{2A}$, $R^{2B}$, $R^{2C}$, $R^{2D}$, and $R^{2E}$ is selected, independently, from H, halogen, optionally substituted $C_{1-6}$ alkyl, optionally substituted $C_{2-6}$ alkenyl, optionally substituted $C_{2-6}$ alkynyl, optionally substituted cycloalkyl, optionally substituted heterocyclyl, optionally substituted aryl, optionally substituted heteroaryl, CN, NC, $NO_2$, $N_3$, $OR^7$, $SR^7$, S(=O)$R^{12}$, S(=O)$_2R^{12}$, S(=O)O$R^{12}$, S(=O)$_2OR^{12}$, $NR^7R^8$, C(=O)$R^{12}$, C(=O)O$R^{12}$, C(=O)N$R^{12}R^{13}$, C(=S)$R^{12}$, C(=S)O$R^{12}$, C(=S)N$R^{12}R^{13}$, C(=N$R^9$)$R^{12}$, C(=N$R^9$)O$R^{12}$, or C(=N$R^9$)N$R^{12}R^{13}$, or $R^{2A}$ and $R^{2B}$, $R^{2B}$ and $R^{2C}$, $R^{2C}$ and $R^{2D}$, or $R^{2D}$ and $R^{2E}$ combine to form an optionally substituted cycloalkyl or an optionally substituted heterocyclyl;

each $R^7$, $R^8$, and $R^9$ is selected, independently, from H, optionally substituted $C_{14}$ alkyl, optionally substituted cycloalkyl, optionally substituted heterocyclyl, optionally substituted aryl, optionally substituted heteroaryl, S(=O)$R^{10}$, S(=O)$_2R^{10}$, C(=O)$R^{10}$, C(=O)O$R^{10}$, C(=O)N$R^{10}R^{11}$, C(=S)$R^{10}$, C(=S)O$R^{10}$, C(=S)N$R^{10}R^{11}$, C(=N$R^{14}$)$R^{10}$, C(=N$R^{14}$)O$R^{10}$, or C(=N$R^{14}$)N$R^{10}R^{11}$, or $R^7$ and $R^8$ combine to form an optionally substituted heterocyclyl; and each $R^{10}$, $R^{11}$, $R^{12}$, $R^{13}$, and $R^{14}$ is selected, independently, from H, optionally substituted $C_{1-6}$alkyl, optionally substituted $C_{2-6}$alkenyl, optionally substituted $C_{2-6}$alkynyl, optionally substituted cycloalkyl, optionally substituted heterocyclyl, optionally substituted aryl, or optionally substituted heteroaryl, or $R^{10}$ and $R^{11}$ or $R^{12}$ and $R^{13}$ combine to form an optionally substituted heterocyclyl.

In certain embodiments, each $R^{2A}$, $R^{2B}$, $R^{2C}$, $R^{2D}$, and $R^{2E}$ is selected, independently, from H, halogen, $C_{1-6}$ alkyl, $C_{2-6}$ alkenyl, $C_{2-6}$ alkynyl, cycloalkyl, heterocyclyl, aryl, or heteroaryl.

In certain embodiments, the necrostatin is a Nec-7 related compound selected from:

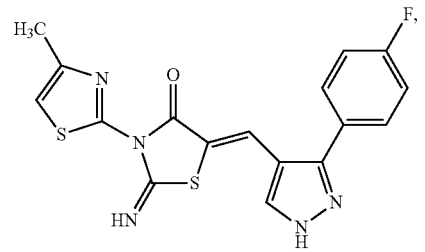

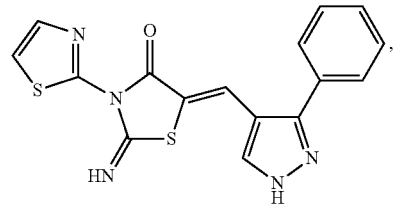

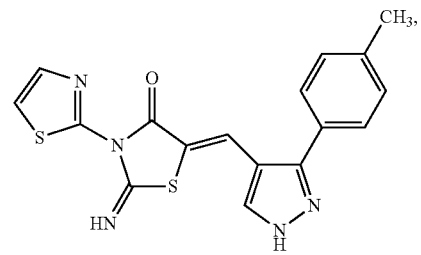

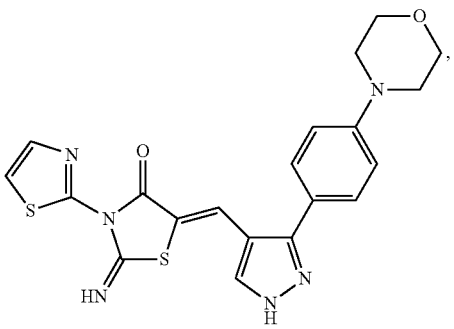

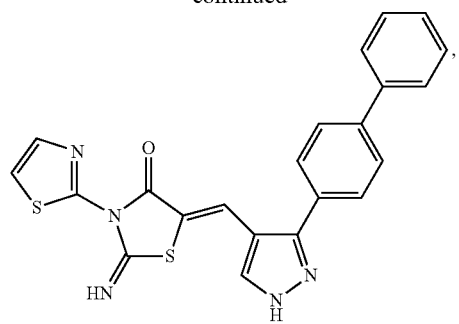
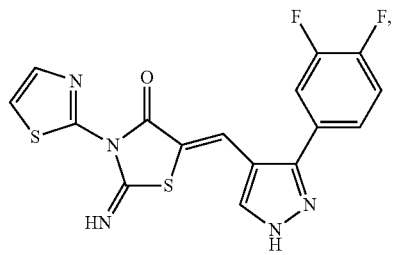
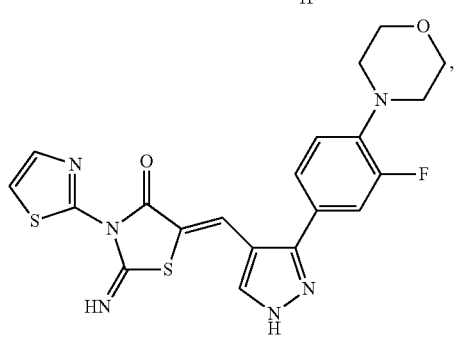
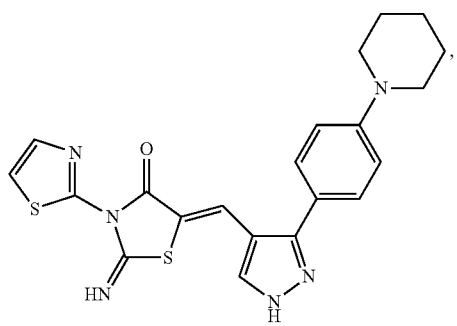
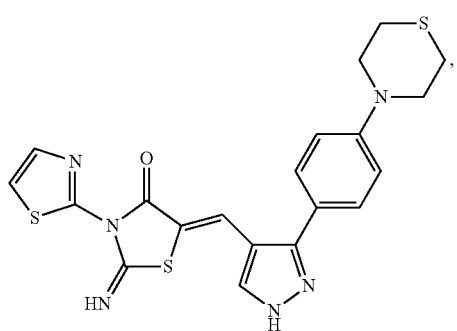
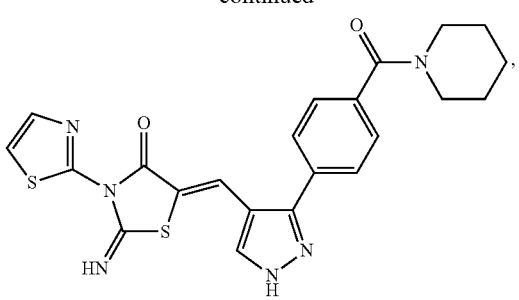
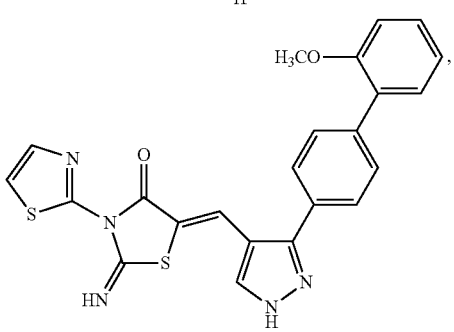
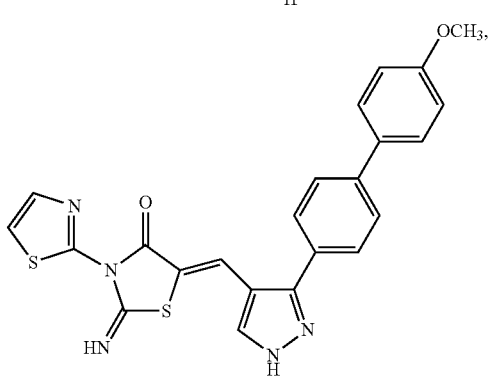
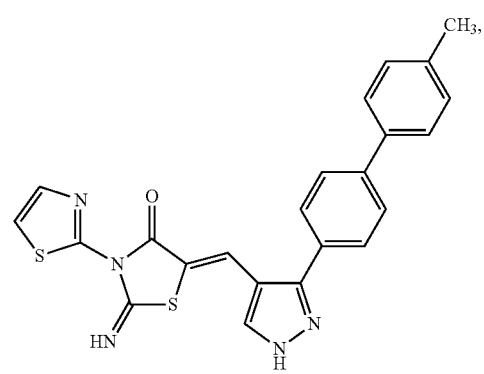
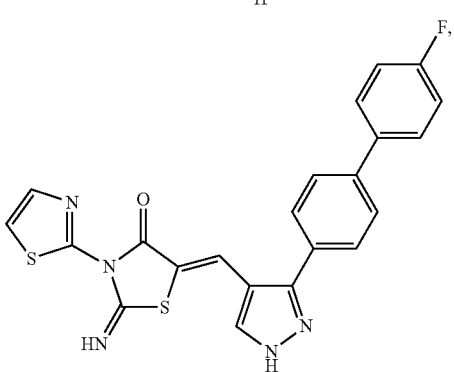

-continued

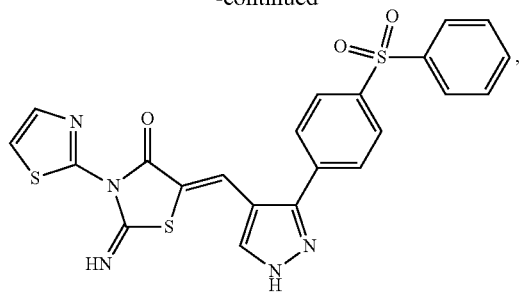

and pharmaceutically acceptable salts thereof.

The Nec-7 related compounds described above can be prepared based on synthetic procedures described in the literature, such as International Patent Application Publication No. WO 2010/075290, which is hereby incorporated by reference.

In certain embodiments, the necrostatin is a Nec-4 related compound of Formula IX:

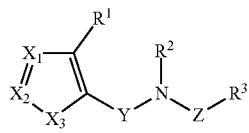

(IX)

or a pharmaceutically acceptable salt, ester, or prodrug thereof, wherein:

$X_1$ and $X_2$ are, independently, N or $CR^4$;
$X_3$ is selected from O, S, $NR^5$, or —$(CR^5)_2$;
Y is selected from C(O) or $CH_2$; and
is $(CR^6R^7)_n$;
$R_1$ is selected from H, halogen, optionally substituted $C_{1-6}$alkyl, or optionally substituted $C_{1-6}$cycloalkyl, or optionally substituted aryl;
$R^2$ is selected from H or optionally substituted $C_{1-6}$alkyl;
$R^3$ is optionally substituted aryl;
each $R^4$ is selected from H, halogen, carboxamido, nitro, cyano, optionally substituted $C_{1-6}$alkyl, or optionally substituted aryl;
$R^5$ is selected from H, halogen, optionally substituted $C_{1-6}$alkyl, or optionally substituted aryl;
each $R^6$ and $R^7$ is, independently, selected from H, optionally substituted $C_{1-6}$alkyl, or aryl; and
n is 0, 1, 2, or 3. In certain embodiments, when $X_1$ and $X_2$ are N, $X_3$ is S, Y is C(O), Z is $CH_2$, $R^2$ is H, and $R^3$ is 2-chloro-6-fluoro-phenyl, then $R^1$ is not methyl.

In certain embodiments, the necrostatin is a Nec-4 related compound of Formula IX-A:

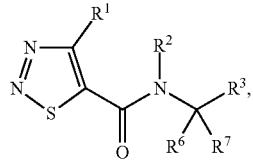

(IX-A)

or a pharmaceutically acceptable salt, ester, or prodrug thereof, wherein:

$R^1$, $R^2$, $R^3$, $R^6$ and $R^7$ are as defined in Formula (IX).

In certain embodiments, the necrostatin is a Nec-4 related compound selected from:

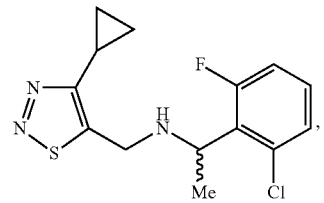

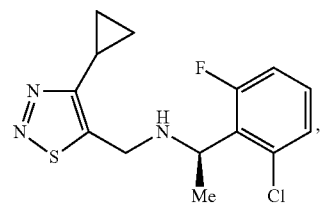

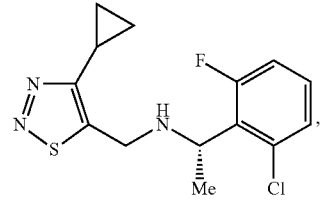

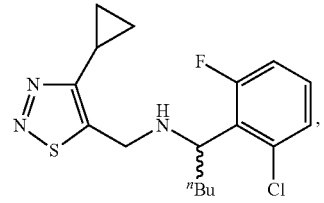

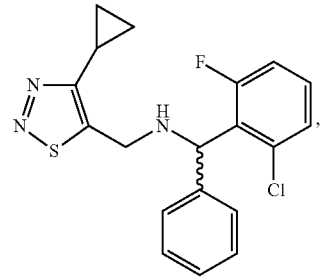

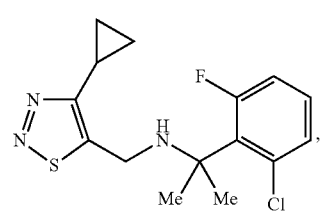

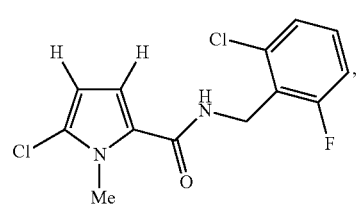

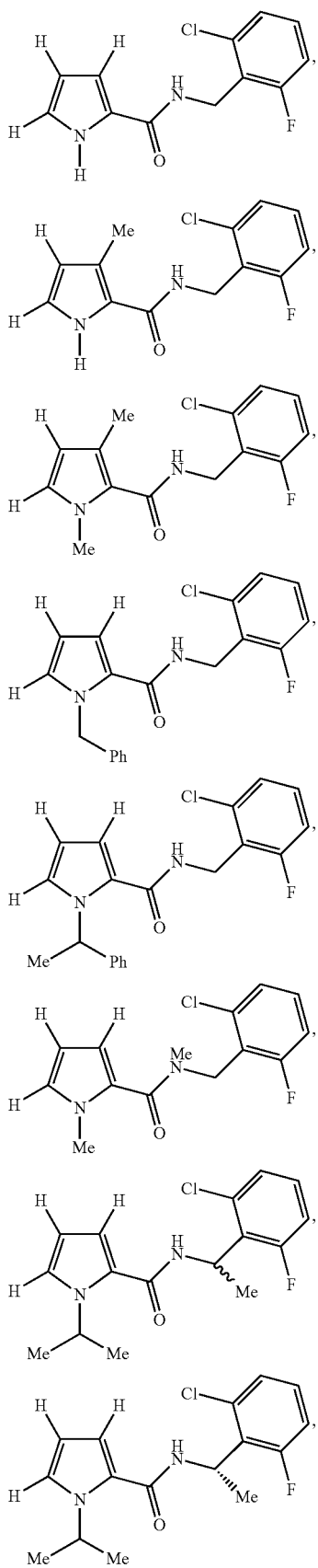

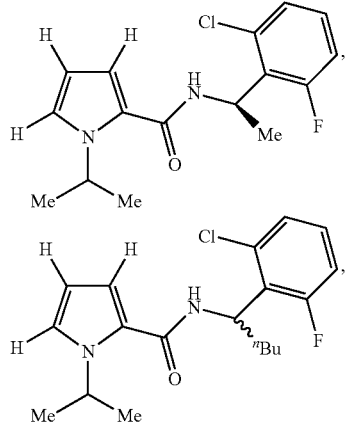

and pharmaceutically acceptable salts thereof.

The Nec-4 related compounds described above can be prepared based on synthetic procedures described in the literature, such as U.S. Patent Application Publication No. 2009/0099242, which is hereby incorporated by reference.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 10 or fewer carbon atoms in its backbone (e.g., $C_1$-$C_{10}$ for straight chain, $C_3$-$C_{10}$ for branched chain), and alternatively, 5, 4, 3, 2 or 1 carbon atoms in its backbone. Likewise, cycloalkyls have from about 3 to about 10 carbon atoms in their ring structure, and alternatively about 5, 6 or 7 carbons in the ring structure. Exemplary alkyl groups include methyl, ethyl, n-propyl, isopropyl, n-butyl, sec-butyl, isobutyl, tert-butyl, cyclopropyl, and cyclobutyl.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, or —O-alkynyl. The term "alkylene" refers to a diradical of an alkyl group. An exemplary alkylene group is —$CH_2CH_2$—.

The term "aralkyl" refers to an alkyl group substituted with an aryl group.

The term "heteroaralkyl" refers to an alkyl group substituted with a heteroaryl group.

The term "alkenyl" refers to an unsaturated straight or branched hydrocarbon having at least one carbon-carbon double bond, such as a straight or branched group of 2-12, 2-10, or 2-6 carbon atoms, referred to herein as $C_2$-$C_2$alkenyl, $C_2$-$C_{10}$alkenyl, and $C_2$-$C_6$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, etc.

The term "alkynyl" as used herein refers to an unsaturated straight or branched hydrocarbon having at least one carbon-carbon triple bond, such as a straight or branched group of 2-12, 2-8, or 2-6 carbon atoms, referred to herein as $C_2$-$C_{12}$alkynyl, $C_2$-$C_8$alkynyl, and $C_2$-$C_6$alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl, etc.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, heteroaryl, —CF$_3$, —CN, or the like. The term "aryl" also includes polycyclic ring systems having two or more carbocyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls.

In certain embodiments, the aromatic group is not substituted, i.e., it is unsubstituted.

The term "phenylene" refers to a multivalent radical (e.g., a divalent or trivalent radical) of benzene. To illustrate, a divalent valent radical of benzene is illustrated by the formula

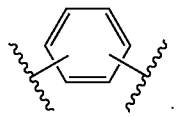

The terms "heterocyclyl" or "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. Heterocycles may also be mono-, bi-, or other multi-cyclic ring systems. A heterocycle may be fused to one or more aryl, partially unsaturated, or saturated rings. Heterocyclyl groups include, for example, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isoxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. Unless specified otherwise, the heterocyclic ring is optionally substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. In certain embodiments, the heterocyclyl group is not substituted, i.e., it is unsubstituted.

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl, —CF$_3$, —CN, or the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls.

The term "heteroarylene" refers to a multi-valent (e.g., di-valent or trivalent) aromatic group that comprises at least one ring heteroatom. An exemplary "heteroarylene" is pyridnylene, which is a multi-valent radical of pyridine. For example, a divalent radical of pyridine is illustrated by the formula

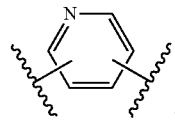

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "amine" and "amino" are art-recognized and refer to both unsubstituted and substituted amines, e.g., a moiety that may be represented by the general formula:

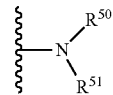

wherein $R^{50}$ and $R^{51}$ each independently represent hydrogen, alkyl, alkenyl, or —(CH$_2$)$_m$—R$^{61}$; or $R^{50}$ and $R^{51}$, taken together with the N atom to which they are attached complete a heterocycle having from 4 to 8 atoms in the ring structure; wherein $R^{61}$ is aryl, cycloalkyl, cycloalkenyl, a heterocycle or a polycycle; and m is zero or an integer in the range of 1 to 8. In certain embodiments, $R^{50}$ and $R^{51}$ each independently represent hydrogen or alkyl.

The term "amide" or "amido" as used herein refers to a radical of the form —R$_a$C(O)N(R$_b$)—, —R$_a$C(O)N(R$_b$)R$_c$—, —C(O)NR$_b$R$_c$, or —C(O)NH$_2$, wherein R$_a$, R$_b$ and R$_c$ are each independently selected from alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, and nitro. The amide can be attached to another group through the carbon, the nitrogen, R$_b$, R$_c$, or R$_a$. The amide also may be cyclic, for example R$_b$ and R$_c$, R$_a$ and R$_b$, or R$_a$ and R$_c$ may be joined to form a 3- to 12-membered ring, such as a 3- to 10-membered ring or a 5- to 6-membered ring. The term "carboxamido" refers to the structure —C(O)NR$_b$R$_c$.

The term "sulfonamide" or "sulfonamido" as used herein refers to a radical having the structure —N(R$_r$)—S(O)$_2$—R$_s$— or —S(O)$_2$—N(R$_r$)R$_s$, where R$_r$, and R$_s$ can be, for example, hydrogen, alkyl, aryl, cycloalkyl, and heterocyclyl. Exemplary sulfonamides include alkylsulfonamides (e.g., where $R_s$ is alkyl), arylsulfonamides (e.g., where $R_s$ is aryl), cycloalkyl sulfonamides (e.g., where $R_s$ is cycloalkyl), and heterocyclyl sulfonamides (e.g., where $R_s$ is heterocyclyl), etc.

The term "sulfonyl" as used herein refers to a radical having the structure $R_u SO_2$—, where $R_u$ can be alkyl, aryl, cycloalkyl, and heterocyclyl, e.g., alkylsulfonyl. The term "alkylsulfonyl" as used herein refers to an alkyl group attached to a sulfonyl group.

The symbol "⁓" indicates a point of attachment.

Unless specified otherwise, the term "optionally substituted" as used herein means that the specified group may be substituted at one, two or more positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, heteroaryl, —CF$_3$, —CN, or the like.

As used herein, the term "therapeutically effective amount" is understood to mean the amount of an active ingredient, for example, a necrostatin (e.g., necrostatin-1 or necrostatin-4) and/or a pan-caspase inhibitor (e.g., Z-VAD or IDN-6556) that is sufficient to reduce, minimize or eliminate the death of retinal ganglion cells associated with certain ocular conditions described herein. The compounds of the invention are administered in amounts effective at, e.g., reducing the death of retinal ganglion cells, increasing efficacy compared to monotherapy with either drug alone, preserving or improving vision, preserving or improving visual function, preventing vision loss, and/or promoting axon regeneration. It is understood that preserving vision or visual function, includes stabilizing vision or visual function and/or slowing the decline of vision or visual function prior to treatment.

As used herein, "pharmaceutically acceptable" or "pharmacologically acceptable" mean molecular entities and compositions that do not produce an adverse, allergic or other untoward reaction when administered to an animal, or to a human, as appropriate. The term, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Disclosed herein is a method of preserving the visual function of an eye of a subject with ocular conditions, wherein a symptom of the ocular condition is the loss of retinal ganglion cell viability in the retina of the eye with the conditions. The method comprises (a) administering to the eye of the subject an effective amount of a necrosis inhibitor (e.g., a necrostatin, e.g., necrostatin-1 or necrostatin-4) and an effective amount of an apoptosis inhibitor thereby preserving the viability of the retinal ganglion cells disposed within the retina of the eye, and (b) measuring the visual function (e.g., visual acuity) of the eye after the administration of the necrosis inhibitor and the apoptosis inhibitor. After administration of the necrosis inhibitor and the apoptosis inhibitor the visual function of the eye may be preserved or improved relative to the visual function of the eye prior to administration of the necrosis inhibitor and the apoptosis inhibitor. Further, after the administration of the necrosis inhibitor and the apoptosis inhibitor, the preserved retinal ganglion cell is capable of supporting axonal regeneration.

Further disclosed is a method of preserving the visual function of an eye of a subject with ocular condition, wherein a symptom of the ocular condition is the loss of retinal ganglion cell viability in the retina of the eye with the condition. The method comprises reducing the production and/or activity of a RIP-1 kinase and/or a RIP-3 kinase in the eye to preserve the viability of the retinal ganglion cells disposed within the eye. The reduction in the production and/or activity of the RIP-1 kinase and/or RIP-3 kinase may be achieved by administering an effective amount of a necrosis inhibitor (e.g., RIPK inhibitor, e.g., a necrostatin). The reduction in the production and/or activity of the RIP-1 kinase and/or RIP-3 kinase may be direct (e.g., the necrosis inhibitor modulates the production and/or activity the RIP-1 kinase and/or RIP-3 kinase directly) or indirect (e.g., the necrosis inhibitor acts upstream of the RIP-1 kinase and/or RIP-3 kinase but the administration of which indirectly modulates the production and/or activity of the RIP-1 kinase and/or RIP-3 kinase). Visual function of the eye may be measured before and/or after the administration of the necrosis inhibitor that directly or indirectly reduces the production and/or activity of a RIP-1 kinase and/or RIP-3 kinase. After administration of the necrosis inhibitor the visual function of the eye may be preserved or improved relative to the visual function of the eye prior to administration of the necrosis inhibitor.

In each of the foregoing methods, the ocular condition, wherein a symptom of the condition is the loss of retinal ganglion cell viability in the retina of the eye, includes but is not limited to glaucoma, optic nerve injury, optic neuritis, optic neuropathies, diabetic retinopathy, central retinal artery occlusion, and central retinal vein occulusion. It is contemplated that the forgoing methods may be used for the treatment of optic neuropathies such as ischemic optic neuropathy (e.g., arteritic or non-arteritic anterior ischemic neuropathy and posterior ischemic optic neuropathy), compressive optic neuropathy, infiltrative optic neuropathy, traumatic optic neuropathy, mitochondrial optic neuropathy (e.g., Leber's optic neuropathy), nutritional optic neuropathy, toxic optic neuropathy, and hereditary optic neuropathy (e.g., Leber's optic neuropathy, Dominant Optic Atrophy, Behr's syndrome).

Also disclosed is a method of preserving the visual function of an eye of a subject with an ocular condition selected from the group consisting of glaucoma, optic nerve injury, optic neuropathies, diabetic retinopathy, central retinal artery occlusion, and central retinal vein occulusion. The method comprises administering to the eye of the subject an effective amount of a necrostatin and an effective amount of an apoptosis inhibitor thereby preserving the viability of the retinal ganglion cells disposed within the retina of the eye and the visual function of the eye.

In another aspect, disclosed herein is a method of preserving the viability of retinal ganglion cells disposed within a retina of a mammalian eye affected by, for example, glaucoma, optic nerve injury, optic neuritis, optic neuropathies, diabetic retinopathy, central retinal artery occlusion, and central retinal vein occulusion. The method comprises administering a necrosis inhibitor and/or an apoptosis inhibitor to the eye in which a region of the retina has been affected in amounts sufficient to preserve the viability of retinal ganglion cells disposed within the region of the affected retina. The preserved retinal ganglion cell is capable of supporting axonal regeneration.

Also disclosed is a method for promoting axon regeneration in a eye of a subject with an ocular condition, wherein a symptom of the ocular condition is the loss of retinal ganglion cell viability in the retina of the eye with the condition. The method comprises administering to the eye of the subject an effective amount of a necrostatin and an effective amount of an apoptosis inhibitor thereby promoting axon regeneration of the retinal ganglion cell within the retina of the eye.

In each of the foregoing embodiments, it is understood that the methods and compositions described herein can be used to preserve the viability and/or promote axon regeneration of retinal ganglion cells during treatment of the underlying conditions including, but not limited to, glaucoma, optic nerve injury, optic neuritis, optic neuropathies, diabetic retinopathy, central retinal artery occlusion, and central retinal vein occulusion.

Unless specified, the necrostatin can be administered to give a final concentration of greater than about 5 µM, for example, in the range of about 5 µM to about 1000 µM. In certain embodiments, the necrostatin can be administered in an amount sufficient to give a final concentration of necrostatin in the eye of greater than about 10 µM. In another embodiment, the necrostatin can be administered in an amount sufficient to give a final concentration of necrostatin in the eye of greater than about 50 µM. In another embodiment, the necrostatin can be administered in an amount sufficient to give a final concentration of necrostatin in the eye of greater than about 100 µM. For example, the necrostatin may be administered in an amount sufficient to give a final concentration of necrostatin in the eye in the range from about 5 µM to about 1000 µM, 10 µM to about 1000 µM, 50 µM to about 1000 µM, 80 µM to about 1000 µM, about 100 µM to about 1000 µM, about 150 µM to about 1000 µM, from about 200 µM to about 800 µM, or from about 200 µM to about 600 µM. In certain embodiments, the necrostatin is administered in an amount sufficient to give a final concentration of necrostatin in the eye of about 400 µM.

The apoptosis inhibitor, for example, the pan-caspase inhibitor, can be administered in an amount sufficient to give a final concentration of the inhibitor in the eye of greater than about 3 µM, for example, in the range of about 3 µM to about 500 µM. In certain embodiments, the necrostatin can be administered in an amount sufficient to give a final concentration of necrostatin in the eye of greater than about 3 µM. In another embodiment, the necrostatin can be administered in an amount sufficient to give a final concentration of necrostatin in the eye of greater than about 30 µM. In a further embodiment, the necrostatin can be administered in an amount sufficient to give a final concentration of necrostatin in the eye of greater than about 50 µM. In yet a further embodiment, the necrostatin can be administered in an amount sufficient to give a final concentration of necrostatin in the eye of greater than about 100 µM. For example, the apoptosis inhibitor can be administered in an amount sufficient to give a final concentration of the inhibitor in the eye in the range from about 3 µM to about 500 µM, from about 80 µM to about 500 µM, 100 µM to about 500 µM, 125 µM to about 500 µM, 150 µM to about 500 µM or from about 200 µM to about 400 µM. In certain embodiments, apoptosis inhibitor (e.g., the pan-caspase inhibitor) is administered in an amount sufficient to give a final concentration of the inhibitor in the eye of about 300 µM.

In view of the fact that the volume of the eye in a given subject is known (for example, typical human eye contains 4 to 6 mL of fluid (humor), it is possible to calculate the dosage of the necrostatin and/or the pan-caspase inhibitor to be administered to give the therapeutically effective concentrations noted above. For example, from about 0.035 mg to about 2 mg of necrostatin-1 and from about 0.05 mg to about 1.5 mg of a pan-caspase inhibitor can be administered to achieve the concentrations noted above.

In certain embodiments, from about 0.025 mg to about 4 mg, from about 0.035 mg to about 2 mg, from about 0.05 mg to about 2 mg, from about 0.1 mg to about 2 mg, from about 0.2 mg to about 1 mg, or from about 0.2 mg to about 0.8 mg of the necrosis inhibitor (e.g., a necrostatin) can be administered locally to the eye of a mammal. In one embodiment, 0.5 mg of necrostatin is administered locally to the eye of a mammal. In certain other embodiments, from about 0.05 mg to about 2 mg, from about 0.2 mg to about 2 mg, from about 0.05 mg to about 1.5 mg, from about 0.15 mg to about 1.5 mg, from about 0.4 mg to about 1 mg, or from about 0.5 mg to about 0.8 mg of an apoptosis inhibitor (e.g., a pan-caspase inhibitor, e.g., Z-VAD) can be administered locally to the eye of a mammal. In certain embodiments, about 0.7 mg of a pan-caspase inhibitor, e.g., Z-VAD, is administered locally to the eye of a mammal.

It is understood that the invention relates to the use of a necrosis inhibitor, either alone or in combination with an apoptosis inhibitor, for preserving the viability and/or promoting the axon regeneration of retinal ganglion cells for the treatment of the ocular disorder. The invention also relates to the use of an apoptois inhibitor, either alone or in combination with a necrosis inhibitor, for preserving the viability and/or promoting the axon regeneration of retinal ganglion cells for the treatment of the ocular disorder.

In certain aspects, one or more of a necrosis inhibitor, one or more of an apoptosis inhibitor, or one or more of a necrosis inhibitor and one or more of an apoptosis inhibitor can be administered to the eye in which a region of the retina has been affected in amounts sufficient to preserve the viability and/or promote axon regeneration of retinal ganglion cells disposed within the region of the affected retina.

In certain embodiments, the necrosis inhibitor is a necrostatin, for example, necrostatin-1, a necrostatin-2, a necrostatin-4, a necrostatin-5, and a necrostatin-7. One or more of these necrosis inhibitors can be administered with one or more of the apoptosis inhibitors (e.g., IDN-6556) listed below. Furthermore, it is contemplated that one or more of the necrostatins shown by Formula I, I-A, I-B, I-C, I-D, I-E, I-F, I-G, II, II-A, III, IV, IV-A, IV-B, V, V-A, VII, VIII, VIII-A, IX, or IX-A can be administered with one or more of the apoptosis inhibitors (e.g., IDN-6556 or IDN-6734) listed below.

In certain embodiment, the necrosis inhibitor reduces the production and/or activity of a RIP-1 kinase and/or a RIP-3 kinase. RIP kinase inhibitors (e.g., RIP-1 kinase and/or RIP-3 kinase inhibitors) as disclosed herein may further include RNAs, including small inhibitory RNAs (siRNAs) and short hairpin RNAs (shRNAs). Methods for designing and synthesizing siRNAs and shRNAs are well known in the art. Exemplary RIP-1 kinase inhibitors include, for example, a pSIREN-RIP-1 shRNA construct which targets RIP-1 kinase as disclosed in Kaiser et al., (2008) JOURNAL OF IMMUNOLOGY 181:6427-6434. Exemplary RIP-3 kinase inhibitors include, for example, sc-61482-SH and sc-135170 available from Santa Cruz Biotechnology. In another example, RIP kinase inhibitors (e.g., RIP-1 kinase and/or RIP-3 kinase inhibitors) as disclosed herein may include inhibitor of apoptosis proteins (IAPs), active fragments thereof, and nucleic acids encoding the same. It is well established that IAPs inhibit RIP-1 kinase by functioning as a E3 ligase for RIP-1 kinase (see, for example, Vanlangenakker et al., (2010)).

In certain embodiments, the one or more apoptosis inhibitors may include a pan-caspase inhibitor. The pan-caspase inhibitor can be Z-VAD (i.e., Z-Val-Ala-Asp(OMe)-CH$_2$F*), IDN-6556 available from Conatus Pharmaceuticals (i.e., (3-{2-[(2-tert-butyl-phenylaminooxalyl)-amino]-propionylamino}-4-oxo-5-(2,3,5,6-tetrafluoro-phenoxy)-pentanoic acid) (3-{2-[(2-tert-butyl-phenylaminooxalyl)-amino]-propionylamino}-4-oxo-5-(2,3,5,6-tetrafluoro-phenoxy)-pentanoic acid), IDN-6734 available from Conatus Pharmaceuticals, VX-799 available from Vertex Pharmaceuticals, MX1013 and MX2060 derivatives available from Maxim Pharmaceuticals, M-920 available from Merck-Frosst, small-molecule compounds available from Gemin X Pharmaceuticals, RGD peptides from Merck-Frost and Maxim Pharmaceuticals, or any other known pan-caspase inhibitor.

Alternatively, the pan-caspase inhibitor can be a cocktail of caspase inhibitors including two or more specific caspase inhibitors (e.g., synthetic caspase inhibitors) such as a caspase 1 inhibitor, a caspase 2 inhibitor, a caspase 3 inhibitor, a caspase 4 inhibitor, a caspase 5 inhibitor, a caspase 6 inhibitor, a caspase 7 inhibitor, a caspase 8 inhibitor, and a caspase 9 inhibitor. It is contemplated that one or more of the pan-caspase inhibitors may be used in combination with one or more necrostatins (e.g., necrostain-1 and/or necrostatin-4).

Exemplary synthetic caspase 1 inhibitors, include, for example, Ac-N-Me-Tyr-Val-Ala-Asp-aldehyde (SEQ ID NO: 7), Ac-Trp-Glu-His-Asp-aldehyde (SEQ ID NO: 8), Ac-Tyr-N-Me-Val-Ala-N-Me-Asp-aldehyde (SEQ ID NO: 9), Ac-Tyr-Val-Ala-Asp-Aldehyde (SEQ ID NO: 10), Ac-Tyr-Val-Ala-Asp-chloromethylketone (SEQ ID NO: 11), Ac-Tyr-Val-Ala-Asp-2,6-dimethylbenzoyloxymethylketone (SEQ ID NO: 12), Ac-Tyr-Val-Ala-Asp(OtBu)-aldehyde-dimethyl acetol (SEQ ID NO: 13), Ac-Tyr-Val-Lys-Asp-aldehyde (SEQ ID NO: 14), Ac-Tyr-Val-Lys(biotinyl)-Asp-2,6-dimethylbenzoyloxymethylketone (SEQ ID NO: 15), biotinyl-Tyr-Val-Ala-Asp-chloromethylketone (SEQ ID NO: 16), Boc-Asp(OBzl)-chloromethylketone, ethoxycarbonyl-Ala-Tyr-Val-Ala-Asp-aldehyde (pseudo acid) (SEQ ID NO: 17), Z-Asp-2,6-dichlorobenzoyloxymethylketone, Z-Asp(OlBu)-bromomethylketone, Z-Tyr-Val-Ala-Asp-chloromethylketone (SEQ ID NO: 18), Z-Tyr-Val-Ala-DL-Asp-fluoromethlyketone (SEQ ID NO: 19), Z-Val-Ala-DL-Asp-fluoromethylketone, and Z-Val-Ala-DL-Asp(OMe)-fluoromethylketone, all of which can be obtained from Bachem Bioscience Inc., PA. Other exemplary caspase 1 inhibitors include, for example, Z-Val-Ala-Asp-fluoromethylketone, biotin-X-Val-Ala-Asp-fluoromethylketone, Ac-Val-Ala-Asp-aldehyde, Boc-Asp-fluoromethylketone, Ac-Ala-Ala-Val-Ala-Leu-Leu-Pro-Ala-Val-Leu-Leu-Ala-Leu-Leu-Pro-Tyr-Val-Ala-Asp-aldehyde (SEQ ID NO: 1), biotin-Tyr-Val-Ala-Asp-fluoroacyloxymethylketone (SEQ ID NO: 20), Ac-Tyr-Val-Ala-Asp-acyloxymethylketone (SEQ ID NO: 21), Z-Asp-CH2-DCB, and Z-Tyr-Val-Ala-Asp-fluoromethylketone (SEQ ID NO: 22), all of which are available from Calbiochem, IDN-11104 available from Conatus Pharmaceuticals, and VX-740 and VX-756 available from Vertex Pharmaceuticals.

Exemplary synthetic caspase 2 inhibitors, include, for example, Ac-Val-Asp-Val-Ala-Asp-aldehyde (SEQ ID NO: 23), which can be obtained from Bachem Bioscience Inc., PA, and Z-Val-Asp-Val-Ala-Asp-fluoromethylketone (SEQ ID NO: 24), which can be obtained from Calbiochem, Calif.

Exemplary synthetic caspase 3 precursor protease inhibitors include, for example, Ac-Glu-Ser-Met-Asp-aldehyde (pseudo acid) (SEQ ID NO: 25) and Ac-Ile-Glu-Thr-Asp-aldehyde (pseudo acid) (SEQ ID NO: 26) which can be obtained from Bachem Bioscience Inc., PA. Exemplary synthetic caspase 3 inhibitors include, for example, Ac-Asp-Glu-Val-Asp-aldehyde (SEQ ID NO: 27), Ac-Asp-Met-Gln-Asp-aldehyde (SEQ ID NO: 28), biotinyl-Asp-Glu-Val-Asp-aldehyde (SEQ ID NO: 29), Z-Asp-Glu-Val-Asp-chloromethylketone (SEQ ID NO: 30), Z-Asp(OMe)-Glu(OMe)-Val-DL-Asp(OMe)-fluoromethylketone (SEQ ID NO: 31), and Z-Val-Ala-DL-Asp(OMe)-fluoromethylketone which can be obtained from Bachem Bioscience Inc., PA. Other exemplary caspase 3 inhibitors include, for example, Ac-Ala-Ala-Val-Ala-Leu-Leu-Pro-Ala-Val-Leu-Leu-Ala-Leu-Leu-Ala-Pro-Asp-Glu-Val-Asp-aldehyde (SEQ ID NO: 2), biotin-X-Asp-Glu-Val-Asp-fluoromethylketone (SEQ ID NO: 32), Ac-Asp-Glu-Val-Asp-chloromethylketone (SEQ ID NO: 33), all of which are available from Calbiochem. Another exemplary caspase 3 inhibitor includes, the caspase 3 inhibitor N-benzyloxycarbonal-Asp(OMe)-Glu(OMe)-Val-Asp(Ome)-fluoromethyketone (z-Asp-Glu-Val-Asp-fmk) (SEQ ID NO: 34), which is available from Enzyme Systems Products. Additional exemplary caspase 3 inhibitors include M-826 and M-791 available from Merck-Frosst, Immunocasp-3, Ad-G/iCasp3, and PEF-F8-CP3.

Exemplary synthetic caspase 4 inhibitors include, for example, Ac-Leu-Glu-Val-Asp-aldehyde (SEQ ID NO: 35) and Z-Tyr-Val-Ala-DL-Asp-fluoromethylketone (SEQ ID NO: 36), which can be obtained from Bachem Bioscience Inc., PA, and Ac-Ala-Ala-Val-Ala-Leu-Leu-Pro-Ala-Val-Leu-Leu-Ala-Leu-Leu-Ala-Pro-Leu-Glu-Val-Pro-aldehyde (SEQ ID NO: 3), which can be obtained from Calbiochem, Calif.

Exemplary synthetic caspase 5 inhibitors include, for example, Z-Trp-His-Glu-Asp-fluoromethylketone (SEQ ID NO: 37), which can be obtained from Calbiochem, Calif., and Ac-Trp-Glu-His-Asp-aldehyde (SEQ ID NO: 38) and Z-Trp-Glu(O-Me)-His-Asp(O-Me) fluoromethylketone (SEQ ID NO: 39), which can be obtained from Sigma Aldrich, Germany.

Exemplary synthetic caspase 6 inhibitors include, for example, Ac-Val-Glu-Ile-Asp-aldehyde (SEQ ID NO: 40), Z-Val-Glu-Ile-Asp-fluoromethylketone (SEQ ID NO: 41), and Ac-Ala-Ala-Val-Ala-Leu-Leu-Pro-Ala-V al-Leu-Leu-Ala-Leu-Leu-Ala-Pro-Val-Glu-Ile-Asp-aldehyde (SEQ ID NO: 4), which can be obtained from Calbiochem. Another exemplary caspase 6 inhibitor includes Immunocasp-6.

Exemplary synthetic caspase 7 inhibitors include, for example, Z-Asp(OMe)-Gln-Met-Asp(OMe) fluoromethylketone (SEQ ID NO: 42), Ac-Asp-Glu-Val-Asp-aldehyde (SEQ ID NO: 43), Biotin-Asp-Glu-Val-Asp-fluoromethylketone (SEQ ID NO: 44), Z-Asp-Glu-Val-Asp-fluoromethylketone (SEQ ID NO: 45), Ac-Ala-Ala-Val-Ala-Leu-Leu-Pro-Ala-Val-Leu-Leu-Ala-Leu-Leu-Ala-Pro-Asp-Glu-Val-Asp-aldehyde (SEQ ID NO: 2), which can be obtained from Sigma Aldrich, Germany.

Exemplary synthetic caspase 8 inhibitors include, for example, Ac-Asp-Glu-Val-Asp-aldehyde (SEQ ID NO: 46), Ac-Ile-Glu-Pro-Asp-aldehyde (SEQ ID NO: 47), Ac-Ile-Glu-Thr-Asp-aldehyde (SEQ ID NO: 48), Ac-Trp-Glu-His-Asp-aldehyde (SEQ ID NO: 49) and Boc-Ala-Glu-Val-Asp-aldehyde (SEQ ID NO: 50) which can be obtained from Bachem Bioscience Inc., PA. Other exemplary caspase 8 inhibitors include, for example, Ac-Ala-Ala-Val-Ala-Leu-Leu-Pro-Ala-Val-Leu-Leu-Ala-Leu-Leu-Ala-Pro-Ile-Glu-Thr-Asp-aldehyde (SEQ ID NO: 5) and Z-Ile-Glu-Thr-Aspfluoromethylketone (SEQ ID NO: 51), which can be obtained from Calbiochem, Calif.

Exemplary synthetic caspase 9 inhibitors, include, for example, Ac-Asp-Glu-Val-Asp-aldehyde (SEQ ID NO: 52), Ac-Leu-Glu-His-Asp-aldehyde (SEQ ID NO: 53), and Ac-Leu-Glu-His-Asp-chloromethylketone (SEQ ID NO: 54) which can be obtained from Bachem Bioscience Inc., PA. Other exemplary caspase 9 inhibitors include, for example, Z-Leu-Glu-His-Asp-fluoromethylketone (SEQ ID NO: 55) and Ac-Ala-Ala-Val-Ala-Leu-Leu-Pro-Ala-Val-Leu-Leu-Ala-Leu-Leu-Ala-Pro-Leu-Glu-His-Asp-aldehyde (SEQ ID NO:6), which can be obtained from Calbiochem, Calif. Another exemplary caspase 9 inhibitor includes FKBP12/caspase-9 fusion protein.

The pan-caspase inhibitor may also be an endogenous caspase inhibitor or a combination of an endogenous caspase inhibitor with one or more synthetic caspase inhibitors. For example, one useful class of endogenous caspase inhibitor includes proteins known as inhibitors of apoptosis proteins (IAPs) (Deveraux et al., (1998) EMBO J. 17(8): 2215-2223) including bioactive fragments and analogs thereof. One exemplary IAP includes X-linked inhibitor of apoptosis protein (XIAP), which has been shown to be a direct and selective inhibitor of caspase-3, caspase-7 and caspase-9. Another exemplary IAP includes survivin (see, U.S. Pat. No. 6,245,523; Papapetropoulos et al., (2000) J. BIOL. CHEM. 275: 9102-9105), including bioactive fragments and analogs thereof. Survivin has been reported to inhibit caspase-3 and caspase-7 activity.

In certain embodiments, the one or more apoptosis inhibitors may target the inhibitor of apoptosis proteins (IAPs) and second mitochondria-derived activator of caspases (SMACs). Exemplary apoptosis inhibitors that target IAPs and SMACs, include, for example, BIR3 antagonists available from Idun Pharmaceuticals, capped tripeptide XIAP antagonists from Abbot Laboratories, TWX024, polyphenylurea derivatives, SMAC-mimetic compounds, embelin, XIAP antisense and RNAi constructs, AEG35156/GEM 640 available from Aegera Therapeutics, HIV-Tat- and polyarginine conjugated SMAC peptides, and nonpeptide small-molecule SMAC mimetics. It is contemplated that one or more of the apoptosis inhibitors which target IAPs and SMACs may be used in combination with one or more necrostatins (e.g., necrostain-1 and/or necrostatin-4).

In certain embodiments, the one or more apoptosis inhibitors may target the TNF-related apoptosis-inducing ligand (TRAIL) receptors. Exemplary apoptosis inhibitors that target the TRAIL receptors, include, for example, HGS-ETR1, HGS-ETR2, and HGS-TR2J available from Human Genome Sciences, and PRO1762 available from Amgen. It is contemplated that one or more of the apoptosis inhibitors which target the TRAIL receptors may be used in combination with one or more necrostatins (e.g., necrostain-1 and/or necrostatin-4).

In certain embodiments, the one or more apoptosis inhibitors may target CD95/Fas. Exemplary apoptosis inhibitors that target CD95/FAS, include, for example, CD95-Fc available from ApoGenix GmbH. It is contemplated that one or more of the apoptosis inhibitors which target CD95/Fas may be used in combination with one or more necrostatins (e.g., necrostain-1 and/or necrostatin-4).

In certain embodiments, the one or more apoptosis inhibitors may be an anti-FasL factors. Exemplary anti-FasL factors include, for example, anti-FasL neutralizing antibody (available, for example, from Pharmingen, San Diego, Calif.); peptides and nucleic acids (for example, anti-FasL aptamers) that bind FasL to prevent or reduce its binding to its cognate receptor; certain antibodies and antigen binding fragments thereof and peptides that bind preferentially to the Fas receptor; antisense nucleotides and double stranded RNA for RNAi that ultimately reduce or eliminate the production of either FasL or the Fas receptor; soluble Fas; soluble FasL; decoy receptor-3 (DcR3) and analogues thereof; matrix metalloproteinases (MMPs); vasoactive intestinal peptide (VIP); pituitary adenylate cyclase-activating polypeptide (PACAP); forskolin; combined use of benazepril and valsartan; nonpeptidic corticotropin-releasing hormone receptor type 1 (CRH-R1)-specific antagonists; mimosine; peptides that produce a defective Fas-FasL complex; platelet-activating factor (PAF); and endothelin-1 (ET-1). These anti-FasL factors can act as direct or indirect antagonists of FasL activity.

In certain embodiments, the one or more apoptosis inhibitors may target the tumor necrosis factor (TNF). Exemplary apoptosis inhibitors that target TNF, include, for example, recombinant TNF-α, adalimumab available from Abbott, infliximab available from Centocor Ortho Biotech Inc., etanercept from Amgen, CDP571 available from Celltech, and ISIS 104838 (a 2'-O-methoxyethyl antisense construct against TNF-alpha) available from ISIS Pharmaceuticals. It is contemplated that one or more of the apoptosis inhibitors which target TNF may be used in combination with one or more necrostatins (e.g., necrostain-1 and/or necrostatin-4).

In certain embodiments, the one or more apoptosis inhibitors may target survivin. Exemplary apoptosis inhibitors that target survivin, include, for example, LY2181308 available from ISIS Pharmaceuticals and Ad-survivin T34A. It is contemplated that one or more of the apoptosis inhibitors which target survivin may be used in combination with one or more necrostatins (e.g., necrostain-1 and/or necrostatin-4).

In certain embodiments, the one or more apoptosis inhibitors may target the Bcl-2 proteins. Exemplary apoptosis inhibitors that target the Bcl-2 proteins, include, for example, Bcl-2 blockers available from Idun Pharmaceuticals and Abbot Laboratories, Gx01 series of compounds available from Gemin X Pharmaceuticals, Bcl-2 small-molecule antagonist, Tetrocarcin-A derivatives available from Kyowa Hakko Kogyo Co., Chelerythrine, antimycin A derivatives, HA14-1, synthetic compound binding to the BH3 of Bcl-2, Genasense available from Sanofi-Aventis, ISIS 22783 available from ISIS Pharmaceuticals, bispecific Bcl-2/Bcl-XL antisense, BH3 peptides from Bax, Bak, Bid or Bad, SAHBs, and BH3Is. It is contemplated that one or more of the apoptosis inhibitors which target the Bcl-2 proteins may be used in combination with one or more necrostatins (e.g., necrostain-1 and/or necrostatin-4).

In certain embodiments, the one or more apoptosis inhibitors may target p53. Exemplary apoptosis inhibitors that target p53, include, for example, INGN201 available from Invitrogen Therapeutics, SCH58500 available from Schering-Plough, ONYX-015 available from Onyx Pharmaceuticals, C-terminal p53 peptides, CDB3, Amifostine, CP31398 available from Pfizer, Prima-1, HPF E6-binding peptide aptamers, Nutlins available from Roche, Chalcones, Small peptide compounds, and Pifithrin-α. It is contemplated that one or more of the apoptosis inhibitors which target p53 may be used in combination with one or more necrostatins (e.g., necrostain-1 and/or necrostatin-4).

In certain embodiments, it is contemplated that one or more necrostatins (e.g., necrostatin-1 and/or necrostatin-4) may be used in combination with a pan-caspase inhibitor. For example, in one embodiment, necrostain-1 and/or necrostatin-4 may be used in combination with Z-VAD available from R&D Systems (Cat. No. FMK001) and Promega (Cat. No. G7231). In another embodiment, necrostain-1 and/or necrostatin-4 may be used in combination with IDN-6556 available from Conatus Pharmaceuticals. In yet another embodiment, necrostain-1 and/or necrostatin-4 may be used in combination with IDN-6734 available from Conatus Pharmaceuticals.

In certain embodiments, it is contemplated that one or more necrostatins (e.g., necrostatin-1 and/or necrostatin-4) may be used in combination with a TNF inhibitor. For example, in one embodiment, necrostain-1 and/or necrostatin-4 may be used in combination with adalimumab available from Abbot Laboratories. In another embodiment, necrostain-1 and/or necrostatin-4 may be used in combination with etanercept available from Amgen, Inc. In yet another embodiment, necrostain-1 and/or necrostatin-4 may be used in combination with infiximab available from Centocor Ortho Biotech, Inc.

In certain embodiments, it is contemplated that one or more necrostatins (e.g., necrostatin-1 and/or necrostatin-4) may be used in combination with a p53 agonist. For example, in one embodiment, necrostain-1 and/or necrostatin-4 may be used in combination with INGN 201 available from Invitrogen Therapeutics. In another embodiment, necrostain-1 and/or necrostatin-4 may be used in combination with nutlins, for example, nutlin-3 available from Cayman Chemical (Cat. No. 10004372). In yet another embodiment, necrostain-1 and/or necrostatin-4 may be used in combination with CP31398 available from Tocris Bioscience (Cat. No. 3023).

In certain embodiments, it is contemplated that one or more necrostatins (e.g., necrostatin-1 and/or necrostatin-4) may be used in combination with an anti-FasL factor. For example, in one embodiment, necrostain-1 and/or necrostatin-4 may be used in combination with anti-FasL neutralizing antibody available from Pharmingen (San Diego, Calif.).

As shown in FIG. 1, depending upon the specific apoptotic inhibitor chosen, it is possible that the apoptotic inhibitor can modulate both the apoptotic and necrotic pathways, and depending upon the specific necrosis inhibitor chosen, it is possible that the necrosis inhibitor can modulate both the necrotic and apoptotic pathways. For example, a RIP-1 inhibitor may inhibit both necrotic and apoptotic cell death thus preserving the viability of the retinal ganglion cells in the retina of the eye of a subject with an ocular condition as disclosed herein.

As discussed herein, the methods and compositions of the invention can preserve the visual function of an eye of a subject with an ocular condition. Assessment of axonal regeneration may also be monitored through visual function tests as disclosed herein. Visual function can be measured using one or more of a variety of methods well-known in the art. For example, visual function can be assessed by measuring visual acuity. Visual acuity can be assessed, for example, by using conventional "eye charts" in which visual acuity is evaluated by the ability to discern letters of a certain size, with five letters of a given size present on each line (see, e.g., the "ETDRS" eye chart described in the Murphy, R. P., CURRENT TECHNIQUES IN OPTHALMIC LASER SURGERY, $3^{rd}$ Ed., edited by L. D. Singerman, and G. Cascas, Butterworth Heinemann, 2000). Evaluation of visual acuity may also be achieved by measuring reading speed and reading time. Visual acuity may be measured to evaluate whether administration of a necrosis inhibitor and/or an apoptosis inhibitor to the affected eye preserves or permits improvement of visual acuity (e.g., to 20/40 vision or to 20/20 vision).

Visual function may also be measured by determining whether there is an increase in the thickness of the Nerve Fiber layer (NFL) (e.g., NFL thickness is 15% thicker than, 35% thicker than, 50% thicker than, 60% thicker than, 70% thicker than, or 80% thicker than a macula without the treatment as measured by optical coherence tomography (OCT); an improvement of the ganglion cell layer or bipolar cell layer or photoreceptor cell layer or its subdivisions as seen in the OCT; an improvement of visual field (e.g., by at least 10% in the mean standard deviation on the Humphrey Visual Field Test; an improvement of an electroretinograph (ERG), a measurement of the electrical response of the retina to light stimulation, (e.g., to increase ERG amplitude by at least 15%); and/or preservation or improvement of multifocal ERG, which evaluates the response of the retina to multifocal stimulation and allows characterization of the function of a limited area of the retina.

Visual function may also be measured by electrooculography (EOG), which is a technique for measuring the resting potential of the retina. EOG is particularly useful for the assessment of RPE function. EOG may be used to evaluate whether administration of a necrosis inhibitor and/or an apoptosis inhibitor to the retina of the affected eye preserves or permits improvement in, for example, the Arden ratio (e.g., an increase in Arden ratio of at least 10%).

Visual function may also be assessed through fundus autofluorescence (AF) imaging, which is a clinical tool that allows evaluation of the interaction between photoreceptor cells and the RPE. For example, increased fundus AF or decreased fundus AF has been shown to occur in AMD and other ocular disorders. Fundus AF imaging may be used to evaluate whether administration of a necrosis inhibitor and/or an apoptosis inhibitor to the retina of the affected eye slows disease progression.

Visual function may also be assessed by evaluation of contrast sensitivity, which a measurement of the ability to discern between luminances of different levels in a static image. An evaluation of contrast sensitivity may be used to assess whether administration of a necrosis inhibitor and/or an apoptosis inhibitor to the retina of the affected eye preserves or permits improvement in the resolving power of the eye.

Visual function may also be assessed by microperimetry, which monitors retinal visual function against retinal thickness or structure and the condition of the subject's fixation over time. Microperimetry may be used to assess whether administration of a necrosis inhibitor and/or an apoptosis inhibitor to the retina of the affected eye preserves or permits improvement in retinal sensitivity and fixation.

In certain embodiments, the necrosis inhibitor, e.g., a necrostatin, and/or the apoptosis inhibitor, e.g., a pan-caspase inhibitor such as Z-VAD or IDN-6556, may be administered locally to the eye of a subject, e.g., a human subject, following other treatments of the retina to preserve or to permit improvement of visual acuity (e.g., to 20/40 vision or to 20/20 vision); to increase the thickness of the macula (e.g., macula thickness is 15% thicker than, 35% thicker than, 50% thicker than, 60% thicker than, 70% thicker than, or 80% thicker than a macula without the treatment as measured by optical coherence tomography (OCT)); to permit improvement in the appearance and structure of the photoreceptor cell layer and its supporting RPE, to permit the improvement of visual field (e.g., by at least 10% in the mean standard deviation on the Humphrey Visual Field Test; and/or to permit the improvement of an electroretinograph (ERG), a measurement of the electrical response of the retina to light stimulation, (e.g., to increase ERG amplitude by at least 15%).

In certain embodiments, the necrosis inhibitor, e.g., a necrostatin, and/or the apoptosis inhibitor, e.g., a pan-caspase inhibitor such as Z-VAD or IDN-6556, are administered locally to the eye of a mammal by intravitreal injection. Both agents may be administered on the day of diagnosis and/or the same day that the retina has gone through other treatments and/or in the post-operative period. The agents may then be administered every three days, every five days, or every seven days until the mammal, e.g., a human, has improved vision (e.g., visual acuity has improved to 20/40 vision or to 20/20 vision), the thickness of the NFL or macula has increased (e.g., macula thickness is 15% thicker than, 35% thicker than, 50% thicker than, 60% thicker than, 70% thicker than, or 80% thicker than without treatment as measured by OCT); the appearance of the ganglion cell layer or bipolar cell layer or photoreceptor cell layer and RPE as detected by OCT; the visual field has improved by at least 10% in the mean standard deviation as determined by Humphrey Visual Field testing; and/or the mammal's retina shows an increased response to light stimulation (e.g., at least a 15% increase in amplitude as determined by electroretinography).

The necrosis inhibitor and the apoptosis inhibitor can be administered by the same route or by different routes. The necrosis inhibitor and/or the apoptosis inhibitor may be administered locally to the eye, for example, by intravitreal, intraocular, intraorbital, subconjuctival, subretinal or transscleral routes. For example, the necrosis inhibitor and/or the apoptosis inhibitor may be administered locally to the eye by intravitreal injection. It is contemplated that local modes of administration may reduce or eliminate the incidence of potential side effects (e.g., systemic toxicity) that may occur during systemic administration.

Alternatively, the necrosis inhibitor and/or the apoptosis inhibitor may be administered systemically, e.g., by oral or parenteral routes. Parenteral routes include, for example, intravenous, intrarterial, intramuscular, intradermal, subcutaneous, intranasal and intraperitoneal routes.

The necrosis inhibitor and the apoptosis inhibitor may be administered to a subject simultaneously or sequentially. It will be appreciated that when administered simultaneously, the necrosis inhibitor and the apoptosis inhibitor may be in the same pharmaceutically acceptable carrier (e.g., solubilized in the same viscoelastic carrier that is introduced into the eye) or the two drugs may be dissolved or dispersed in separate pharmaceutical carriers, which are administered at the same time. Alternatively, the drugs may be provided in separate dosage forms and administered sequentially. For example, in some embodiments, the necrostatin may be administered before the pan-caspase inhibitor. In other examples, the pan-caspase inhibitor may be administered before the necrostatin. In addition, it is appreciated that, in some embodiments, a single active agent may inhibit both necrosis and apoptosis.

Administration may be provided as a periodic bolus (for example, intravitreally or intravenously) or as continuous infusion from an internal reservoir (for example, from an implant disposed at an intra- or extra-ocular location (see, U.S. Pat. Nos. 5,443,505 and 5,766,242)) or from an external reservoir (for example, from an intravenous bag, or a contact lens slow release formulation system). The necrosis inhibitor and/or the apoptosis inhibitor may be administered locally, for example, by continuous release from a sustained release drug delivery device immobilized to an inner wall of the eye or via targeted transscleral controlled release into the choroid (see, for example, PCT/US00/00207, PCT/US02/14279, Ambati et al., (2000) INVEST. OPHTHALMOL. VIS. SCI. 41:1181-1185, and Ambati et al., (2000) INVEST. OPHTHALMOL. VIS. SCI. 41:1186-1191). A variety of devices suitable for administering the disclosed necrosis and/or apoptosis inhibitors locally to the inside of the eye are known in the art. See, for example, U.S. Pat. Nos. 6,251,090, 6,299,895, 6,416,777, 6,413,540, and 6,375,972, and PCT/US00/28187.

The necrosis inhibitor and/or the apoptosis inhibitor may be solubilized in a carrier, for example, a viscoelastic carrier, that is introduced locally into the eye. One or both inhibitors also may be administered in a pharmaceutically acceptable carrier or vehicle so that administration does not otherwise adversely affect the recipient's electrolyte and/or volume balance. The carrier may comprise, for example, physiologic saline or other buffer system. In exemplary embodiments, the necrostatin, the pan-caspase inhibitor, or both the necrostatin and the pan-caspase inhibitor may be solubilized in PBS or another aqueous buffer by sonication. Alternatively, one or both drugs may be solubilized using conventional solvent or solubilization systems, for example, dimethyl sulfoxide (DMSO), dimethoxyethane (DME), dimethylformamide (DMF), cyclodextran, micelles, liposomes, liposomal agents, and other solvents known in the art to aid in the solubilization and administration of hydrophobic agents.

In other embodiments, the necrosis inhibitor and/or the apoptosis inhibitor may be solubilized in a liposome or microsphere. Methods for delivery of a drug or combination of drugs in liposomes and/or microspheres are well-known in the art.

In addition, it is contemplated that the necrosis inhibitor and/or the apoptosis inhibitor may be formulated so as to permit release of one or both inhibitors over a prolonged period of time. A release system can include a matrix of a biodegradable material or a material, which releases the incorporated active agents. The active agents can be homogeneously or heterogeneously distributed within a release system. A variety of release systems may be useful in the practice of the invention, however, the choice of the appropriate system will depend upon the rate of release required by a particular drug regime. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, under certain circumstances, synthetic release systems are preferred because generally they are more reliable, more reproducible and produce more defined release profiles. The release system material can be selected so that inhibitors having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly (caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly (ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

One of the primary vehicles currently being developed for the delivery of ocular pharmacological agents is the poly(lactide-co-glycolide) microsphere for intraocular injection. The microspheres are composed of a polymer of lactic acid and glycolic acid, which are structured to form hollow spheres. These spheres can be approximately 15-30 µm in diameter and can be loaded with a variety of compounds varying in size from simple molecules to high molecular weight proteins such as antibodies. The biocompatibility of these microspheres is well established (see, Sintzel et al., (1996)), and microspheres have been used to deliver a wide variety of pharmacological agents in numerous biological systems. After injection, poly(lactide-co-glycolide) microspheres are hydrolyzed by the surrounding tissues, which cause the release of the contents of the microspheres (Zhu et al., (2000)). As will be appreciated, the in vivo half-life of a microsphere can be adjusted depending on the specific needs of the system.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions may be conducted simultaneously.

EXAMPLES

The invention is further illustrated by the following examples, which are provided for illustrative purposes only, and should not be construed as limiting the scope or content of the invention in any way.

In the examples described herein, all animal experiments adhered to the Association for Research in Vision and Ophthalmology Statement for the Use of Animals in Ophthalmic and Vision Research, and protocols were approved by the Animal Care Committee of the Massachusetts Eye and Ear Infirmary. Wild-type C57BL/6 mice were purchased from Charles River Laboratories (Wilmington, Mass.). The mice were fed standard laboratory chow and allowed free access to water in an air-conditioned room with a 12 hour light/12 hour dark cycle. RIP-3 knockout (RIP-3-/-) mice were kindly provided by Dr. V. M. Dixit (Genentech, San Francisco, Calif.). RIP-3-/- mice were generated as described previously and backcrossed to C57BL/6 mice (Newton et al., (2004) MOL CELL BIOL 24:1464-1469). Except as noted otherwise, the animals were anesthetized with ketamine hydrochloride (30 mg/kg; Ketalar, Parke-Davis, Morris Plains, N.J.) and xylazine hydrochloride (5 mg/kg; Rompun, Harver-Lockhart, Morris Plains, N.J.) before all experimental manipulations.

Two mouse models of RGC death were utilized: optic nerve (ON) injury and N-methyl-D-aspartate (NMDA) retinal excitotoxicity. ON injury leads to RGC death as a result of primary damage to the axons, with its ensuing disruption of retrograde axonal transport (Libby et al., (2005) PLoS GENET 1:17-26) and is used as an RGC death model. In the ON injury model, mice were anesthetized and subjected to severe crush injury at 1-2 mm distance from the eyeball for 15 seconds using cross-action forceps taking special care not to interfere with the blood supply (Levkovitch-Verbin, (2004) EYE 18:1066-1074). Injured mice were randomly divided into 4 groups for treatment: vehicle group (0.5% DMSO and 0.8% cyclodextrin in PBS, n=6), ZVAD group (300 n=6), Nec-1 group (4 mM, n=6), and ZVAD plus Nec-1 group (n=6). Soon after injury, each group received an intravitreal injection (2 µl) with the respective compounds. In the NMDA retinal excitotoxicity model, NMDA (2 µl of a 0.1M stock; Sigma-Aldrich) was injected intravitreously in combination with ZVAD, Nec-1, or ZVAD plus Nec-1 and mice were separated into the aforementioned 4 groups. The dose of these compounds was selected based on previous studies (Karl et al., (2008) PROC NATL ACAD SCI USA 105: 19508-19513; Knoferle et al., (2010) PROC NATL ACAD SCI USA 107:6064-6069; Nakazawa et al., (2006) J NEUROSCI 26:12633-12641; Rosenbaum et al., (2010) J NEUROSCI RES 88:1569-1576).

The following reagents were utilized: Z-VAD (Alexis, Plymouth Meeting Pa.), IDN-6556 (kindly provided by TetraLogics Pharmaceuticals), a Nec-1 compound of Formula I-C (a kind gift from Dr. J. Yuan, Harvard Medical School, Boston, Mass.), and a Nec-4 compound of Formula IV-A (kindly provided by TetraLogics Pharmaceuticals).

ON-injured mice received an intravitreal injection of 3-methyladenine (3-MA), in DMSO (33.3 mM; Sigma-Aldrich, St. Louis, Mo.), a goat anti-mouse TNF-α blocking antibody, or the appropriate control goat antibody (R & D Systems, Minneapolis, Minn.).

Intravitreal injections were performed as follows. Briefly, the tip of a 33 gauge needle (Hamilton, Reno, Nev.) was carefully inserted through the sclera into the intravitreal space to reduce intraocular pressure. Then, the needle was extracted, loaded with compounds and tangentially reinserted through the sclera into the intravitreal space, inducing a self-sealing wound tunnel. After injection, the absence of choroidal bleeding was confirmed. At specified times after injury, mice were sacrificed with an overdose of sodium pentobarbital, and eyes were enucleated.

Total RNA extraction, cDNA synthesis and PCR amplification have been performed as previously reported (Kayama et al., (2010) OPHTHALMIC RES 43:79-91). A real-time PCR assay was performed with Prism 7700 Sequence Detection System (Applied Biosystems, Foster City, Calif.). The primers are shown below in Table 1.

TABLE 1

| II. Taqman Gene Expression Assays | | |
|---|---|---|
| Protein | Assay ID # | Supplier |
| RIP1 | Mm00436354_m1 | Applied Biosystems |
| RIP3 | Mm00444947_m1 | Applied Biosystems |
| TNF-α | Mm99999068_m1 | Applied Biosystems |
| Atg5 | Mm00504340_m1 | Applied Biosystems |
| Atg7 | Mm00512209_m1 | Applied Biosystems |
| Atg12 | Mm00503201_m1 | Applied Biosystems |

For relative comparison of each gene, the Ct value of real-time PCR data was analyzed with the ΔΔCt method and normalized to an endogenous control ((3-actin).

For Western blot analysis, whole retinas were harvested and lysed for 30 min on ice in lysis buffer (50 mM Tris-HCl [pH 8], with 120 mM NaCl and 1% Nonidet P-40), supplemented with a mixture of proteinase inhibitors (Complete Mini; Roche Diagnostics, Basel, Switzerland). Thirty micrograms of protein per sample were separated in a 4-20% gradient sodium dodecyl sulfate-polyacrylamide gel (SDS-PAGE) (Invitrogen Corporation, Carlsbad, Calif., USA) electrophoresis and the proteins were electroblotted onto PVDF membranes. After 20 min incubation in blocking solution (Starting Block™ T20, Thermo Scientific, Waltham, Mass.), membranes were incubated with primary antibodies overnight at 4° C. Peroxidase-labeled secondary antibodies (Amersham Pharmacia Biotech, Piscataway, N.J., USA) were used and proteins were visualized with enhanced chemiluminescence technique (Amersham Pharmacia Biotech). Full list of primary antibodies and working concentrations are shown below in Table 2.

TABLE 2

| | | I. Antibodies | | |
|---|---|---|---|---|
| Antigen | Host | Immuno-blot | Immuno-staining | Supplier |
| RIP3 | Rabbit | 1:10000 | No | Sigma-Aldrich |
| RIP1 | Mouse | 1:1000 | No | BD Biosciences |
| LC3 | Rabbit | 1:1000 | No | Cell Signalling |
| LC3 | Goat | No | 1:50 | SCBT |
| Bm3b | Goat | No | 1:50 | SCBT |
| Caspase-9 | Rabbit | No | 1:300 | Cell Signalling |
| Caspase-3 | Rabbit | No | 1:300 | Cell Signalling |
| TNF-α (blocking antibody) | Goat | No | No | R&D |
| β-tubulin | Rabbit | 1:1000 | No | Cell Signalling |

TUNEL and quantification of TUNEL (+) cells were performed as previously described (Nakazawa et al., (2007) PROC NATL ACAD SCI USA 104:2425-2430) by using the ApopTag Fluorescein In Situ Apoptosis Detection Kit (S7110; Chemicon International, Temecula, Calif.).

All values disclosed were expressed as the mean±SD. Statistical differences between two groups were analyzed by Mann-Whitney U test. Multiple group comparison was performed by ANOVA followed by Tukey-Kramer adjustments. Differences were considered significant at $P<0.05$.

Example 1: Efficacy of a Necrosis Inhibitor and a Pan-Caspase Inhibitor in the Treatment of Glaucoma and Optic Nerve Injury Glaucoma is a group of ocular disorders, characterized by optic nerve injury. In most cases of glaucoma, the optic nerve injury is caused by elevated intraocular pressure. Furthermore, higher intraocular pressures are generally associated with greater nerve damage. In this example, mouse models of optic nerve (ON) injury was used to assess the role of RIP-mediated programmed necrosis and apoptosis in this ocular disorder. Given that ON injury is a hallmark of glaucoma, this model also provided an assessment of RIP-mediated programmed necrosis in RGC loss in glaucoma.

A. Neutralization of TNF-α Prevents Optic Nerve Injury-Induced RGC Death

Figure 2A:
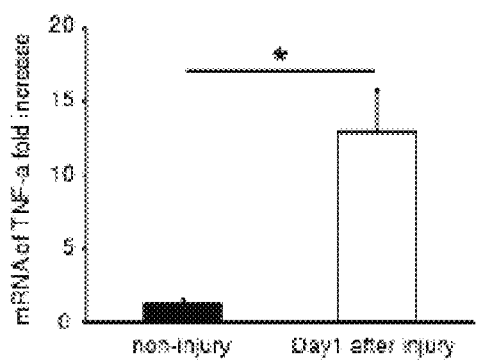
FIGS. 2A-2D provide graphs and a photograph showing TNF-α expression (FIG. 2A and FIG. 2B), RGC numbers per field (FIG. 2C), and IPL thickness (FIG. 2D) in mice that underwent ON injury and were injected with an anti-TNF-α neutralizing antibody.

Recent evidence has demonstrated the role of TNF-α as a mediator of retinal ganglion cell (RGC) death in glaucoma (Nakazawa et al., (2006) J NEUROSCI 26:12633-12641)). Furthermore, in the glaucomatous eye, death receptors of TNF-α are up-regulated in RGCs and optic nerve axons (Yan et al., (2000), Yuan et al., (2000), Tezel et al., (2001) INVEST OPHTHALMOL VIS SCI 42:1787-1794)). To investigate whether TNF-α is involved in RGC cell death in mice subjected to optic nerve (ON) injury (induced by physical injury to the optic nerve), TNF-α level in the retina was measured using quantitative real-time RT-PCR. As depicted in FIG. 2A, at one day after ON injury, TNF-α mRNA levels increased almost 10- to 13-fold relative to non-injured mice.

An anti-TNF-α neutralizing antibody (0.1 mg/ml) or a control antibody was injected into the vitreous of mice that underwent ON injury. One week following injection, the number of RGCs were measured. In addition, inner plexiform layer (IPL) thickness (a location of RGC axons) was also assessed. Specifically, eyes were enucleated and RGC loss was quantified from histological sections of mouse retina. Only transverse sections involving the optic disc were used for analysis and the fields corresponding to approximately 400 μm of both sides of retina extending from the ON head (2 points/section×3 sections per eye, n=6) were examined with an optical microscope (×40 objectives). IPL thickness was measured with OpenLab software (Open Lab, Florence, Italy) (2 points/section×3 sections per eye, n=6). The ratio of IPL thickness was calculated as a percentage of IPL thickness in the normal mouse eyes (n=6).

Figure 2B:
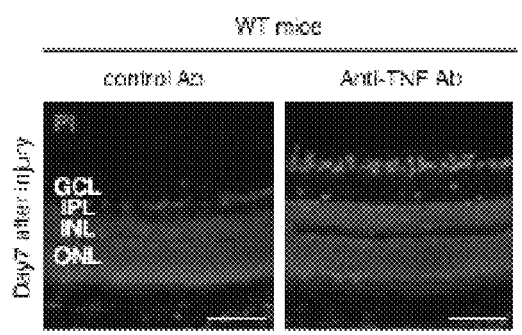
Figure 2C:
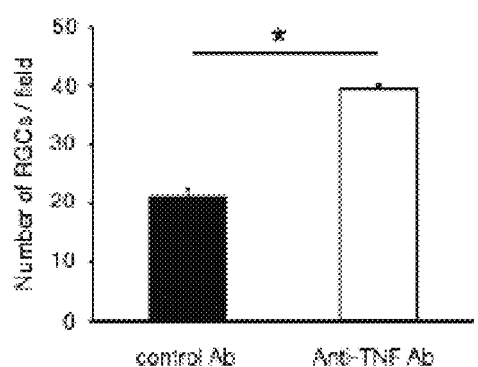
Figure 2D:
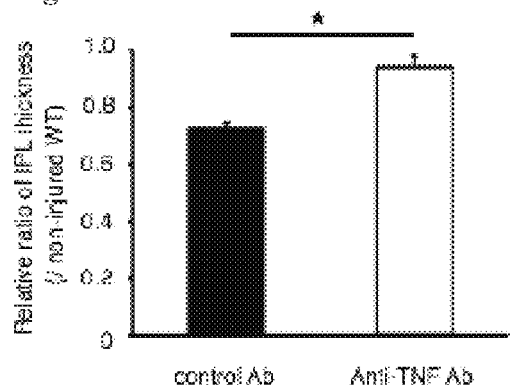

Mice treated with the control antibody showed significant reduction both in RGCs and IPL thickness (FIGS. 2B-2D), whereas, mice treated with TNF-α neutralizing antibody showed negligible loss of RGCs (FIGS. 2B and 2C) and minimal change in IPL thickness (FIGS. 2B and 2D). These data indicate that TNF-α plays a critical role in RGC death after ON injury.

B. ON Injury Induces Changes in RIP3 and RIP1 Expression

Figure 2E:
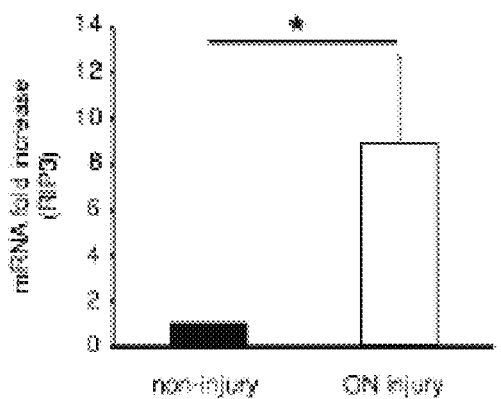
FIGS. 2E-2F provide graphs showing RIP1 and RIP3 expression in the retina of mice that underwent ON injury.
Figure 2F:
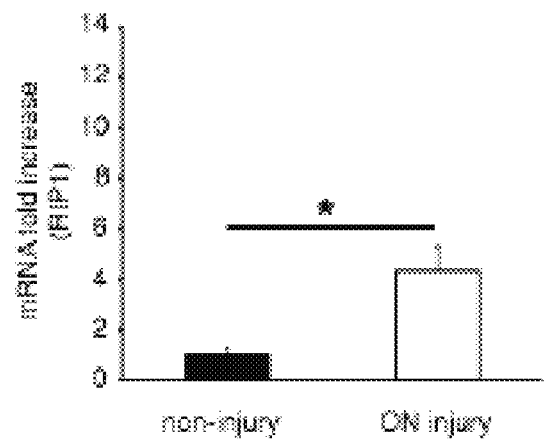
Figure 2G:
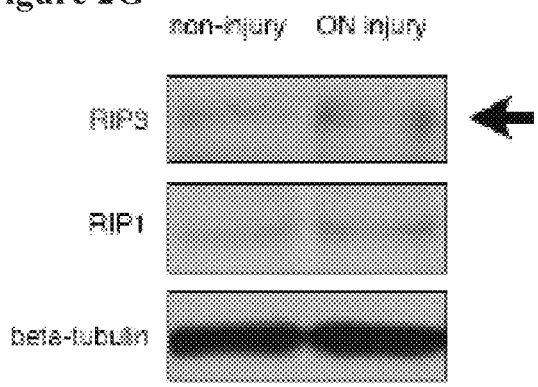
FIG. 2G provides a photograph and FIGS. 2I and 2H, respectively, provide graphs showing RIP1 and RIP3 protein levels in the retina of mice having undergone ON injury.
Figure 2H:
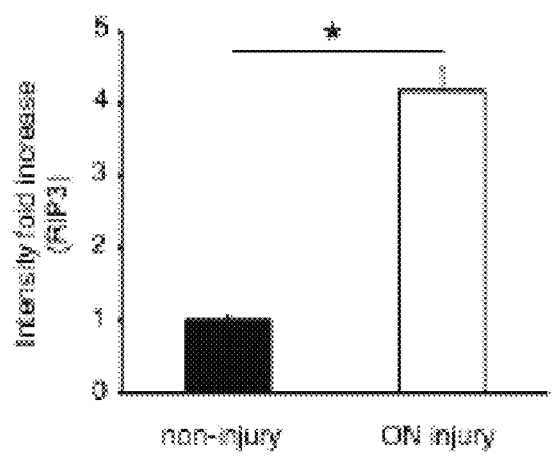
Figure 2I:
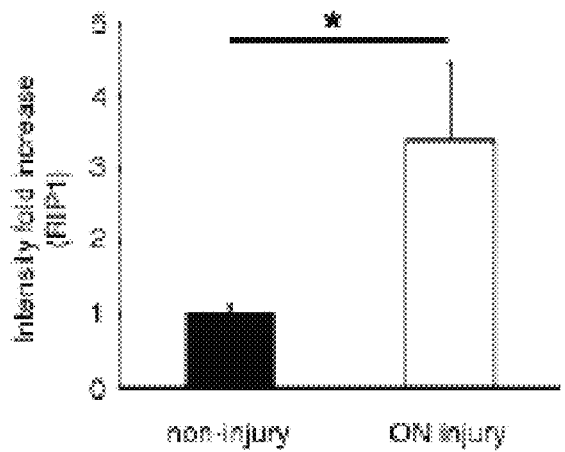

TNF-α has been shown to be a potent inducer of programmed necrosis as well as apoptosis (Degterev et al., (2005) NAT CHEM BIOL 1:112-119, Balkwill, (2009)). The kinases RIP3 and RIP1 are key signaling molecules in cellular apoptotic and necrotic pathways and are regulated by TNF-α (He et al., (2009) CELL 137:1100-1111, Vandenabeele et al., (2010) SCI SIGNAL 3:re4)). Thus, RIP3 and RIP1 mRNA levels were measured in the retina of mice with ON injury using quantitative RT-PCR. One day after ON injury, expression of RIP3 and RIP1 increased significantly up to 9- and 5-fold, respectively, compared to non-injured mice (FIGS. 2E and 2F). RIP3 and RIP1 protein levels were also assessed using Western Blot analysis. After ON injury, expressions of RIP3 and RIP1 were found to be approximately 3-fold up-regulated compared with non-injured retina (FIGS. 2G-2I). These results suggest that RIP kinases may contribute to ON injury-induced RGC death.

C. Simultaneous Inhibition of RIP Kinases and Caspases is Required for Preventing RGC Death In human glaucoma, RGC death has been attributed mainly to apoptosis (Kerrigan et al., (1997), Tatton et al., (2001)). Indeed, activation of caspase-dependent apoptotic pathways has been demonstrated to occur after ON injury (Kermer et al., (2000)). The activities of caspase-8, caspase-9 and caspase-3 were measured using a commercially available kit according to the manufacturer's instructions (APT171/131/139; Millipore, Billerica, Mass.). As seen in FIG. 3R, the activities of caspase-3, caspase-8, and caspase-9 were significantly increased one day after ON injury when compared with non-injured retina. In line with a previous report (Chauvier et al., (2007)), broad caspase inhibition with Z-VAD (benzoyl-Val-Ala-Asp-fluoromethyl ketone) failed to rescue RGCs one day after ON injury (FIGS. 3A and 3B), despite its ability to decrease the activities of the caspases by 70% (FIGS. 3H-3K).

Nec-1, which is a potent and selective inhibitor of programmed necrosis targeting RIP1 kinase activity (Degterev et al., (2008)), was employed to investigate the effect of RIP kinase inhibition in RGC death after ON injury. Mice received an intravitreal injection of Z-VAD (300 uM) and/or Nec-1 (400 uM). The dose of these compounds was selected based on studies that established that their half-life inside the eye is around 6 hours. Administration of Nec-1 and/or Z-VAD did not affect increase of TNF-$\alpha$ levels after ON injury (FIG. 3L).

Figure 3A:
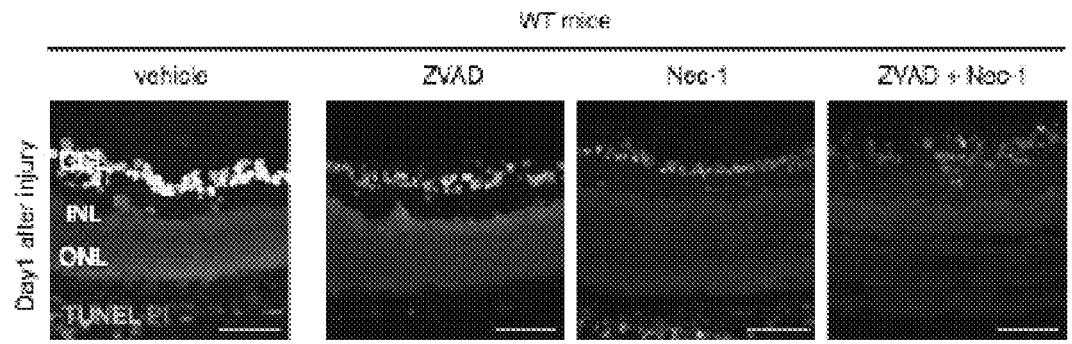
FIGS. 3A-3G provide photographs and graphs showing TUNEL-positive cells (FIG. 3A and FIG. 3B), Brn3B-positive cells (FIG. 3C and FIG. 3D), IPL thickness (FIG. 3E), GCL and IPL thickness (FIG. 3F and FIG. 3G) in Z-VAD and/or Nec-1 treated mice that underwent ON injury at day one.
Figure 3B:
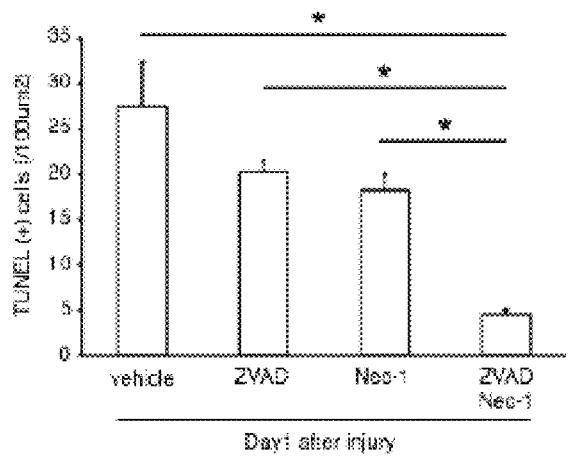
Figure 3C:
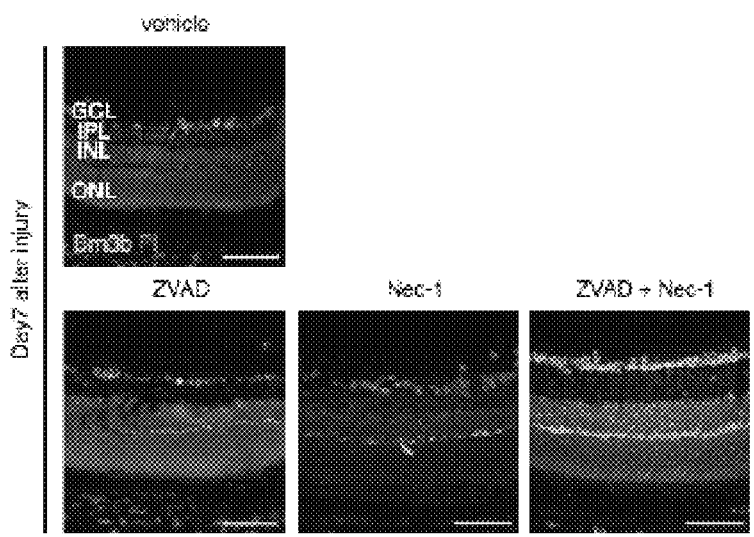
Figure 3D:
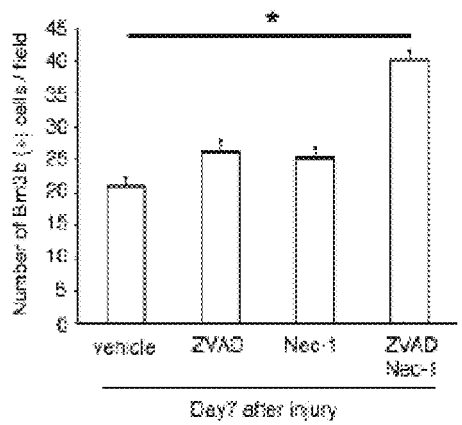
Figure 3E:
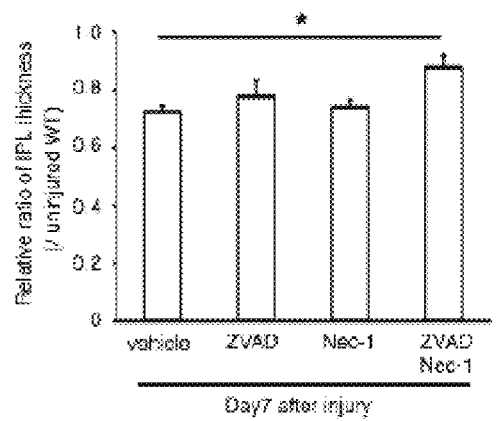
Figure 3F:
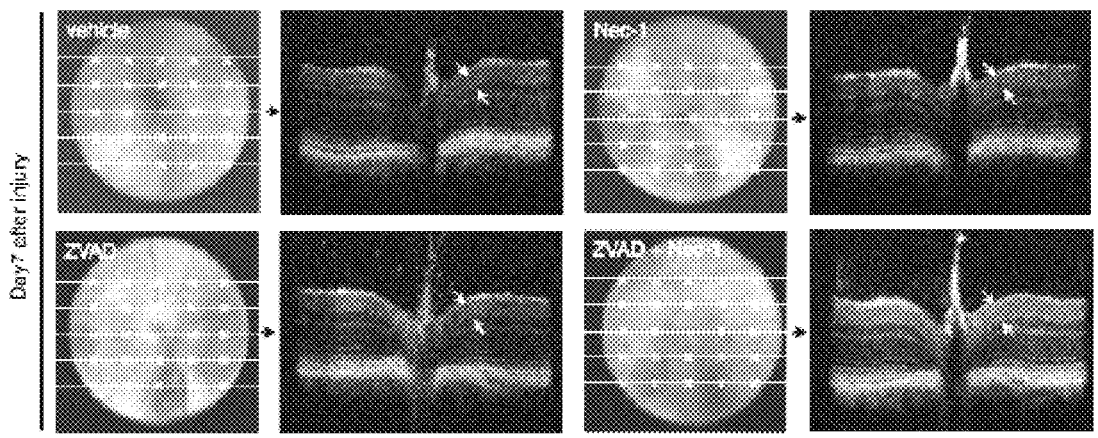
Figure 3G:
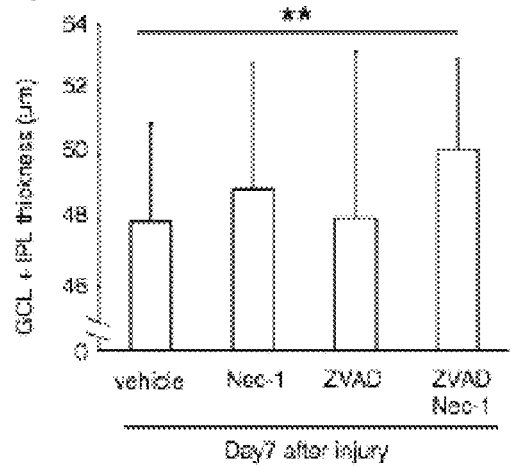
Figure 3H:
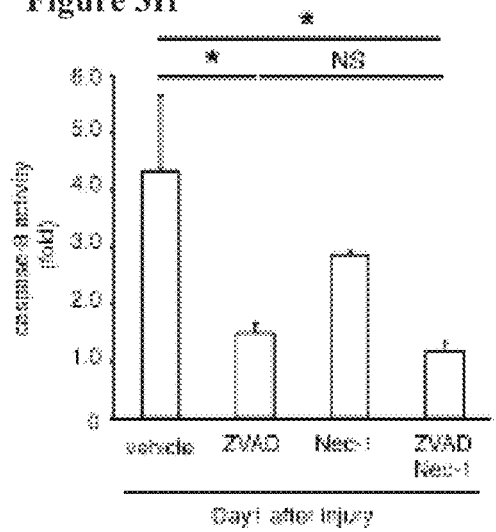
FIGS. 3H-3J provide photographs and graphs showing caspase-8 (FIG. 3H), caspase-9 (FIG. 3I and FIG. 3K) and caspase-3 (FIG. 3J and FIG. 3K) expression in Z-VAD and/or Nec-1 treated mice that underwent ON injury one day after injury.
Figure 3I:
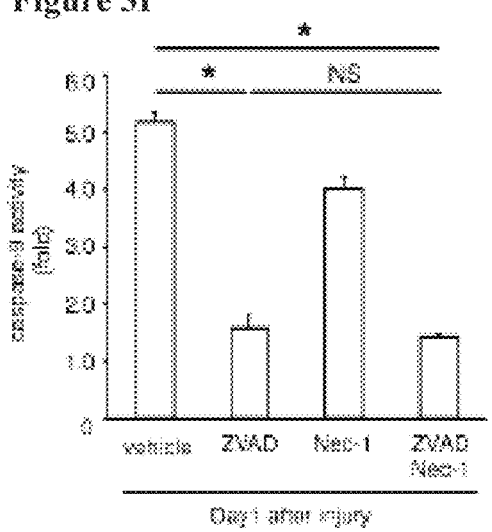
Figure 3J:
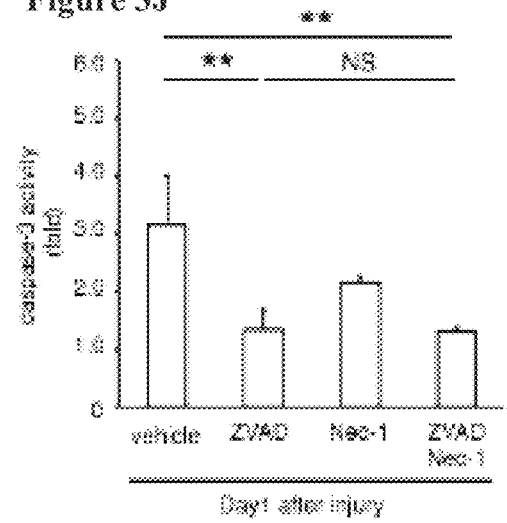
Figure 3K:
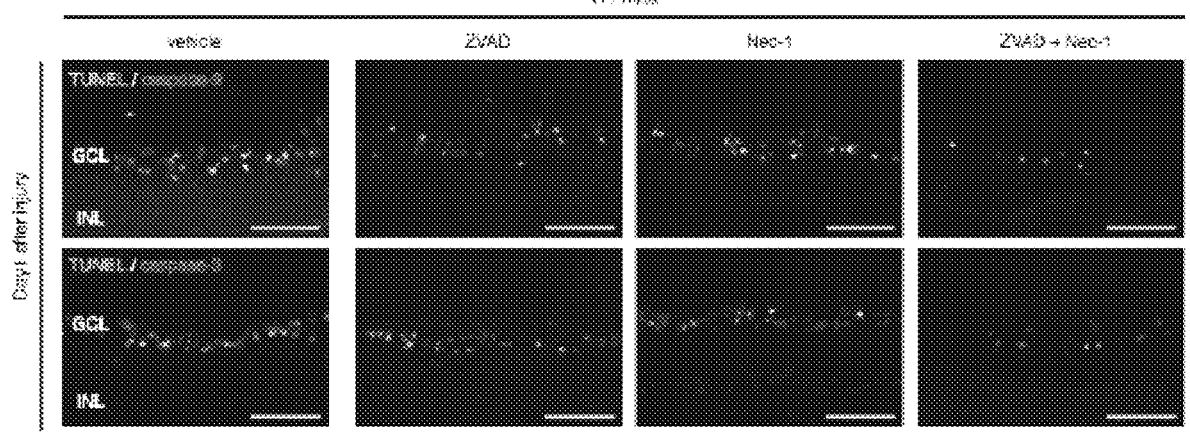
FIG. 3L provide a graph showing TNF-α expression in Z-VAD and/or Nec-1 treated mice that underwent ON injury one day after ON injury.
FIGS. 3M-3Q provide photographs and graphs showing TUNEL-positive cells (FIG. 3M and FIG. 3N), Brn3B-positive cells (FIG. 3O and FIG. 3P), and IPL thickness (FIG. 3Q) in Z-VAD and/or Nec-1 treated mice that underwent ON injury at day one, day three, or day 7 after ON injury.
FIG. 3R provides a graph showing caspase-3, caspase-8, and caspase-9 activities in the retina one day after ON injury (n=6, *p<0.01). The caspase activities were normalized to non-injured retina.
Figure 3L:
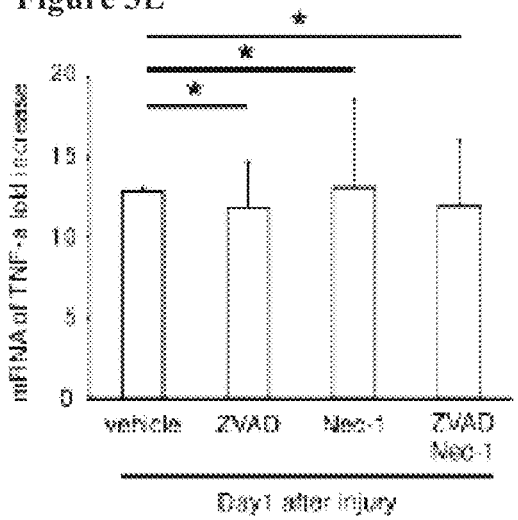
Figure 3M:
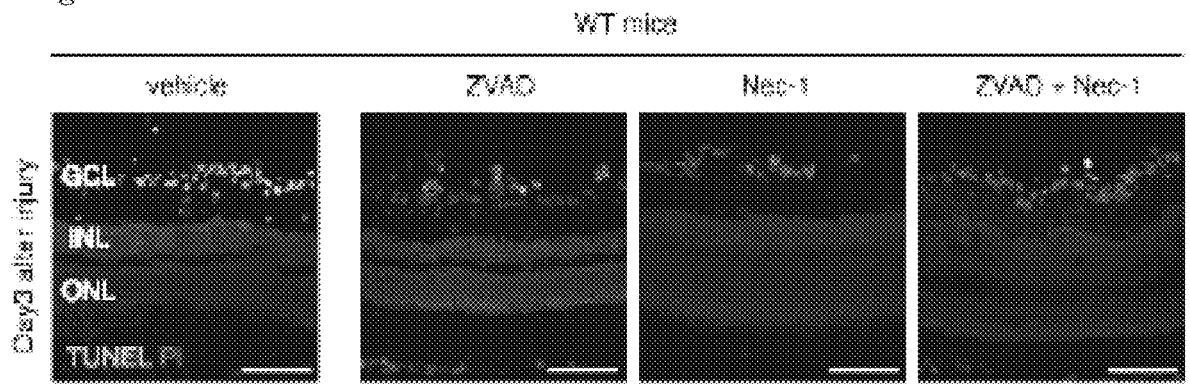
Figure 3N:
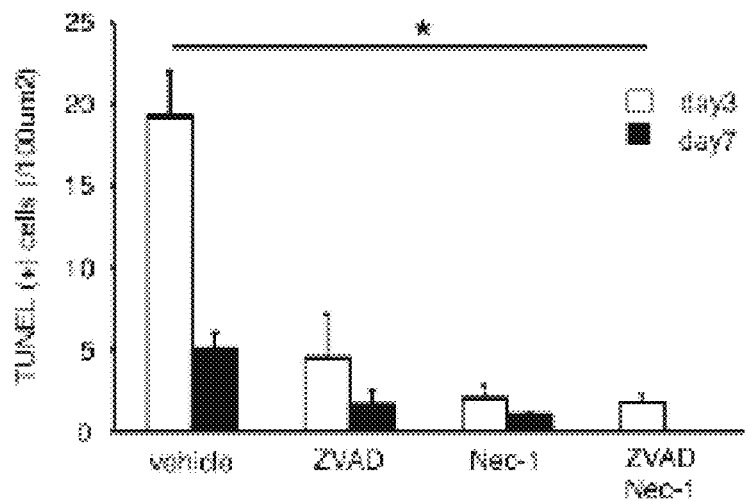

By day one after ON injury, there was a dramatic decrease in apoptotic RGCs in mice that received a combination of Z-VAD and Nec-1 (FIGS. 3A and 3B). Injection of Nec-1 alone, did not affect the number of TUNEL positive cells (FIGS. 3A and 3B), which declined significantly at day three and day seven after ON injury (FIGS. 3M and 3N).

Figure 3O:
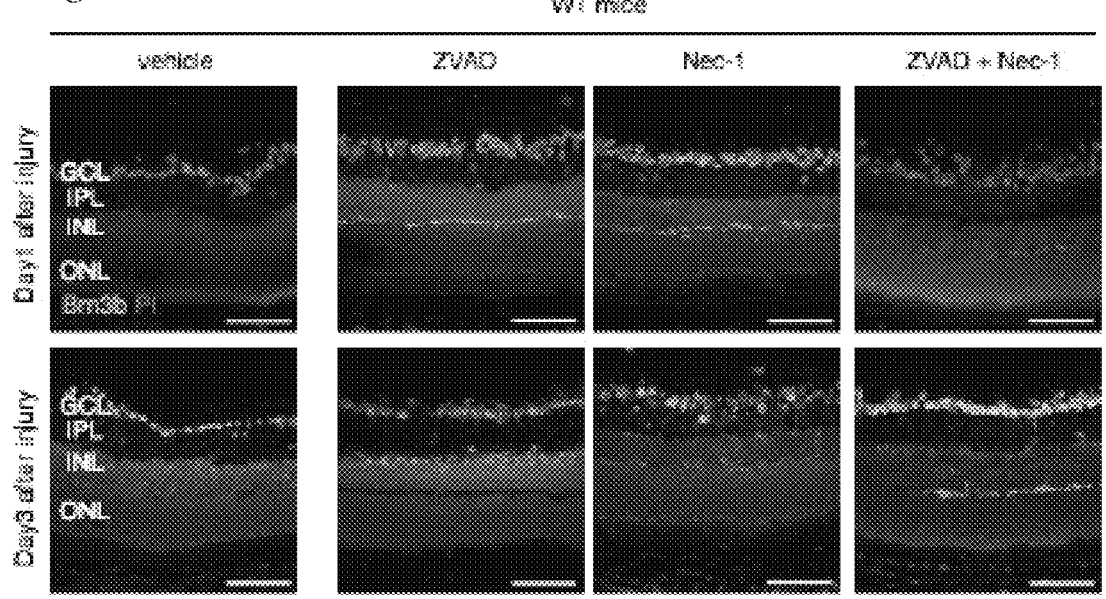
Figure 3P:
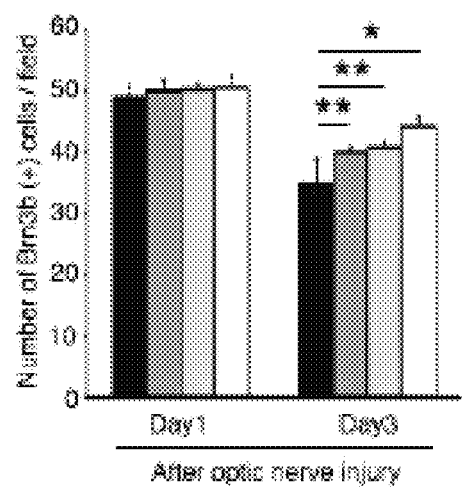

Immunohistochemistry was performed to assess the number of remaining viable RGCs using an antibody against the specific RGC marker Brn3b. Although TUNEL positive cells peaked at day one after injury, significant decrease in RGC number was first observed on day three (FIGS. 3O and 3P). One week after ON injury, the number of Brn3b positive cells in the vehicle group was decreased by approximately 50% compared to the group that received a combination of Z-VAD with Nec-1 (FIGS. 3C and 3D).

Figure 3Q:
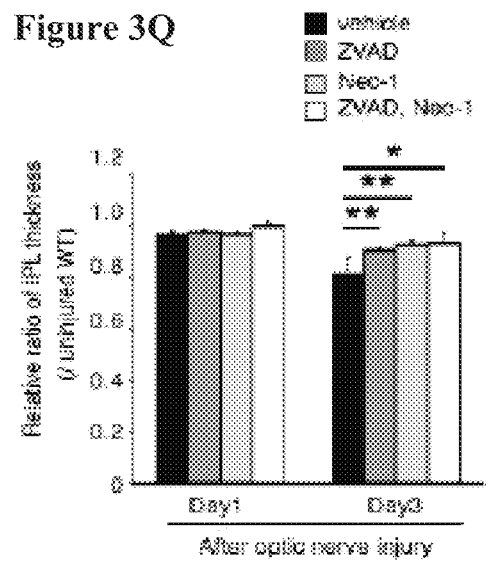
Figure 3R:
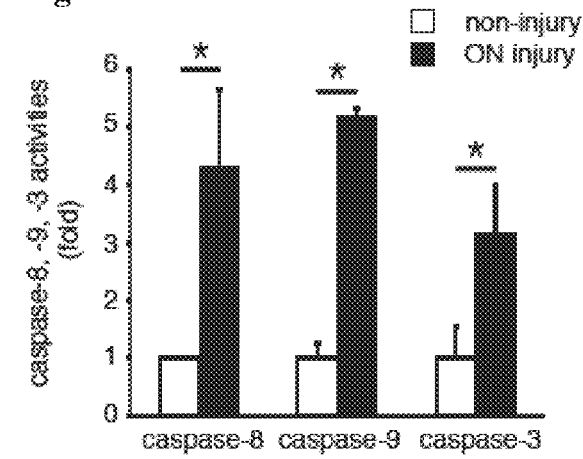

Inner plexiform layer (IPL) thickness and ganglion cell layer (GCL) with IPL thickness (location of RGC cell bodies and axons) were measured using immunohistochemistry and a Spectral Domain Optical Coherence Tomography (SD-OCT) system (Bioptigen Inc., Durham, N.C.). Mice were positioned on a custom cassette, which allowed three-dimensional free rotation and alignment of the mouse eye for imaging. Hydration with normal saline was used to preserve corneal clarity. A volume analysis centered on the ON head was performed, using 100 horizontal, raster, and consecutive B-scan lines, each one composed by 1200 A-scans. The thickness of GCL+IPL was assessed at 500 µm, 400 µm, 300 µm distance from the ON head (nasally and temporally) as well as at 200 µm, 400 µm above and below the ON head. Co-administration of Z-VAD and Nec-1 remarkably reversed the decrease in IPL thickness (FIG. 3Q) and GCL with IPL thickness that was seen in the vehicle group (FIGS. 3E-3G). Taken together, these data suggest that inhibition of RIP kinases together with a broad-spectrum caspase inhibitor are required for effective neuroprotection after ON injury.

D. Broad Caspase Inhibition Shifts Cell Death from Apoptosis to Necrosis

Figure 4A:
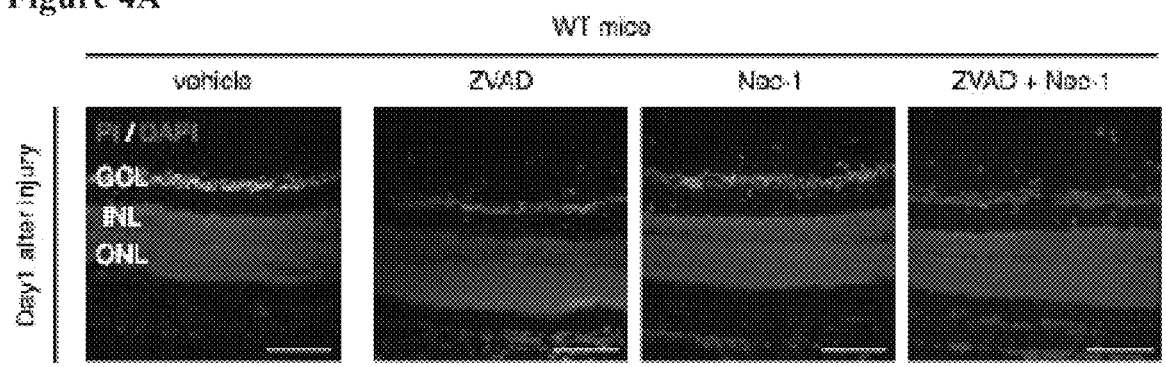
FIGS. 4A-4B provide a photograph of PI staining (FIG. 4A) and graph (FIG. 4B) showing quantification of PI-positive cells in ZVAD and/or Nec-1 treated mice that underwent ON injury.
Figure 4B:
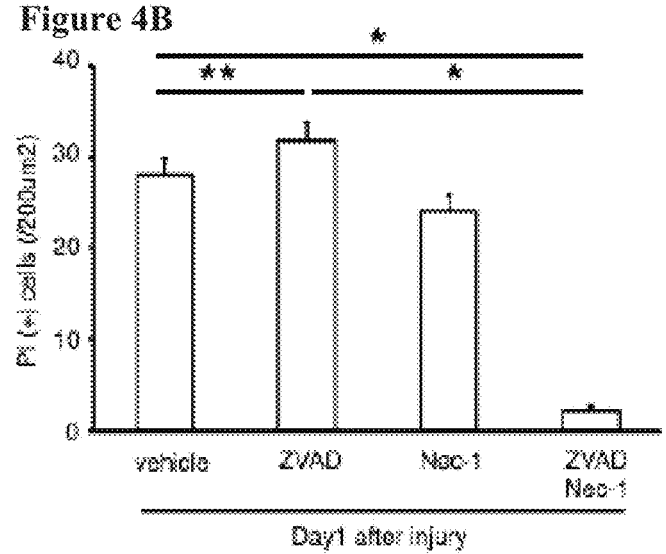

To investigate further the underlying mechanism of why Z-VAD fails to prevent RGC death after ON injury, propidium iodide (PI) was used to detect necrotic cells in GCL (Unal Cevik et al., (2010)). At one day after ON injury, Z-VAD administration increased the number of PI positive cells compared with vehicle (FIGS. 4A and 4B). In comparison, the number of PI positive cells was significantly decreased after Nec-1 co-administration (FIGS. 4A and 4B). These results provide direct evidence that Z-VAD treatment shifts RGC death from apoptotic to necrotic death.

In addition, the morphology of RGC death was assessed by transmission electron microscopy (TEM) as previously described (Trichonas et al., (2010) PROC NATL ACAD SCI USA)). Specifically, the eyes were enucleated, and the posterior segments were fixed in 2.5% glutaraldehyde and 2% paraformaldehyde in 0.1 M cacodylate buffer with 0.08 M $CaCl_2$ at 4° C. The eyes were post-fixed for 1.5 hours in 2% aqueous OsO4, dehydrated in ethanol and water, and embedded in EPON. Ultrathin sections were cut from blocks and stained with saturated, aqueous uranyl acetate and Sato's lead stain. The specimens were observed with a Philips CM10 electron microscope. More than 50 RGCs per eye were photographed and subjected to quantification of cell death in a masked fashion. RGCs showing cellular shrinkage and nuclear condensation were defined as apoptotic cells, and RGCs associated with cellular and organelle swelling and discontinuities in nuclear and plasma membrane were defined as necrotic cells. Electron dense granular materials were labeled simply as end-stage unclassified cell death. Autophagosome was defined as a double- or multi-membraned structure containing cytoplasmic material and/or organelles, and autolysosome was defined as cytoplasmic vesicle containing electron dense degraded material, as previously described (Eskelinen, 2008).

Figure 4C:
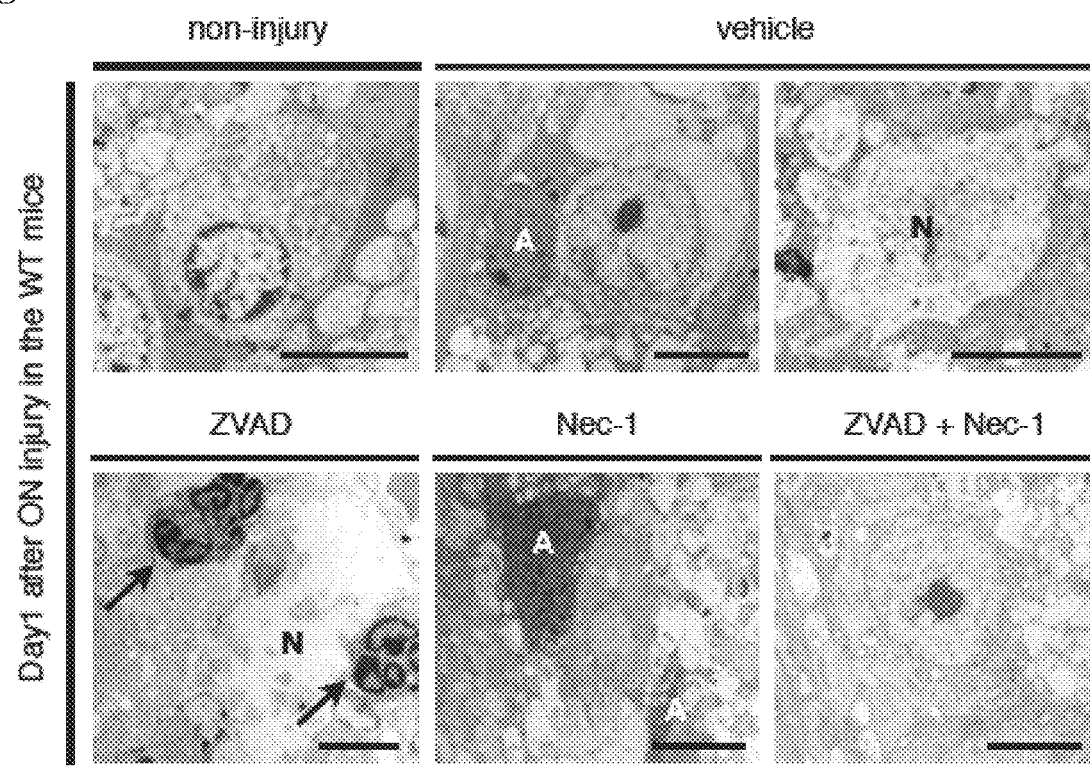
FIGS. 4C-4D provide (FIG. 4C) TEM photographs of RGCs one day after ON injury and (FIG. 4D) quantification of apoptotic and necrotic RGC death.
Figure 4D:
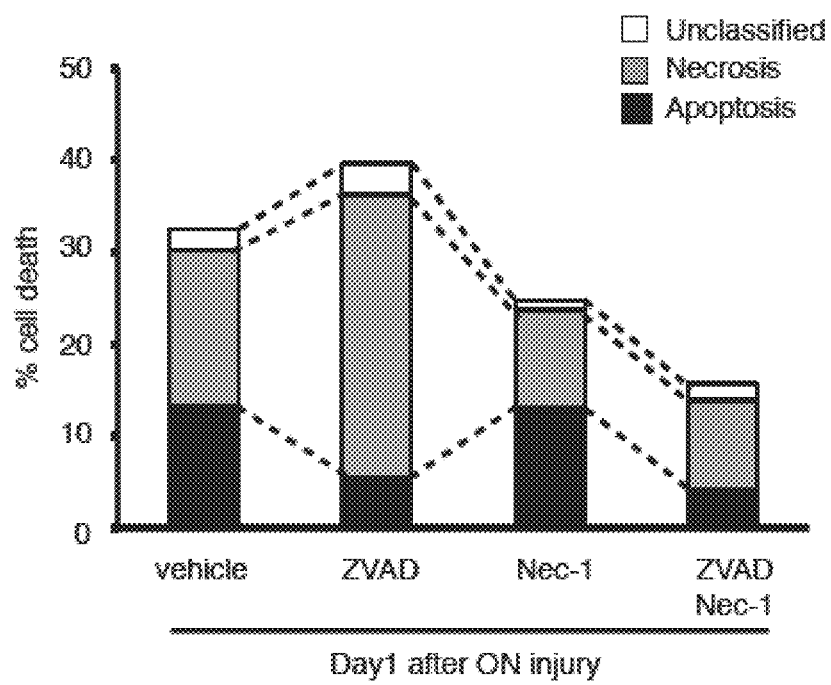

RGC death was categorized into apoptosis, necrosis and unclassified end-stage of death, as previously described (Trichonas et al., (2010) PROC NATL ACAD SCI USA). Consistent with the PI study, at one day after ON injury, both apoptotic and necrotic RGC death was observed in the vehicle-treated retina (apoptotic cells: 13.4±5.8%, necrotic cells: 16.9±4.2%, unclassified: 2.2±2.4%; FIGS. 3A and 3B). Nec-1 treatment slightly decreased necrotic RGC death (% apoptotic cells: 13.0±8.4%, necrotic cells: 10.6±2.6%, unclassified: 1.0±1.8%; FIGS. 4C and 4D). In contrast, ZVAD treatment significantly decreased apoptotic RGC death, while it increased necrotic cell death without reducing overall cell loss (% apoptotic cells: 5.6±3.4%, necrotic cells: 30.7±4.9%, unclassified: 3.4±2.3, P<0.01; FIGS. 4C and 4D). Further, infiltration of inflammatory cells was more prevalent in ZVAD-treated retina (FIG. 4C). Co-administration of ZVAD and Nec-1 led to a substantial decrease of both apoptotic and necrotic RGC death (% apoptotic cells: 4.2±5.1%, necrotic cells: 9.8±6.6%, unclassified: 1.8±1.8%, P<0.01; FIGS. 4C and 4D).

These results demonstrate that RIP1 kinase mediated necrosis is an important pathway of RGC death in addition to apoptosis and compensates for blockage of caspase-dependent apoptosis after ON injury.

E. RIP3 Deficiency Attenuates RGC Loss after ON Injury

Figure 5A:
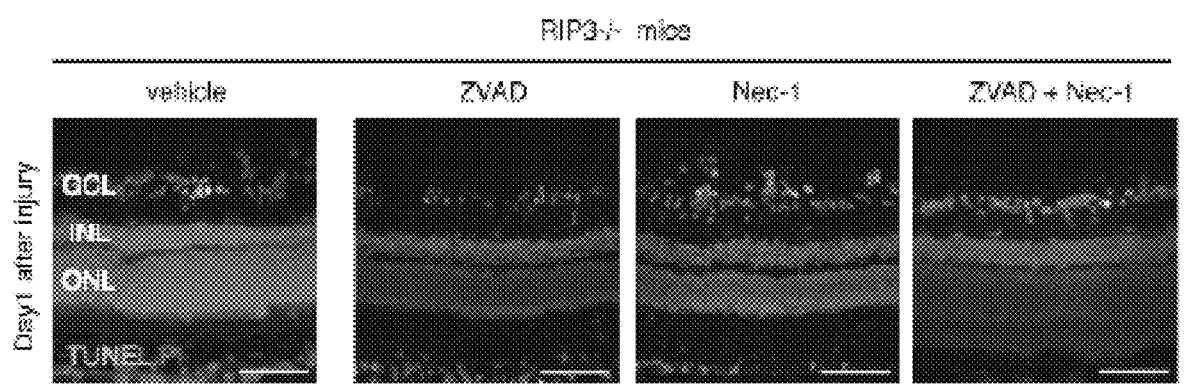
FIGS. 5A-5G provide photographs and graphs showing TUNEL-positive cells (FIG. 5A and FIG. 5B), Brn3B-positive cells (FIG. 5C and FIG. 5D), IPL thickness (FIG. 5E), and PI-positive cells (FIG. 5F and FIG. 5G) in Z-VAD and/or Nec-1 treated RIP3−/− mice that underwent ON injury.
Figure 5B:
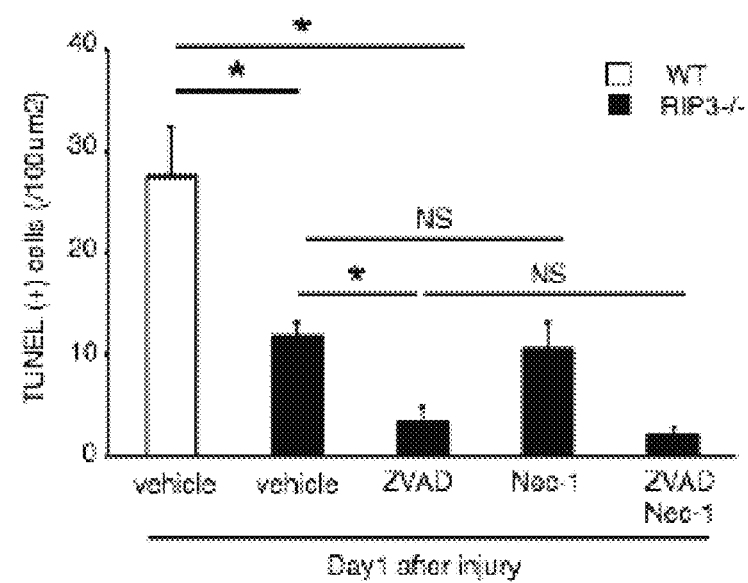

To further elucidate the role of RIP kinase pathway in RGC death after ON injury, RIP3 deficient mice were used (He et al., (2009) CELL 137:1100-1111, Zhang et al., (2009) SCIENCE 325:332-336)), because RIP1$^{-/-}$ mice die postnatally at day 1-3 (Kelliher et al., (1998) IMMUNITY 8:297-303)). At one day after ON injury, RIP3$^{-/-}$ mice exhibited significantly less TUNEL positive cells 1 day compared to wildtype controls (FIGS. 5A and 5B). Z-VAD administration in RIP3$^{-/-}$ mice lead to a marked decrease in TUNEL positive cells compared to wild type and RIP3$^{-/-}$ mice that received vehicle solution. Moreover, Nec-1 co-administration in RIP3$^{-/-}$ mice did not have any additional effect, whereas administration by itself did not have any effect at all (FIGS. 5A and 5B).

Figure 5C:
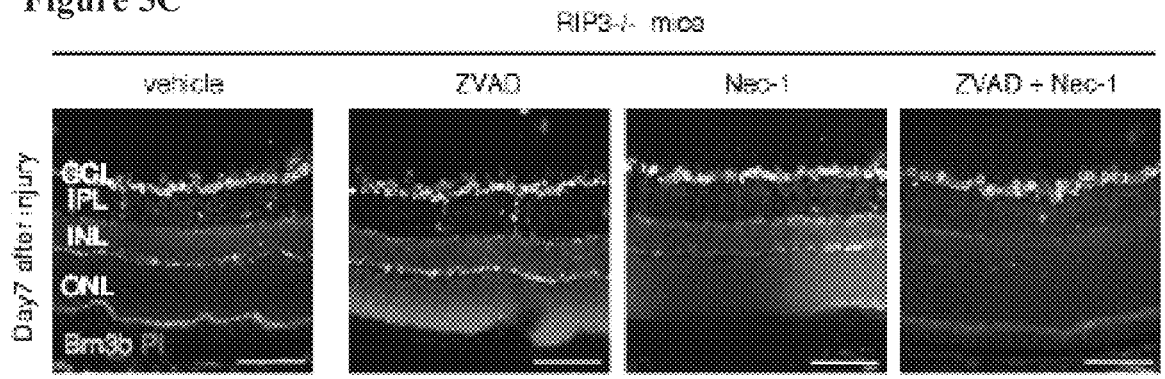
Figure 5D:
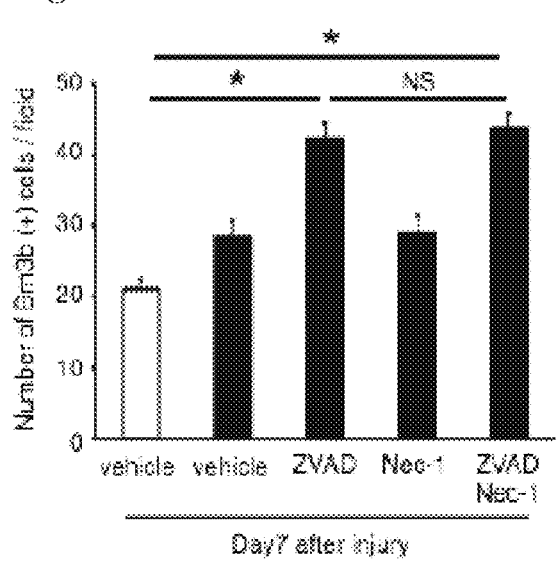
Figure 5E:
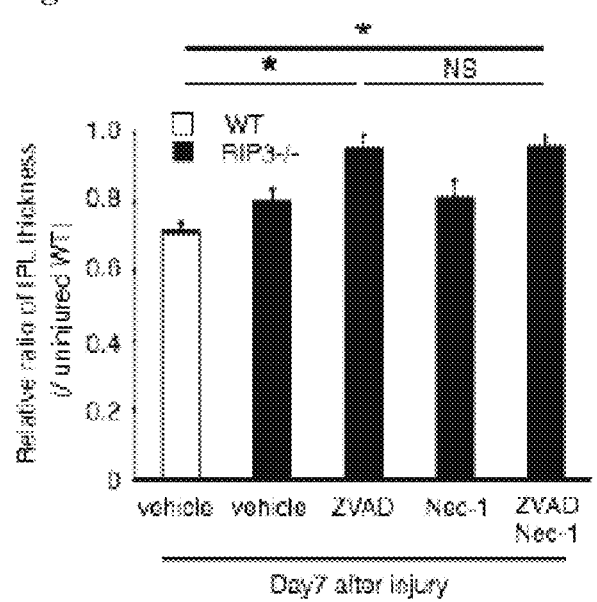

The number of viable RGCs were assessed by Brn3b immunohistochemistry and measurement of IPL thickness. Seven days after ON injury, RIP3$^{-/-}$ mice (vehicle, black box) demonstrated increased number of Brn3b positive cells compared to wildtype mice, (vehicle, white box) which was further enhanced with Z-VAD administration (FIGS. 5C and 5D). At one week after ON injury, RIP3 deficiency combined with Z-VAD administration also resulted in preservation of IPL thickness compared to RIP3$^{-/-}$ mice that received only vehicle solution (FIGS. 5C and 5E). The number of Brn3b positive cells and IPL thickness did not alter after Nec-1 coadministration (FIGS. 5C-5E).

Figure 5F:
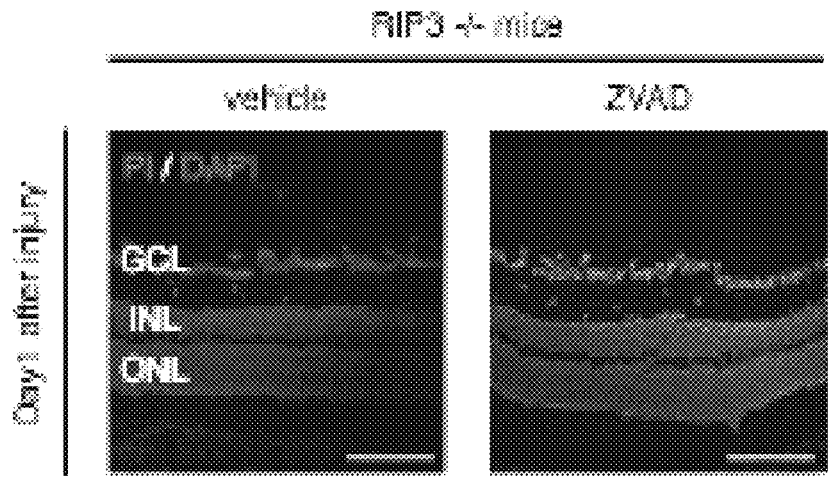
Figure 5G:
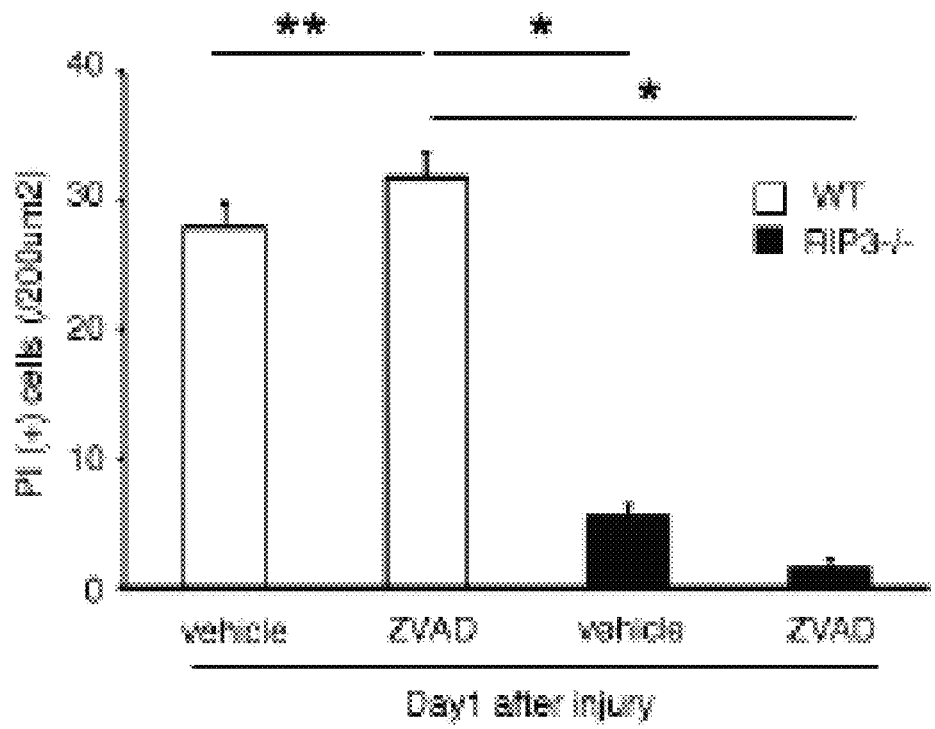

To investigate whether RIP3 deficiency can prevent the switch from apoptotic to necrotic RGC death after Z-VAD treatment, PI staining was performed. PI staining shows the number of cells with disrupted plasma membrane. RIP3 deficient mice exhibited significantly less PI positive cells compared with Z-VAD treated WT mice (FIGS. 5F and 5G). This result suggests that RIP3 kinase plays an essential role in ON injury-induced programmed necrosis, especially in the presence of caspase inhibitor.

F. Inhibition of Caspase and RIP Kinase Prevents RGC Death after NMDA Injury

Figure 6A:
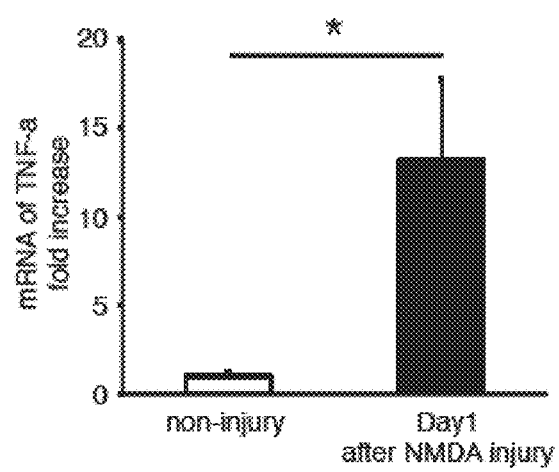
FIGS. 6A-6H provide photographs and graphs showing TNF-α mRNA level (FIG. 6A; n=6, *p<0.01) and RIP3 and RIP1 mRNA and protein levels (FIG. 6B, FIG. 6C, and FIG. 6D; n=6, *p<0.01, **p<0.05), TUNEL-positive cells (FIG. 6E and FIG. 6F; n=8, *p<0.01), Brn3B-positive cells (FIG. 6G; n=8, **p<0.05), and IPL thickness (FIG. 6H), in RIP3−/− mice that underwent NMDA-induced ON injury. Bars for FIG. 6E and FIG. 6G are 100 µm. GCL; retinal ganglion cell layer, INL; inner nuclear layer, ONL; outer nuclear layer.
Figure 6B:
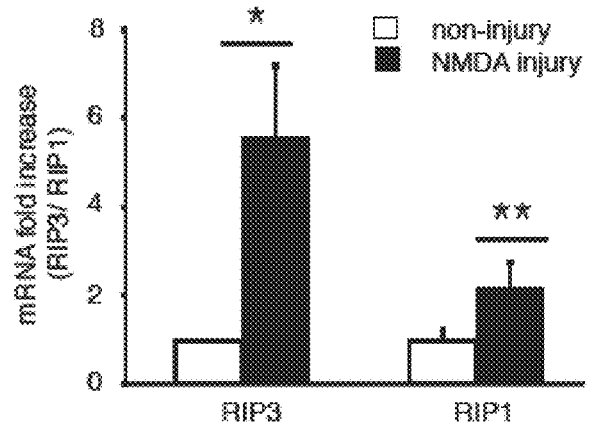
Figure 6C:
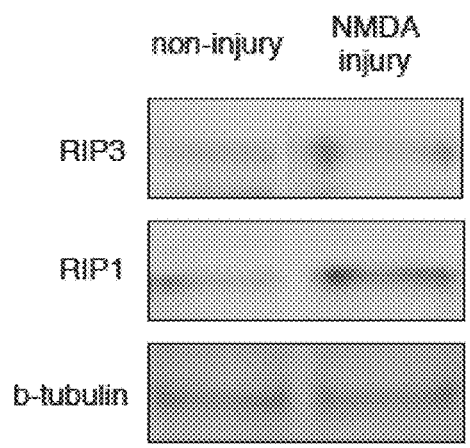
Figure 6D:
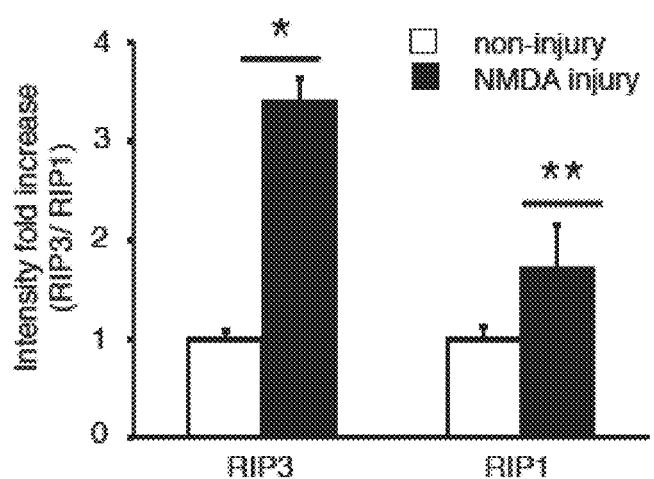
Figure 6E:
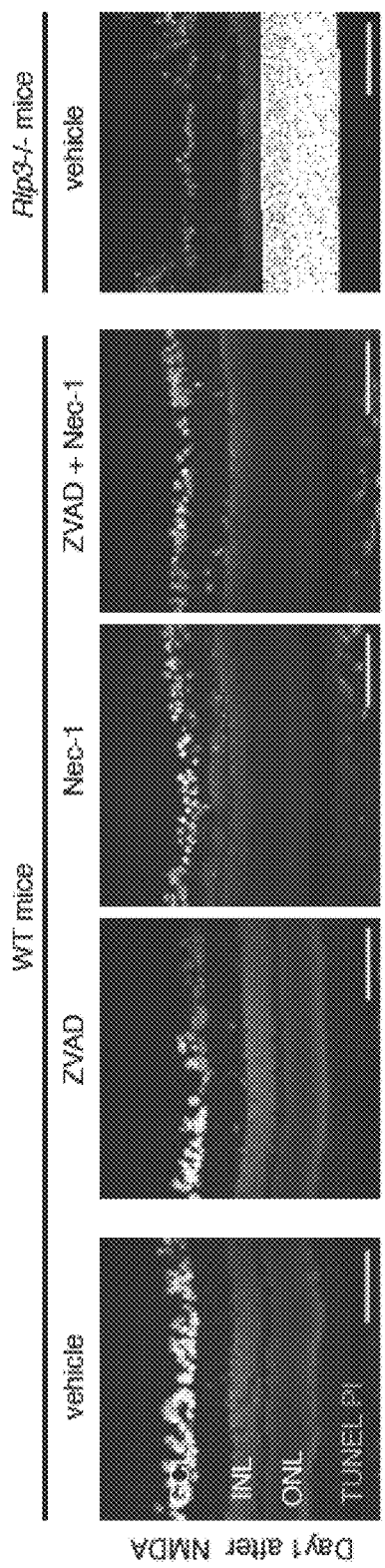
Figure 6F:
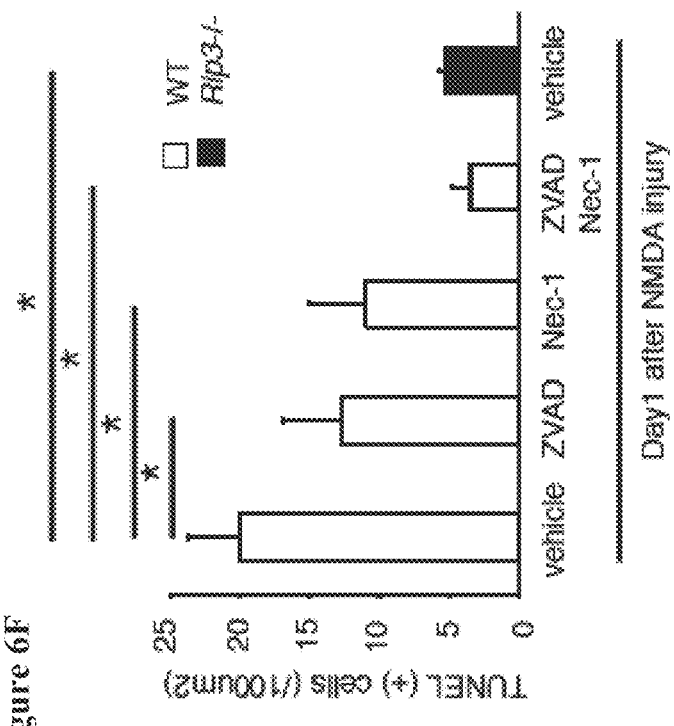
Figure 6G:
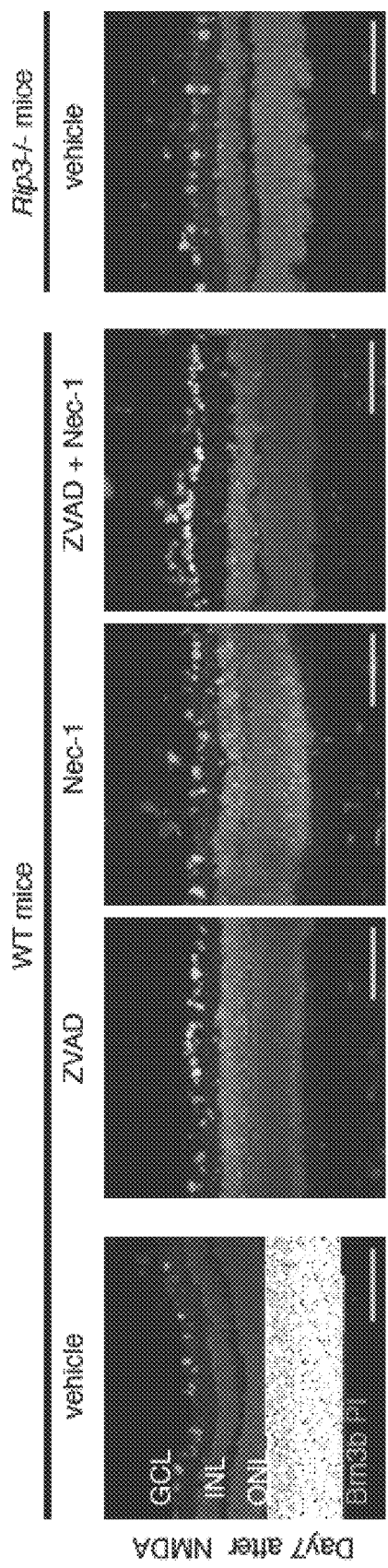
Figure 6H:
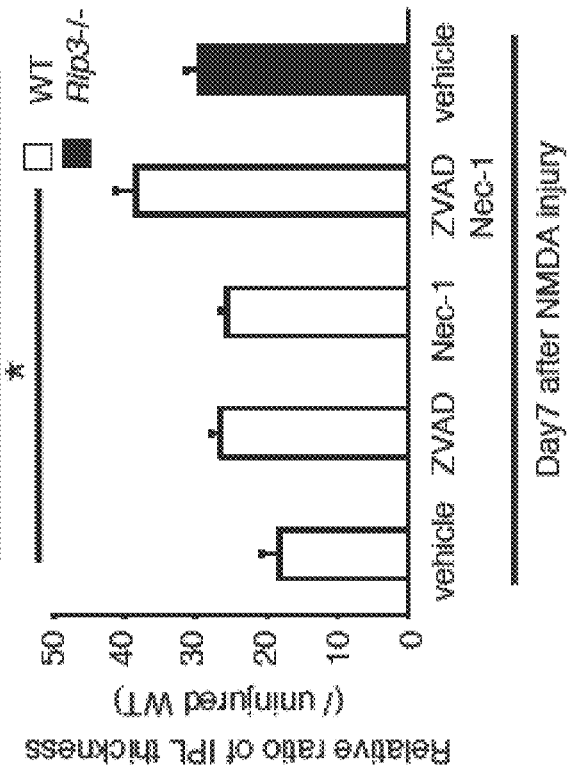

Glutamatergic excitotoxicity has been implicated as a mechanism of RGC death in glaucoma (Dreyer et al., (1996) ARCH OPHTHALMOL 114:299-305)) and intravitreous N-methyl-D-aspartate (NMDA) injection is used as an excitotoxic RGC insult model (Libby et al., (2005) PLoS GENET 1:17-26)), which is a different model of glaucoma compared to the ON injury model discussed above. To investigate the role of caspases and RIP kinases in another model of RGC death, we examined the effect of ZVAD plus Nec-1 in the NMDA injury model. Consistent with results of the ON injury model, TNF-α mRNA levels increased at 1 day after NMDA injury over 10-fold compared with non-injured mice (FIG. 6A). Quantitative real-time PCR and Western blot analyses revealed that expressions of RIP3 and RIP1 after NMDA injury were up-regulated compared with those in non-injured retina (FIGS. 6B-6D). Treatment with ZVAD or Nec-1 alone decreased the number of TUNEL positive cells and prevented the reduction of Brn3b positive cells, and these protective effects were further enhanced by co-administration of ZVAD plus Nec-1 (FIGS. 6E-6H). Rip3 deficiency also decreased RGC loss after NMDA injury (FIGS. 6E-6H). These results suggest that caspase and RIP kinase pathways are critical inducers of RGC death in NMDA injury as well as ON injury.

Figure 7A:
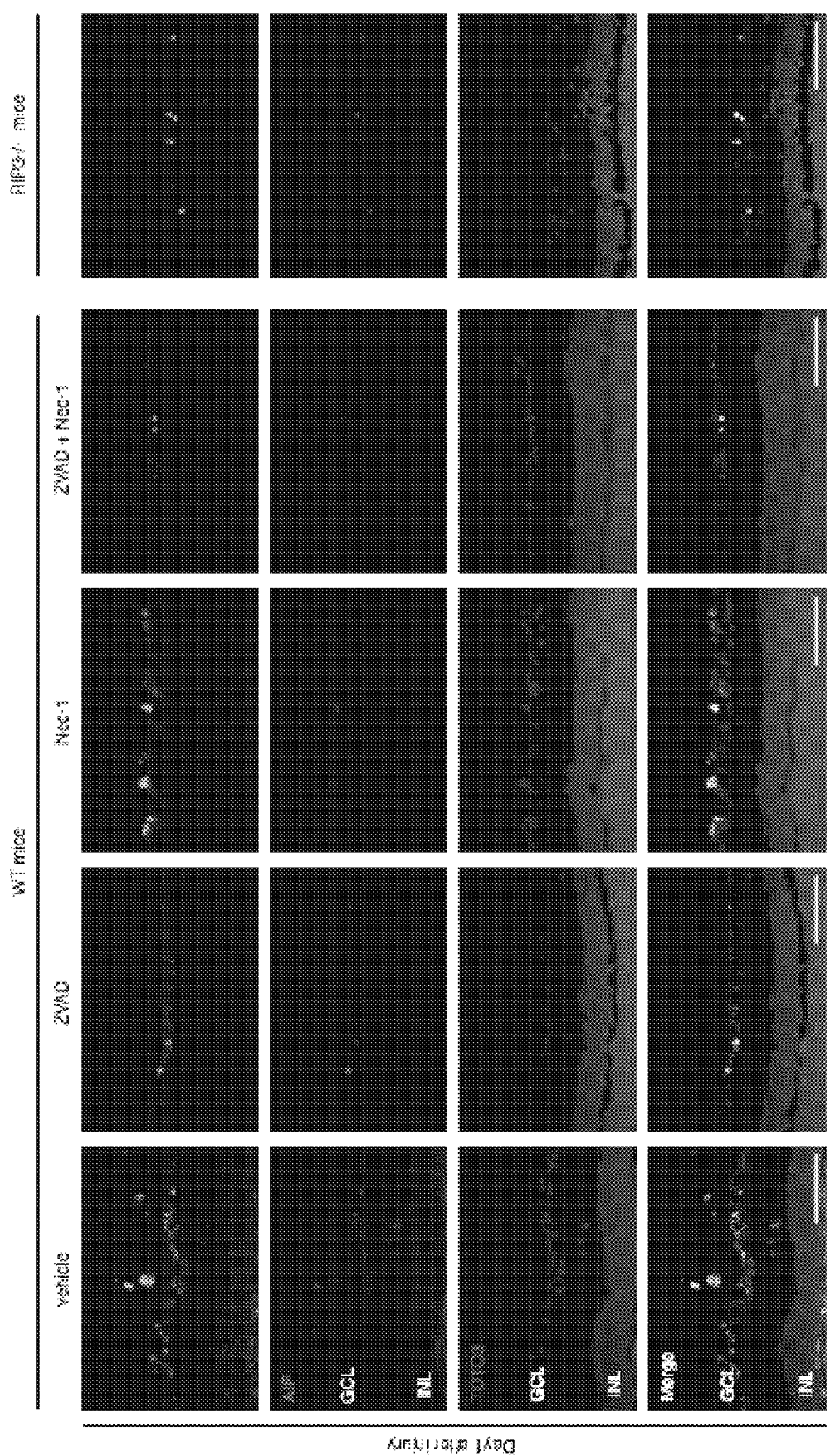
FIGS. 7A-7B provide a photograph and graph showing AIF translocation following Z-VAD and/or Nec-1 treatment in wildtype or RIP3−/− mice.
Figure 7B:
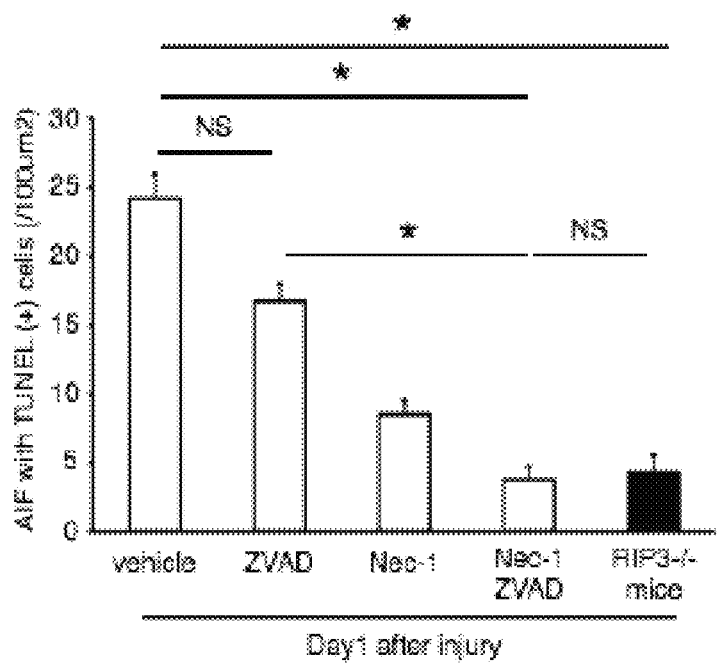
Figure 7C:
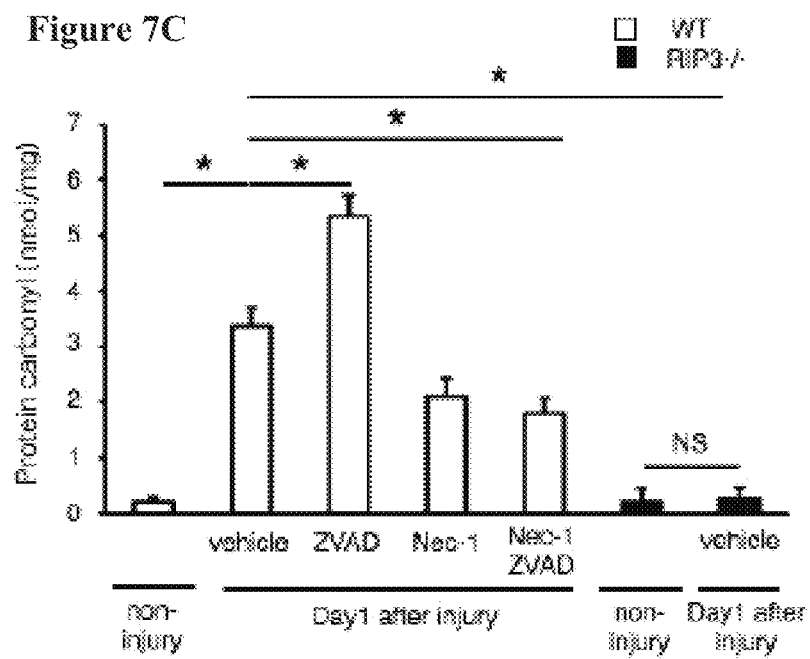
FIG. 7C provides a graph showing ROS production in wildtype or RIP3−/− mice.

G. RIP Kinases Mediate Apoptosis-Inducing Factor (AIF) Nuclear Translocation after ON Injury Apoptosis inducing factor (AIF) is a mitochondrial flavoprotein which is involved in initiating caspase-independent apoptosis. After loss of mitochondrial membrane potential, AIF translocates into the nucleus, induces DNA fragmentation and peripheral chromatin condensation (Susin et al., (1999), Susin et al., (2000), Candé et al., (2004)). To analyze whether mitochondrial release of AIF is associated with RGC death after ON injury, immunostaining for AIF was performed together with TUNEL assay. One day after ON injury, there was a prominent nuclear translocation of AIF, which was not affected by pan-caspase inhibition (FIGS. 7A and 7B). In contrast, co-administration of Z-VAD with Nec-1 or RIP3 deficiency substantially prevented nuclear translocation of AIF (FIGS. 7A and 7B). These results indicate that AIF is heavily involved in RGC death after ON injury and RIP kinases play a crucial role in its nuclear translocation.

Figure 9A:
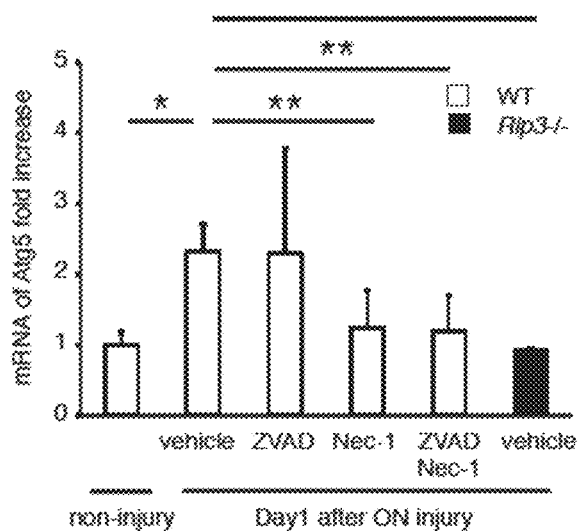
FIGS. 9A-9C provide graphs showing Atg5 (FIG. 9A), Atg7 (FIG. 9B), and Atg12 (FIG. 9C) expression after ON injury, as determined by quantitative real-time PCR analysis.
Figure 9B:
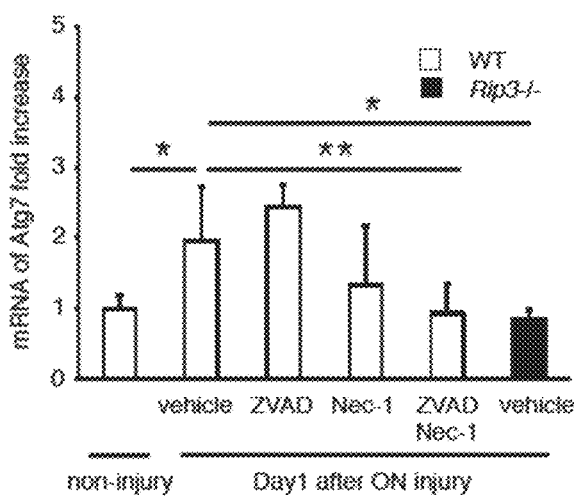
Figure 9C:
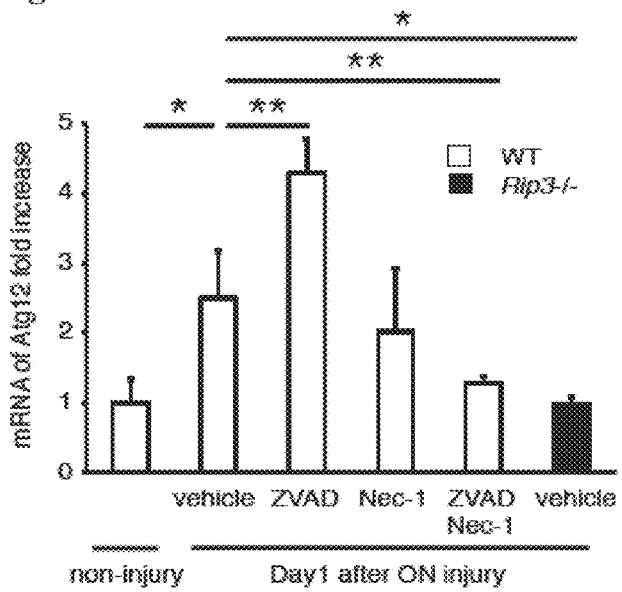

It has been reported that RIP kinases control ROS generation during programmed necrosis (Cho et. al., (2009) CELL 137:1112-1123, Zhang et al., (2009) SCIENCE 325:332-336)). To investigate whether ROS play a roll in oxidative retinal damage after ON injury, protein level of carbonyl contents was analyzed using ELISA using the OxiSelect™ Protein Carbonyl ELISA Kit (Cell Biolabs, San Diego, Calif.). One day after ON injury, carbonyl contents dramatically increased in the treatment of Z-VAD group compared with vehicle group (FIG. 9C). In contrast, no increase in carbonyl contents was seen with mice co-administered with Z-VAD and Nec-1 or with RIP3$^{-/-}$ mice (FIG. 9C). These results indicated that RIP kinases have a crucial role of AIF translocation into nuclear via ROS production.

H. Ultrastructural Changes of RGCs after ON Injury

It is widely accepted that cell death occurs through the morphologically distinct processes of apoptosis, necrosis, or autophagic cell death (Kroemer et al., (2009) CELL DEATH DIFFER 16:3-11)). Apoptosis is characterized by activation of caspases, DNA fragmentation, and membrane blebbing (Kroemer et al., (2009) CELL DEATH DIFFER 16:3-11, Yi et al., (2009)), whereas necrosis is characterized by swelling of the endoplasmic reticulum, mitochondria, and cytoplasm, with subsequent rupture of the plasma membrane and lysis of the cells (Kroemer et al., (2009) CELL DEATH DIFFER 16:3-11, Festjens et al., (2006)). Although TUNEL has been used traditionally as a marker of apoptosis, a previous report has shown that necrosis, programmed or otherwise, also yields DNA fragments that react with TUNEL in vivo, rendering it difficult to distinguish between apoptosis and necrosis (Grasl-Kraupp et al., (1995) HEPATOLOGY 21:1465-1468)).

Figure 8A:
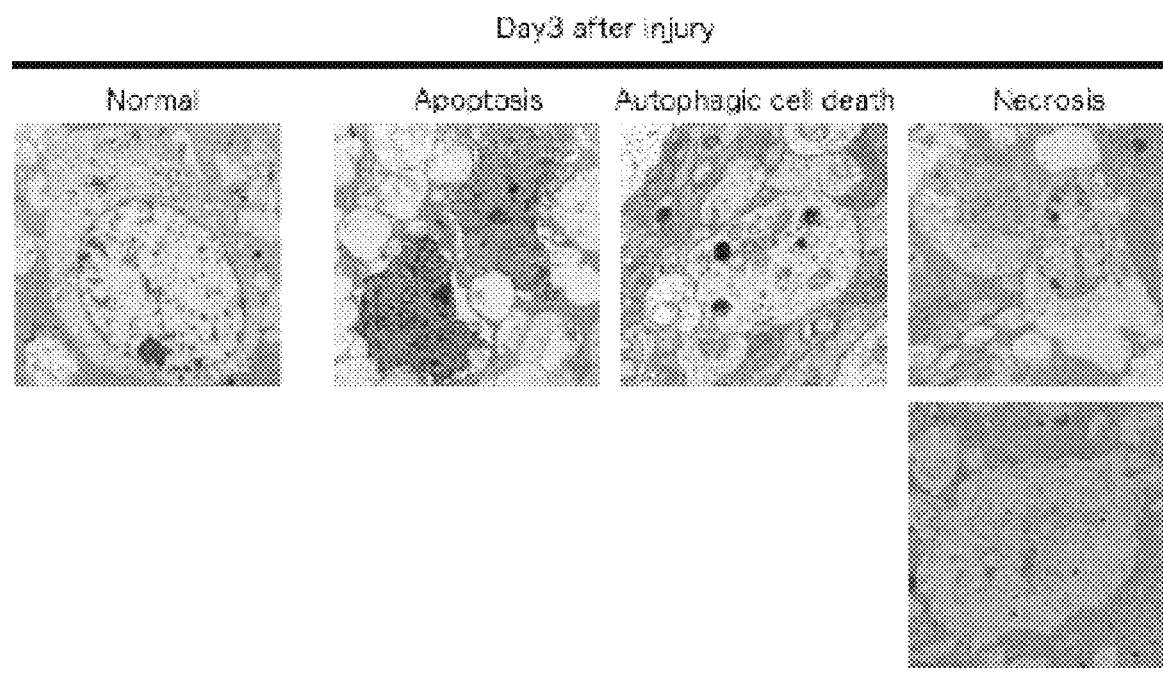
FIG. 8A-8B provide transmission electron microscope (TEM) photomicrographs depicting RGCs after ON injury.
Figure 8B:
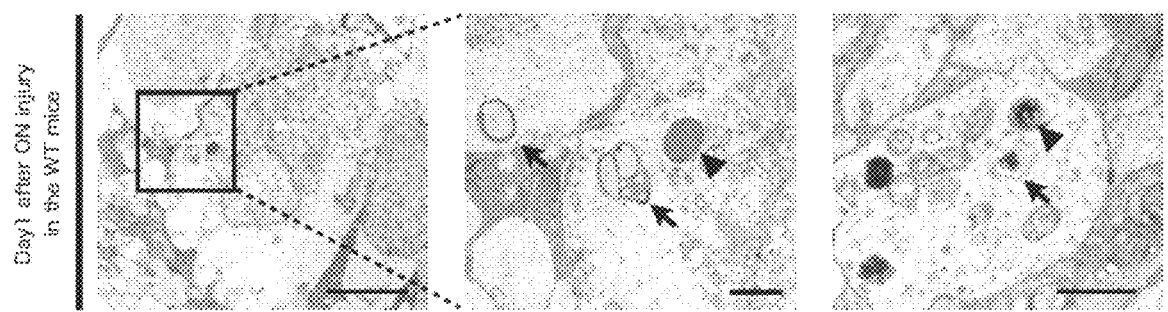

To identify the RGC death mode seen after ON injury transmission electron microscopy (TEM) studies was performed as previously described. RGCs that were unable to be classified were defined as end-stage cell death/unclassified. Under normal conditions, RGCs had a well-defined continuous plasma membrane, and a non-uniform distribution of organelles in the cytoplasm, with maximum concentration in the perinuclear region. RGCs contained tubular sacs of rough endoplasmic reticulum (rER) surrounded by large numbers of ribosomes (Nissl bodies). Mitochondria were identified as round or oval double-membrane structures with characteristic cristae. In addition, the cytoplasm contained elements of Golgi apparatus (GA), free ribosomes and microtubules sectioned at various angles. A large round nucleus, surrounded by a double-layered nuclear membrane, contained homogeneously dispersed karyoplasm (chromatin material) and one or two electron dense nucleoli (FIG. 8A) (Saggu et al., (2010) BMC NEUROSCI 11:97)). After ON injury, RGC death through apoptosis was predominant. As can be seen in FIG. 8B, autophagosomes and autolysosomes were observed especially in necrotic cells with cellular swelling (FIG. 8B).

Administration of Z-VAD blocked apoptotic cell death and sensitized cells to necrotic cell death. Nec-1 treatment did not influence the ratio of apoptotic to necrotic death. In comparison, co-administration of Nec-1 with Z-VAD prevented the switch from apoptotic to necrotic cell death; thus, ameliorating RGC loss.

I. RIP Kinases Mediate Autophagic Cell Death after ON Injury

TEM data indicated that autophagic cell death is also involved in RGC death after ON injury. Autophagic cell death is recognized by the formation of autophagosomes, double-membrane autophagic vacuoles that eventually fuse with lysosomes to form autolysosomes (Levine et al., (2004)). In this type of cell death, the Atg6-Vps34 complex was suggested to be critical for autophagosome-vesicle nucleation (Levine et al., (2005)). Elongation of the autophagosomal membrane formed by the Atg6-Vps34 complex is assisted by two Atg12 and Atg8 ubiquitin-like conjugation systems (Ichimura et al., (2000)). Atg12, activated by Atg7, covalently attaches to Atg5, forming the irreversible conjugate.

To investigate whether autophagy influences RGC death after ON injury, expression of several genes critical for autophagosome formation including Atg5, 7 and 12 was measured by quantitative RT-PCR. These transcripts were found to be up-regulated 2.0- to 2.5-fold at one day after ON injury (FIGS. 9A-9C). ZVAD administration further increased Atg12 expression compared with vehicle treatment (FIG. 9C). In contrast, administration of ZVAD plus Nec-1, or Rip3 deficiency suppressed expression of Atg5, 7 and 12 transcripts (FIGS. 9A-9C).

Figure 9D:
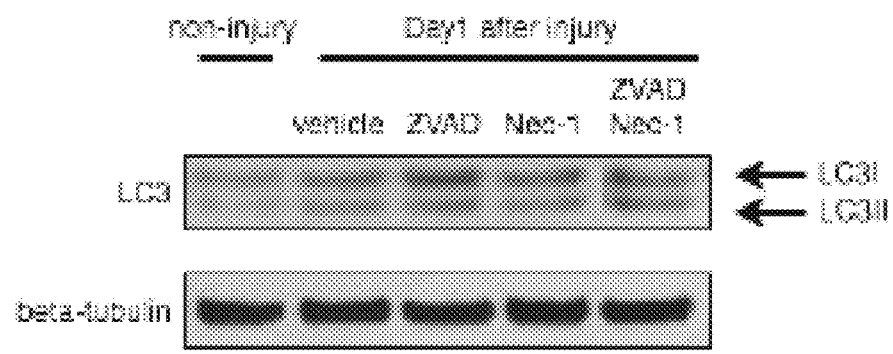
FIGS. 9D-9E provide photographs showing LC3 protein levels and immunostaining at one day after ON injury.

Protein levels of LC3, an autophagy marker, were also assessed by western blot analysis. In the vehicle, LC3-II, an isoform associated with autophagy activity (Kabeya et al, 2000), was up-regulated by approximately 30% compared with non-injured mice. Consistent with results from the quantitative PCR analysis, protein level of LC3-II increased more than vehicle following Z-VAD administration (FIG. 9D).

Figure 9E:
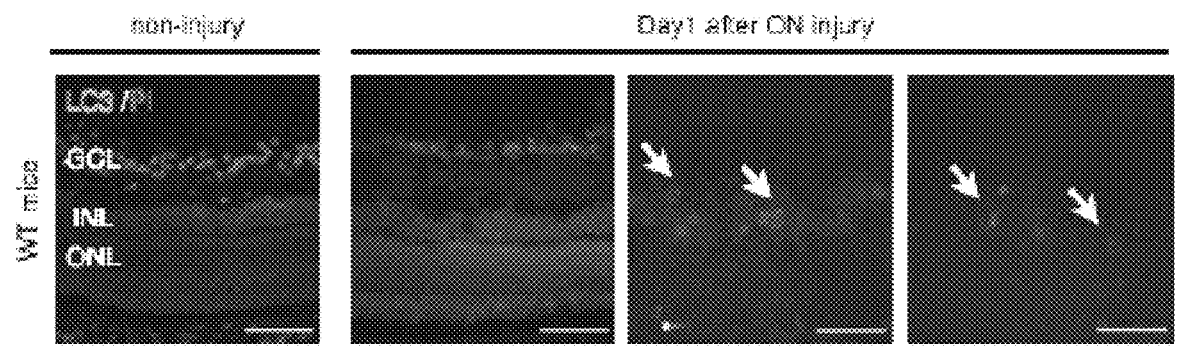

Immunohistochemistry was performed to confirm the localization of LC3. In the non-injured retina, expression of LC3 showed faintly detectable staining (FIG. 9E). However, some LC3 positive cells were detected in the GCL one day after ON injury (FIG. 9E).

Together, these findings indicate that autophagosome formation increases in RGCs after ON injury and part of this process may be associated with RIP1 kinase-mediated necrosis. This is consistent with previous reports which showed that inhibition of autophagic cell death rescues cell death (Yu et al., (2004) SCIENCE 304:1500-1502, Knoferle et al., (2010) PROC NATL ACAD SCI USA 107:6064-6069)).

Figure 10A:
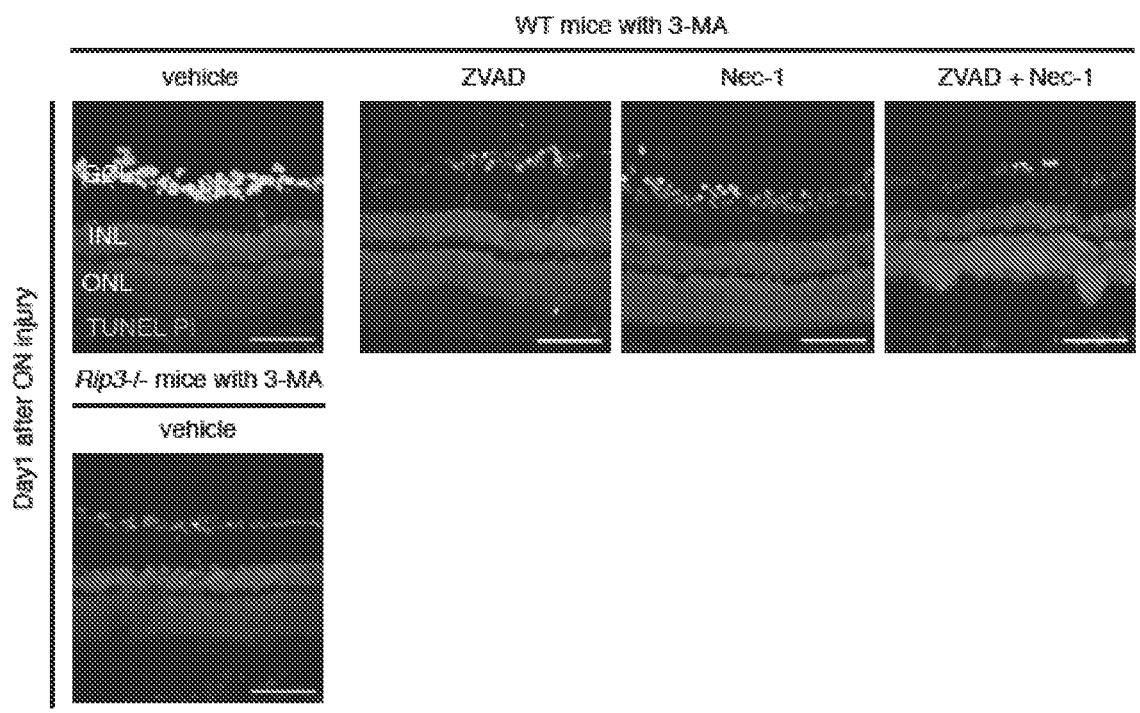
FIGS. 10A-10D provide photographs and a graph showing TUNEL-positive cells (FIG. 10A and FIG. 10B) and Brn3b-positive cells (FIG. 10C and FIG. 10D) in mice that were treated with 3-MA.
Figure 10B:
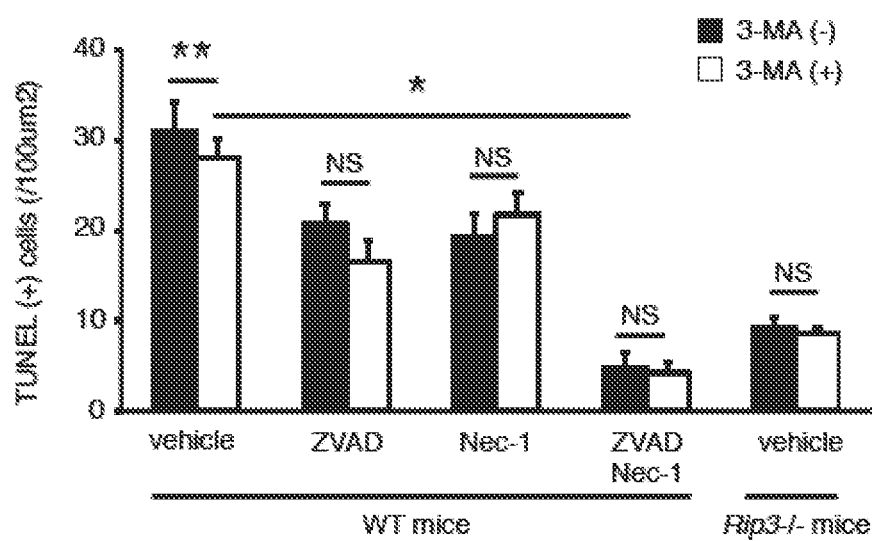
Figure 10C:
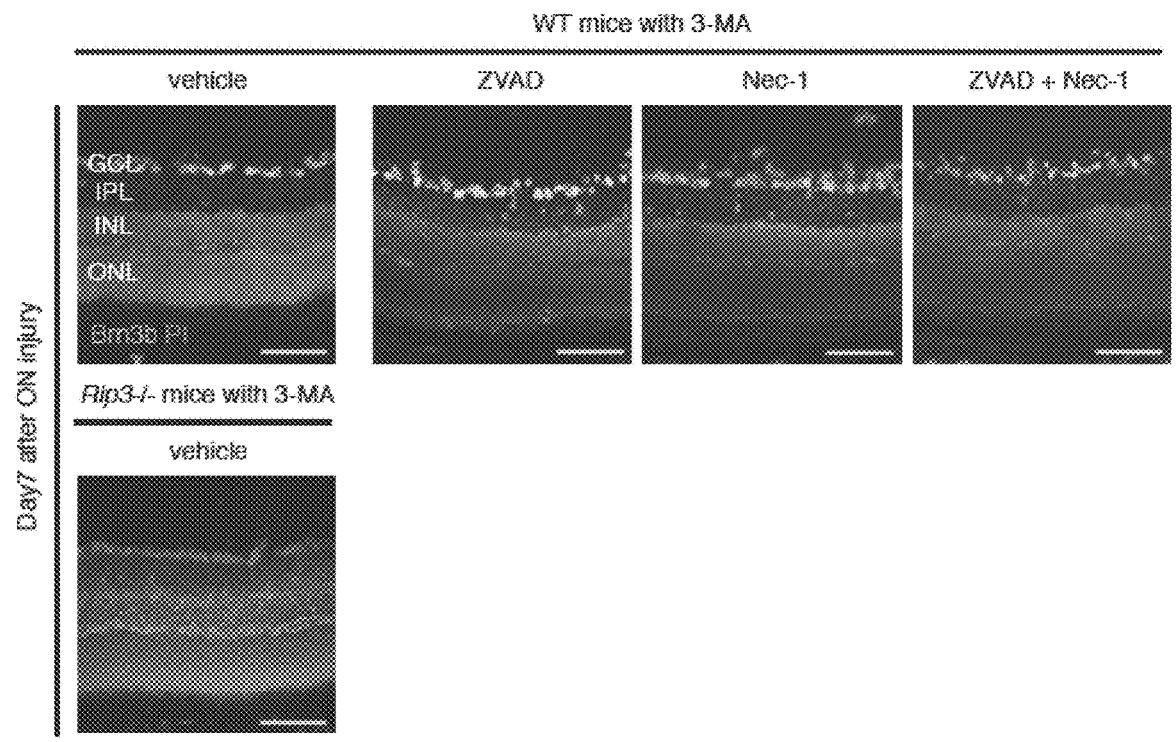
Figure 10D:
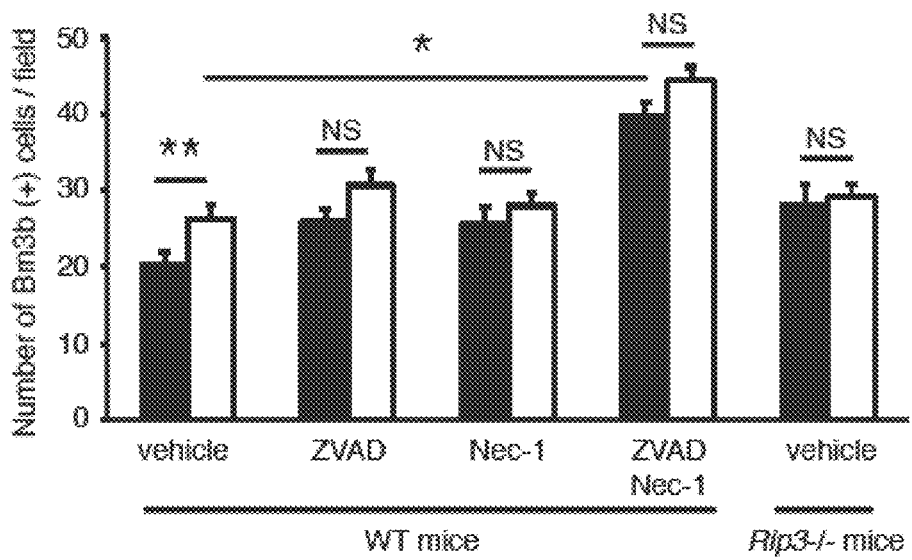
Figure 10E:
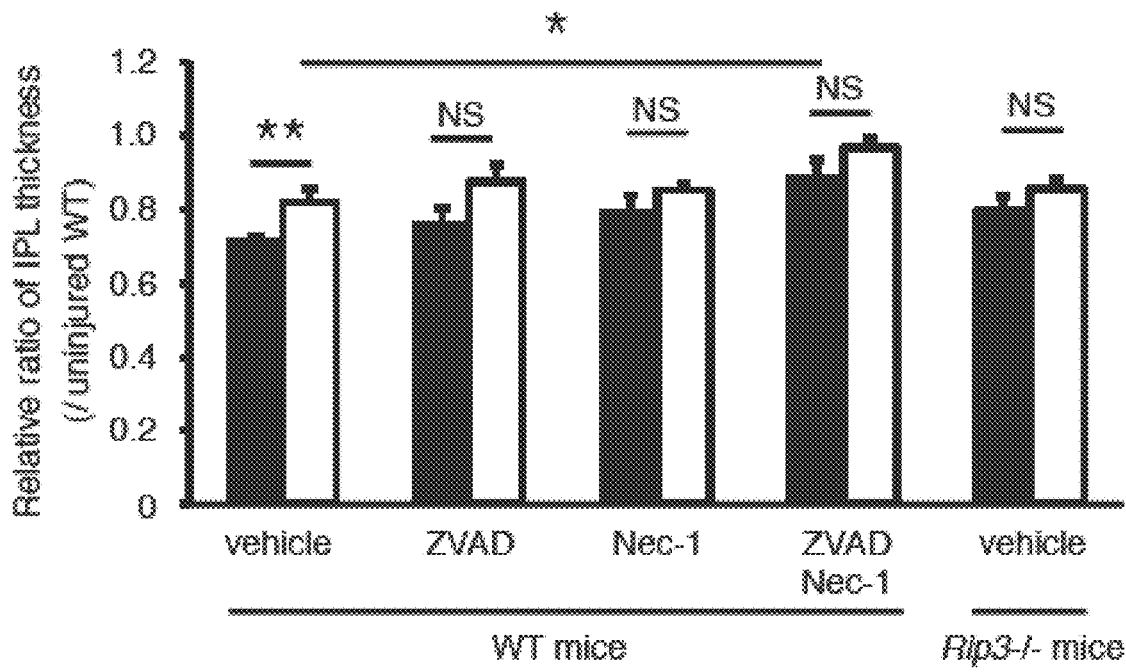
FIGS. 10E-10F provide graphs depicting IPL thickness (FIG. 10E) and carbonyl contents in mice that were treated with 3-MA (FIG. 10F).
Figure 10F:
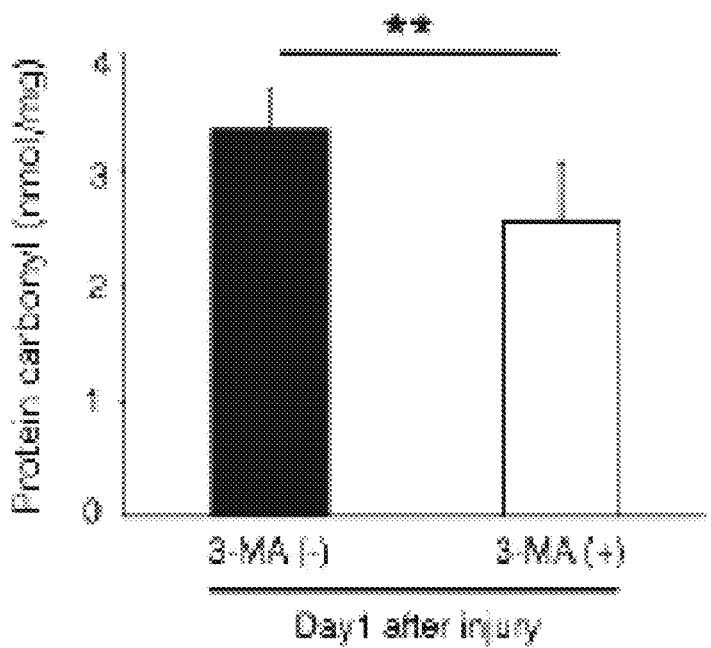

J. Inhibitor of Autophagic Cell Death Partially Suppressed RGCs Death after ON Injury To investigate the role of autophagy in RGC death after ON injury, we examined the effect of 3-methyladenine (3-MA) on RGCs death after ON injury. 3-MA inhibits autophagosome formation (Seglen and Gordon, (1982) PROC NATL ACAD SCI USA 79:1889-1892)). One day after ON injury, TUNEL assay was performed. The number of TUNEL positive cells had a small but statistically significant decline in mice treated with 3-MA compared to the non-treated mice. In addition, the number of Brn3b positive cells and IPL thickness were also analyzed. At seven days after ON injury, 3-MA treatment significantly prevented the reduction of Brn3b positive cells and IPL thickness ratio, although this effect was less than that of the ZVAD plus Nec-1 combination treatment (FIGS. 10C-10E). To investigate whether ROS play a role in oxidative retinal damage after ON injury, protein level of carbonyl contents was analyzed using an ELISA kit (Cell Biolabs, San Diego, Calif.) according to the manufacturer's instructions. One day after ON injury, carbonyl contents decreased in the 3-MA treated group compared with untreated control (FIG. 10F). Together, these results suggest that RGCs loss was attenuated after ON injury by inhibition of autophagic cell death.

Example 2: Efficacy of a Necrosis Inhibitor and a Pan-Caspase Inhibitor in Promoting RGC Survival and Axon Regeneration Like most pathways in the mature central nervous system, the optic nerve cannot regenerate if injured, leaving victims of traumatic nerve injury or degenerative diseases such as glaucoma with life-long visual losses. This situation can be, at least, partially reversed by enhancing the intrinsic growth state of retinal ganglion cells (RGCs). In this example, the efficacy of necrosis inhibitor and a pan-caspase inhibitor in promoting RGC survival and axon regeneration is investigated using a mouse optic nerve crush model.

A. A Necrosis Inhibitor in Combination with a Caspase Inhibitor Promotes RGC Survival in a Optic Nerve Crush Model Mice were subjected to optic nerve crush surgery. Specifically, animals were anesthetized with an intraperitoneal injection of ketamine (60-80 mg/kg: Phoenix Pharmaceutical, St. Joseph, Mo.) and xylazine (10-15 mg/kg: Bayer, Shawnee Mission, K A). Animals were positioned in a stereotaxic apparatus and a 1-1.5 cm incision was made in the skin above the right orbit. Under microscopic illumination, the lachrymal glands and extraocular muscles were resected to expose 3-4 mm of the optic nerve. The epineurium was slit open along the long axis, and the nerve was crushed 2 mm behind the eye with angled jeweler's forceps (Dumont #5) for 10 seconds, avoiding injury to the ophthalmic artery. Nerve injury was verified by the appearance of a clearing at the crush site, while the vascular integrity of the retina was evaluated by fundoscopic examination. Cases in which the vascular integrity of the retina was in question were excluded from the study.

Following surgery, mice were divided into four groups for treatment: vehicle group, ZVAD group (300 µM; given at day 0, day 3 and day 7 after injury), Nec-1 group (4 mM; given at day 0, day 3 and day 7 after injury), and ZVAD plus Nec-1 group (300 µM and 4 mM, respectively; given either once or at day 0, day 3 and day 7 after injury). Soon after injury, each group received an intravitreal injection (3 µl) with the respective compounds. As a control, one group of mice were injected with Zymosan (12.5 µg/µl), a yeast cell wall preparation, known to stimulate axonal regeneration.

Fourteen days following injection, the number of RGCs were measured by Brn3a staining. Specifically, eyes were enucleated and RGC loss was quantified from histological sections of mouse retina. Images of eight prespecified areas, 2 mm from the optic disc, were captured under fluorescent illumination (2 points/section×4 sections per eye, n=8) using a camera (Nikon E800). Brn3a-positive cells were counted using NIH ImageJ software.

Figure 11:
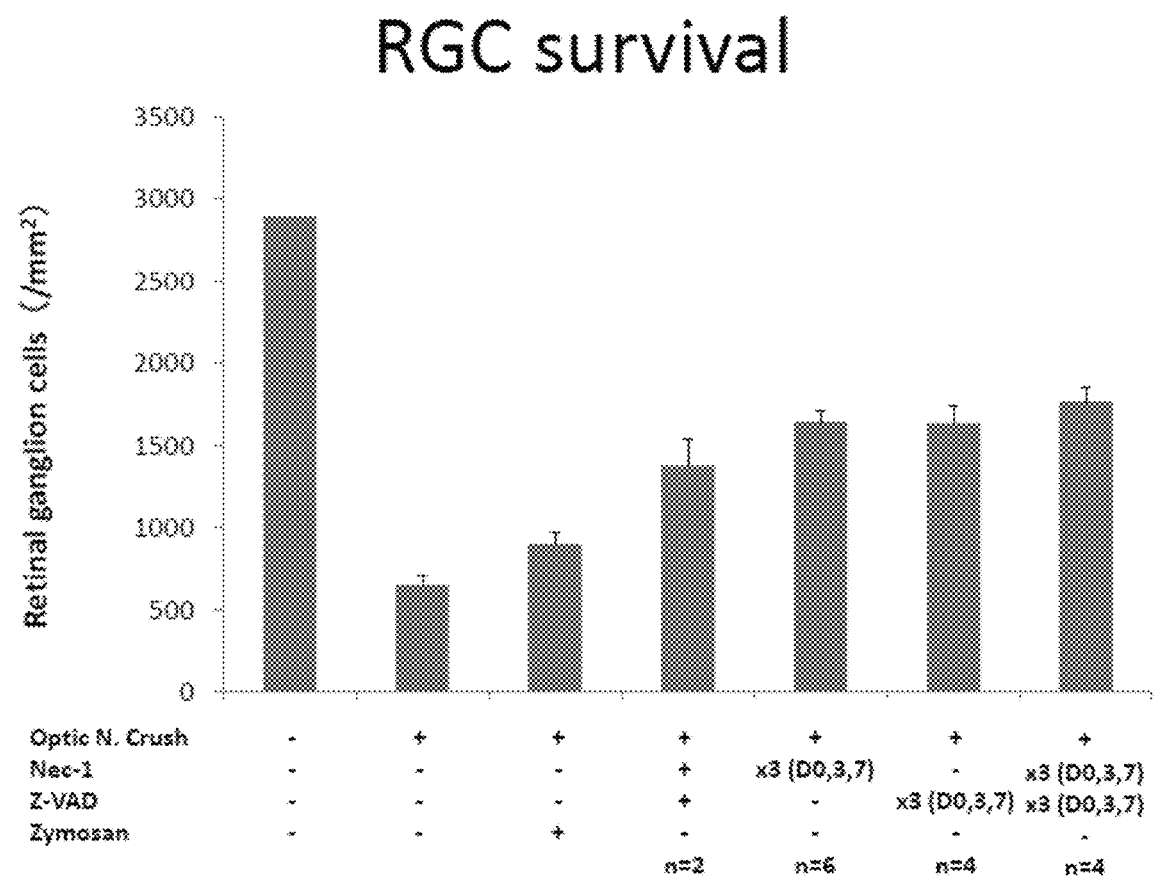
FIG. 11 provides a graph showing RGC survival in mice that were treated with Z-VAD and/or Nec-1 following optic nerve crush injury.

As seen in FIG. 11, a combination of ZVAD and Nec-1 significantly prevented RGC death and promoted RGC survival following optic nerve crush injury when compared to treatment with Zymosan alone (p<0.05). The effect of the ZVAD and Nec-1 combination treatment on RGC survival was even more pronounced when the treatment was given at day 0, day 3 and day 7 after injury when compared to a single treatment at day 0 (p<0.05).

B. A Necrosis Inhibitor in Combination with a Caspase Inhibitor Promotes Axon Regeneration To investigate the efficacy of necrosis inhibitor and pan-caspase inhibitor in promoting axon regeneration, eight-weeks-old mice were subjected to optic nerve crush surgery as previously described. Subsequently, injured mice were divided into five groups of treatment: vehicle group, ZVAD group (300 µM; given at day 0, day 3 and day 7 after injury), Nec-1 group (4 mM; given at day 0, day 3 and day 7 after injury), ZVAD plus Nec-1 group (300 µM and 4 mM, respectively; given once at day 0), and ZVAD plus Nec-1 group (300 µM and 4 mM, respectively; given at day 0, day 3 and day 7 after injury).

Axon regeneration was assessed by obtaining longitudinal sections of the optic nerve and counting the number of axons at pre-specified distances from the injury site. Specifically, mice were sacrificed at 14 days after optic nerve injury and were perfused with saline and 4% paraformaldehyde (PFA). Optic nerves and eyes were dissected and postfixed in PFA.

Nerves were impregnated with 10% and then 30% sucrose, embedded in OCT Tissue Tek Medium (Sakura Finetek), frozen, cut in the longitudinal plane at 14 µm, and mounted on coated slides. Regenerating axons were visualized by staining with a sheep antibody to βIII-tubulin, followed by staining with a fluorescently labeled secondary antibody. Axons were counted manually in at least eight longitudinal sections per case at pre-specified distances from the injury site. The number of regenerating axons at various distances are determined as described previously (Leon et al., (2000) J Neurosci 20:4615-4626). To determine the number of surviving cells, staining with an anti-Brn3a antibody was used.

Figure 12A:
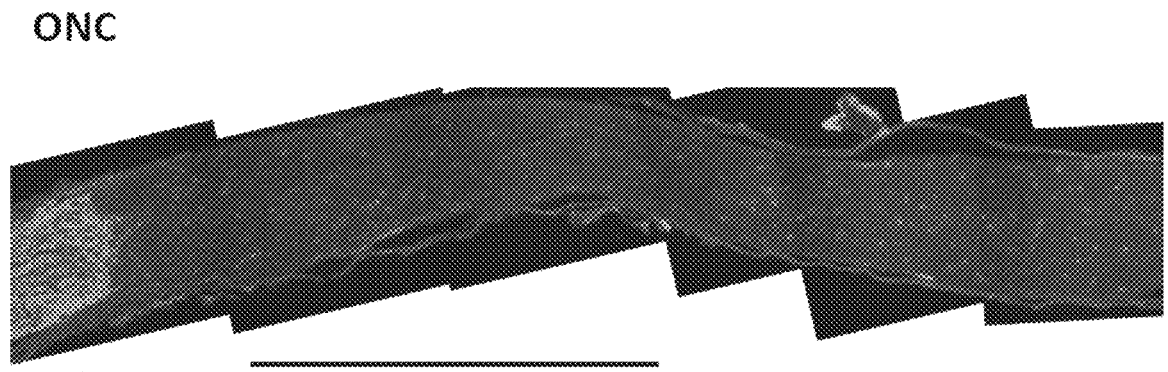
FIGS. 12A-12E provide photographs showing axon regeneration in mice treated with Z-VAD and/or Nec-1 following optic nerve crush injury.
Figure 12B:
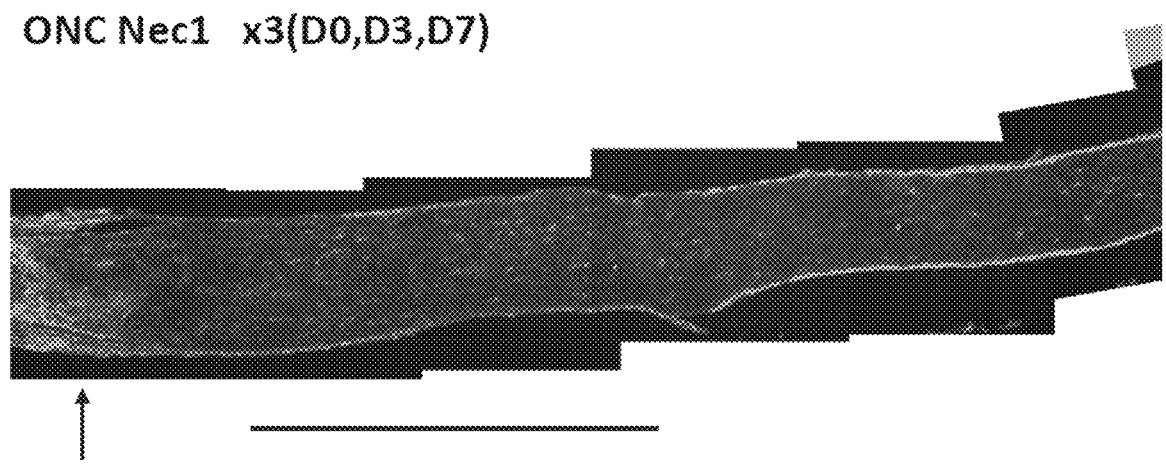
Figure 12C:
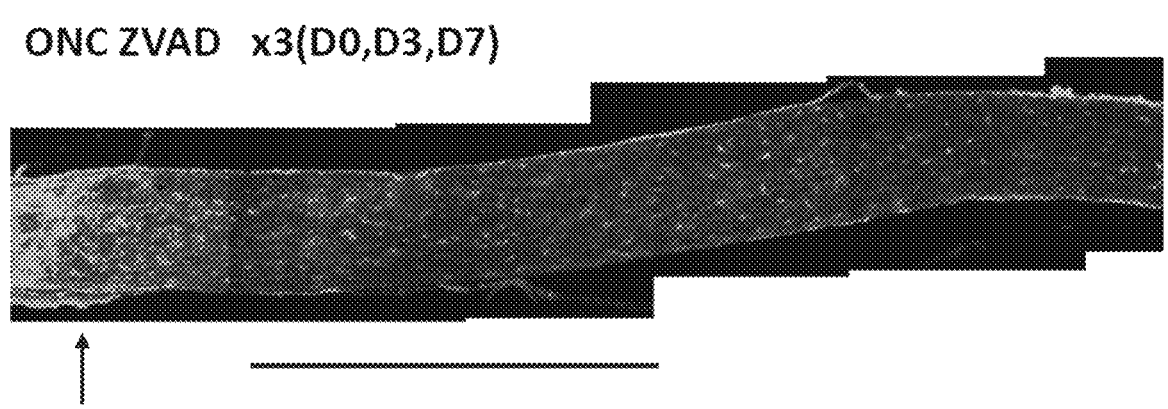
Figure 12D:
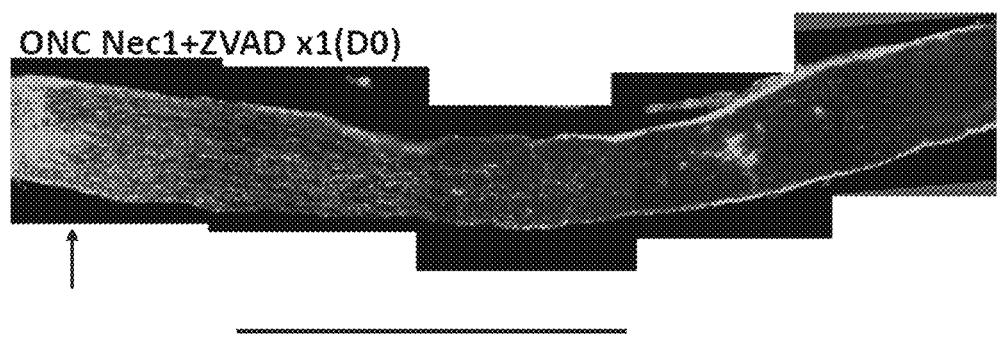
Figure 12E:
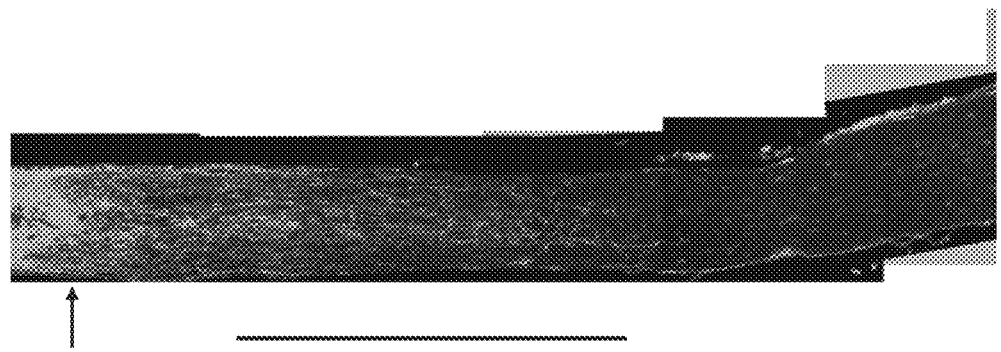

FIGS. 12A-12E show longitudinal sections of the optic nerve following optic nerve crush injury. The sections are stained with an antibody against PIII-tubulin, which marks axon fibers. In each photograph, an arrow indicates the sites of optic nerve injury, and staining beyond the injury site starting from left to right indicates axon regeneration (e.g., axons regenerate from the site of injury into the nerve). No significant axon regeneration was seen in mice treated with vehicle control, as demonstrated by the lack of axon staining (FIG. 12A). Treatment with Nec-1 or ZVAD alone had minimal effects on axon regeneration (FIGS. 12B and 12C). In contrast, ZVAD plus Nec-1 combination treatment significantly enhanced axon outgrowth as demonstrated by the increase in axon staining (FIGS. 12D and 12E; see the regions denoted by the horizontal reference lines under each figure). Further, as shown in FIGS. 12D and 12E, the effect of the ZVAD and Nec-1 combination treatment on axon regeneration was more pronounced when the treatment was given at day 0, day 3 and day 7 after injury when compared to a single treatment at day 0. These results indicate that ZVAD and Nec-1 combination treatment not only ameliorates the loss of RGC following optic nerve injury, but also promotes axon regeneration following injury.

INCORPORATION BY REFERENCE

The entire disclosure of each of the patent documents and scientific articles cited herein are incorporated by reference in their entirety for all purposes.

EQUIVALENTS

The invention can be embodied in other specific forms with departing from the essential characteristics thereof. The foregoing embodiments therefore are to be considered illustrative rather than limiting on the invention described herein. The scope of the invention is indicated by the appended claims rather than by the foregoing description, and all changes that come within the meaning and range of equivalency of the claims are intended to be embraced therein.

We claim:

1. A method of preserving visual function of an eye of a subject with an ocular condition selected from the group consisting of an optic neuropathy and diabetic retinopathy, wherein a symptom of the ocular condition is the loss of retinal ganglion cell viability in the retina of the eye with the condition, the method comprising:
   (a) administering to the eye of the subject an effective amount of a necrosis inhibitor selected from the group consisting of necrostatin-1, necrostatin-2, necrostatin-3, necrostatin-4, necrostatin-5, necrostatin-7, and related compounds, and an effective amount of an apoptosis inhibitor selected from the group consisting of a pan-caspase inhibitor, a caspase-1 inhibitor, a caspase-3 inhibitor, a caspase-8 inhibitor, and a caspase-9 inhibitor, thereby to preserve the viability of a retinal ganglion cell disposed within the retina of the eye; and
   (b) after step (a), measuring visual function of the eye.

2. The method of claim 1, wherein, after administration of the necrosis inhibitor and the apoptosis inhibitor, the visual function of the eye is preserved or improved relative to the visual function prior to administration of the necrosis inhibitor and the apoptosis inhibitor.

3. The method of claim 2, wherein the visual function is visual acuity.

4. The method of claim 1, wherein the ocular condition is an optic neuropathy selected from the group consisting of an ischemic optic neuropathy, compressive optic neuropathy, infiltrative optic neuropathy, traumatic optic neuropathy, a mitochondrial optic neuropathy, nutritional optic neuropathy, toxic optic neuropathy, and a hereditary optic neuropathy.

5. The method of claim 4, wherein the ischemic optic neuropathy is selected from the group consisting of arteritic anterior ischemic neuropathy, non-arteritic anterior ischemic neuropathy, and posterior ischemic optic neuropathy.

6. The method of claim 4, wherein the mitochondrial optic neuropathy is Leber's optic neuropathy.

7. The method of claim 4, wherein the hereditary optic neuropathy is selected from the group consisting of Leber's optic neuropathy, Dominant Optic Atrophy, and Behr's syndrome.

8. The method of claim 1, wherein the ocular condition is diabetic retinopathy.

9. The method of claim 1, wherein the necrosis inhibitor is necrostatin-1.

10. The method of claim 1, wherein the necrosis inhibitor is administered to provide a final concentration of the necrosis inhibitor in the eye greater than about 10 µM.

11. The method of claim 1, wherein from about 0.05 mg to about 2 mg of the necrosis inhibitor is administered.

12. The method of claim 1, wherein the pan-caspase inhibitor is zVAD, IDN-6556, or a combination thereof.

13. The method of claim 1, wherein from about 0.15 mg to about 1.5 mg of the pan-caspase inhibitor is administered.

14. The method of claim 1, wherein the necrosis inhibitor, the apoptosis inhibitor, or both the necrosis inhibitor and the apoptosis inhibitor are administered to the eye.

15. The method of claim 1, wherein the necrosis inhibitor, the apoptosis inhibitor, or both the necrosis inhibitor and the apoptosis inhibitor are administered by intraocular injection.

16. The method of claim 15, wherein the necrosis inhibitor, the apoptosis inhibitor, or both the necrosis inhibitor and the apoptosis inhibitor are administered intravitreally.

17. The method of claim 1, wherein the necrosis inhibitor, the apoptosis inhibitor, or both the necrosis inhibitor and the apoptosis inhibitor are administered sequentially or simultaneously.

18. The method of claim 1, wherein the necrosis inhibitor is a compound of Formula I:

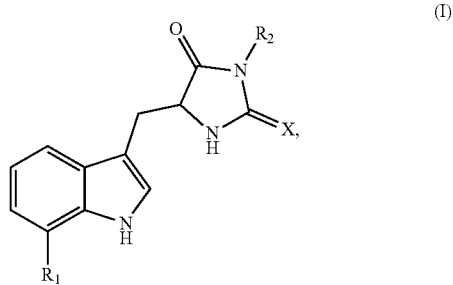

(I)

or a pharmaceutically acceptable salt, an ester, or a prodrug thereof, wherein

X is O or S;

$R_1$ is hydrogen, $C_1$-$C_6$alkyl, $C_1$-$C_6$ alkoxyl, or halogen; and $R_2$ is hydrogen or $C_1$-$C_6$alkyl.

19. The method of claim 1, wherein the necrosis inhibitor is a compound of Formula I-A:

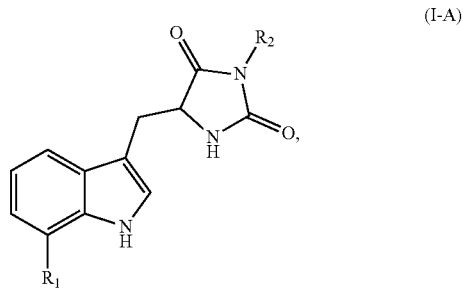

(I-A)

or a pharmaceutically acceptable salt, an ester, or a prodrug thereof, wherein $R_1$ is H, alkyl, alkoxyl, or a halogen; and $R_2$ is H or an alkyl.

20. The method of claim 1, wherein the necrosis inhibitor is a compound selected from the group consisting of a compound of Formula I-B:

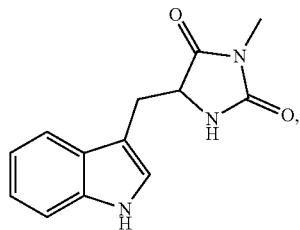
(I-B)

or a pharmaceutically acceptable salt, an ester, or a prodrug thereof;
a compound of Formula I-C:

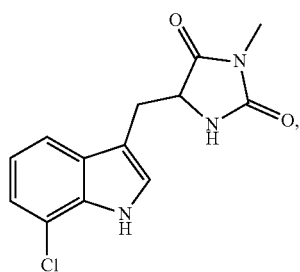
(I-C)

or a pharmaceutically acceptable salt, an ester, or a prodrug thereof; and
a compound of Formula I-D:

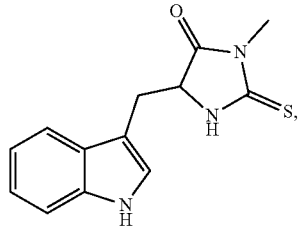
(I-D)

or a pharmaceutically acceptable salt thereof.

21. The method of claim 1, wherein the necrosis inhibitor is a compound of Formula I-E:

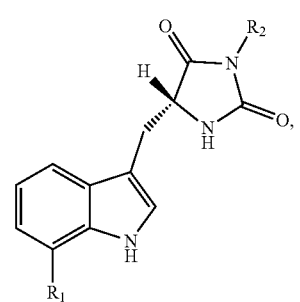
(I-E)

or a pharmaceutically acceptable salt, an ester, or a prodrug thereof,
wherein $R_1$ is H, alkyl, alkoxyl, or a halogen; and $R_2$ is H or an alkyl.

22. The method of claim 1, wherein the necrosis inhibitor is a compound of Formula II:

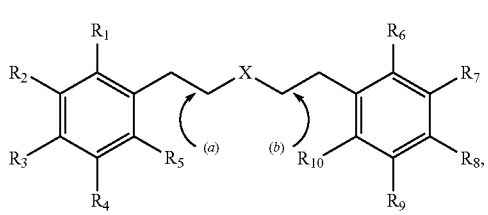
(II)

or a pharmaceutically acceptable salt, an ester, or a prodrug thereof, wherein:

X is —CH$_2$—, —C(H)(R$_{14}$)—, —C(=S)—, —C(=NH)—, or —C(O)—;

$R_1$, $R_2$, $R_3$, $R_4$, $R_5$, $R_6$, $R_7$, $R_8$, $R_9$, and $R_{10}$ each represent independently hydrogen, acyl, acetyl, alkyl, halogen, amino, $C_1$-$C_6$alkoxyl, nitro, —C(O)R$_{12}$, —C(S)R$_{12}$, —C(O)OR$_{12}$, —C(O)NR$_{12}$R$_{13}$, —C(S)NR$_{12}$R$_{13}$, or —S(O$_2$)R$_{12}$;

$R_{11}$ is hydrogen, acyl, acetyl, alkyl, or acylamino;

$R_{12}$ and $R_{13}$ each represent independently hydrogen, an optionally substituted alkyl, an optionally substituted aryl, an optionally substituted heteroaryl, an optionally substituted aralkyl, or an optionally substituted heteroaralkyl;

$R_{14}$ is acyl, acetyl, alkyl, halogen, amino, acylamino, nitro, —SR$_{11}$, —N(R$_{11}$)$_2$, or —OR$_{11}$;

the bond indicated by (a) can be a single bond or a double bond; and the bond indicated by (b) can be a single bond or a double bond.

23. The method of claim 1, wherein the necrosis inhibitor is a compound of Formula II-A:

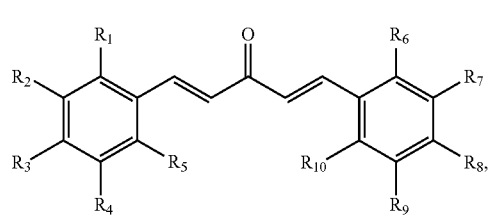
(II-A)

or a pharmaceutically acceptable salt thereof, wherein:

$R_1$, $R_2$, $R_5$, $R_6$, $R_7$, and $R_{10}$ each represent independently hydrogen, alkyl, halogen, amino, or methoxyl; and $R_3$, $R_4$, $R_8$, and $R_9$ are $C_1$-$C_6$alkoxyl.

24. The method of claim 1, wherein the necrosis inhibitor is a compound of Formula III:

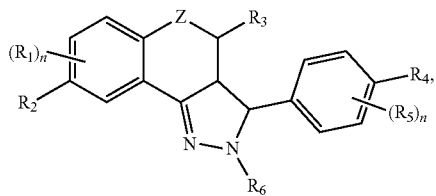
(III)

or a pharmaceutically acceptable salt, an ester, or a prodrug thereof, wherein:

Z is —CH$_2$—, —CH$_2$CH$_2$—, —O—, —S—, —S(O)—, —S(O$_2$)—, or —N(R$_7$)—;

R$_1$, R$_3$, and R$_5$ each represent independently for each occurrence hydrogen, halogen, hydroxyl, amino, C$_1$-C$_6$alkyl, C$_1$-C$_6$alkoxy, C$_1$-C$_6$alkoxy-C$_1$-C$_6$alkyl, C$_1$-C$_6$alkanoyl, C$_1$-C$_6$alkylsulfinyl, C$_1$-C$_6$alkylsulfinyl-C$_1$-C$_6$alkyl, C$_1$-C$_6$alkylsulfonyl, C$_1$-C$_6$alkylsulfonyl-C$_1$-C$_6$alkyl, aryl, aralkyl, heterocycloalkyl, heteroaryl, or heteroaralkyl;

R$_2$ and R$_4$ are C$_1$-C$_6$alkoxy;

R$_6$ is —C(O)R$_8$, —C(S)R$_8$, —C(O)OR$_8$, —C(O)NR$_8$R$_9$, —C(S)NR$_8$R$_9$, —C(NH)R$_8$, or —S(O$_2$)R$_8$;

R$_7$ is alkyl, aralkyl, or heteroaralkyl;

R$_8$ and R$_9$ each represent independently hydrogen, C$_1$-C$_6$alkyl, heteroalkyl, aryl, heteroaryl, aralkyl, or heteroaralkyl; and n represents independently for each occurrence 0, 1, or 2.

25. The method of claim 1, wherein the necrosis inhibitor is a compound of Formula IV:

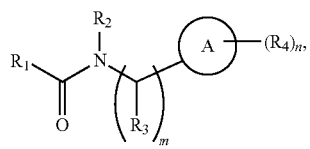
(IV)

or a pharmaceutically acceptable salt, an ester, or a prodrug thereof, wherein:

R$_1$ is

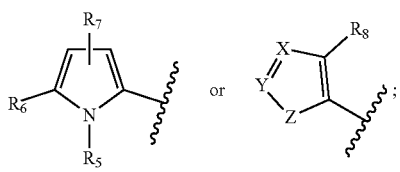

R$_2$ and R$_3$ each represent independently for each occurrence hydrogen or methyl;

R$_4$ represents independently for each occurrence halogen, hydrogen, C$_1$-C$_6$alkyl, C$_2$-C$_6$alkenyl, or C$_2$-C$_4$alkynyl;

R$_5$ is C$_1$-C$_4$alkyl;

R$_6$ is hydrogen, halogen, or —CN;

R$_7$ is hydrogen or C$_1$-C$_4$alkyl;

R$_8$ is C$_1$-C$_6$alkyl, or R$_8$ taken together with R$_9$, when present, forms a carbocyclic ring;

R$_9$ is hydrogen or C$_1$-C$_6$alkyl, or R$_9$ taken together with R$_8$ forms a carbocyclic ring;

R$_{10}$ is hydrogen or C$_1$-C$_6$alkyl;

A is phenylene or a 5-6 membered heteroarylene;

X is N or —C(R$_9$)—;

Y is N or —C(R$_{10}$)—;

Z is S or O; and m and n each represent independently 1, 2, or 3.

26. The method of claim 1, wherein the necrosis inhibitor is a compound of Formula V:

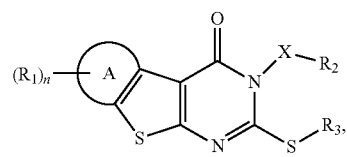
(V)

or a pharmaceutically acceptable salt, an ester, or a prodrug thereof, wherein:

A is a saturated or unsaturated 5-6 membered carbocyclic ring;

X is a bond or C$_1$-C$_4$alkylene;

R$_1$ is C$_1$-C$_6$ alkyl, halogen, hydroxyl, C$_1$-C$_6$alkoxyl, —N(R$_4$)$_2$, —C(O)R$_4$, CO$_2$R$_4$, or C(O)N(R$_4$)$_2$;

R$_2$ is

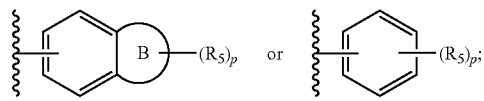

R$_3$ is —C$_1$-C$_6$alkylene-CN, —CN, C$_1$-C$_6$alkyl, or C$_2$-C$_6$alkenyl;

R$_4$ represents independently for each occurrence hydrogen, C$_1$-C$_6$alkyl, aryl, or aralkyl;

R$_5$ represents independently for each occurrence C$_1$-C$_6$alkyl, halogen, hydroxyl, C$_1$-C$_6$alkoxyl, —N(R$_4$)$_2$, —C(O)R$_4$, CO$_2$R$_4$, or C(O)N(R$_4$)$_2$;

B is a 5-6 membered heterocyclic or carbocyclic ring; and n and p each represent independently 0, 1, or 2.

27. The method of claim 1, wherein the necrosis inhibitor is a compound of Formula V-A:

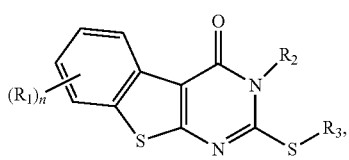
(V-A)

or a pharmaceutically acceptable salt, an ester, or a prodrug thereof, wherein:

R$_1$ is C$_1$-C$_6$alkyl, halogen, hydroxyl, C$_1$-C$_6$alkoxyl, or —N(R$_4$)$_2$;

R$_2$ is

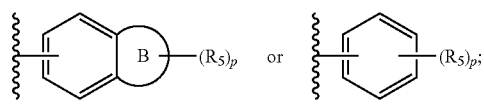

R$_3$ is —C$_1$-C$_6$alkylene-CN;

R$_4$ represents independently for each occurrence hydrogen, C$_1$-C$_6$alkyl, aryl, or aralkyl;

$R_5$ represents independently for each occurrence $C_1$-$C_6$alkyl, halogen, hydroxyl, $C_1$-$C_6$alkoxyl, —N($R_4$)$_2$, —C(O)$R_4$, CO$_2$$R_4$, or C(O)N($R_4$)$_2$;

B is a 5-6 membered heterocyclic or carbocyclic ring; and n and p each represent independently 0, 1, or 2.

28. The method of claim 1, wherein the necrosis inhibitor is a compound of Formula VII:

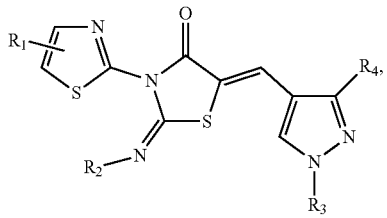

(VII)

or a pharmaceutically acceptable salt, an ester, or a prodrug thereof, wherein:

$R_1$, $R_2$, and $R_3$ each represent independently hydrogen or $C_1$-$C_4$alkyl;

$R_4$ is

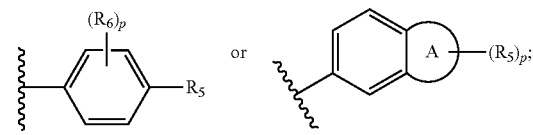

$R_5$ and $R_6$ each represent independently for each occurrence halogen, $C_1$-$C_6$alkyl, hydroxyl, $C_1$-$C_6$alkoxyl, —N($R_7$)$_2$, —NO$_2$, —S—$C_1$-$C_6$alkyl, —S-aryl, —SO$_2$—$C_1$-$C_6$alkyl, —SO$_2$-aryl, —C(O)$R_7$, —CO$_2$$R_7$, —C(O)N($R_7$)$_2$, heterocycloalkyl, aryl, or heteroaryl;

$R_7$ represents independently for each occurrence hydrogen, $C_1$-$C_6$alkyl, aryl, or aralkyl; or two occurrences of $R_7$ attached to the same nitrogen atom are taken together with the nitrogen atom to which they are attached to form a 3-7 membered heterocyclic ring;

A is a 5-6 membered heterocyclic ring; and p is 0, 1, or 2.

29. The method of claim 1, wherein the necrosis inhibitor is a compound of Formula VIII:

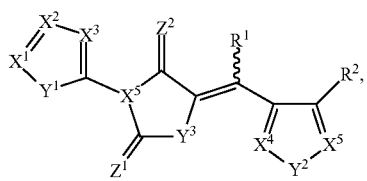

(VIII)

or a pharmaceutically acceptable salt, an ester, or a prodrug thereof, wherein:

each $X^1$, $X^2$, $X^3$, $X^4$, $X^5$, and $X^6$ is selected, independently, from N or CR$^{X1}$;

each $Y^1$, $Y^2$, and $Y^3$ is selected, independently, from O, S, NR$^{Y1}$, or CR$^{Y2}$R$^{Y3}$;

each $Z^1$ and $Z^2$ is selected, independently, from O, S, or NR$^{Z1}$;

each R$^{Y1}$ and R$^{Z1}$ is selected, independently, from H, optionally substituted $C_1$-$C_6$alkyl, optionally substituted $C_2$-$C_6$alkenyl, optionally substituted $C_2$-$C_6$alkynyl, optionally substituted cycloalkyl, optionally substituted heterocyclyl, optionally substituted aryl, optionally substituted heteroaryl, —C(=O)R$^{5A}$, —C(=O)OR$^{5A}$, or —C(=O)NR$^{5A}$R$^{6A}$;

each R$^{X1}$, R$^{Y2}$, and R$^{Y3}$ is selected, independently, from H, halogen, CN, NC, NO$_2$, N$_3$, OR$^3$, SR$^3$, NR$^3$R$^4$, —C(=O)R$^{5A}$, —C(=O)OR$^{5A}$, —C(=O)NR$^{5A}$R$^{6A}$, —S(=o)R$^{5A}$, —S(=O)$_2$R$^{5A}$, —S(=O)$_2$OR$^{5A}$, —S(=O)$_2$NR$^{5A}$R$^{6A}$, optionally substituted $C_1$-$C_6$alkyl, optionally substituted $C_2$-$C_6$alkenyl, optionally substituted $C_2$-$C_6$alkynyl, optionally substituted cycloalkyl, optionally substituted heterocyclyl, optionally substituted aryl, or optionally substituted heteroaryl;

each R$^1$, R$^2$R$^{5A}$, R$^{5B}$, R$^{6A}$, and R$^{6B}$ is selected from H, optionally substituted $C_1$-$C_6$alkyl, optionally substituted $C_2$-$C_6$alkenyl, optionally substituted $C_2$-$C_6$alkynyl, optionally substituted cycloalkyl, optionally substituted heterocyclyl, optionally substituted aryl, or optionally substituted heteroaryl; or R$^{5A}$ and R$^{6A}$, or R$^{5B}$ and R$^{6B}$ combine to form a heterocyclyl; and each R$^3$ and R$^4$ is selected from H, optionally substituted $C_1$-$C_6$alkyl, optionally substituted cycloalkyl, optionally substituted heterocyclyl, optionally substituted aryl, optionally substituted heteroaryl, —C(=O)R$^{5B}$, —C(=S)R$^{5B}$, —C(=NR$^{6B}$)R$^{5B}$, —C(=O)OR$^{5B}$, —C(=O)NR$^{5B}$R$^{6B}$, —S(=O)R$^{5B}$, —S(=O)$_2$R$^{5B}$, —S(=O)$_2$OR$^{5B}$, or —S(=O)$_2$NR$^{5B}$R$^{6B}$.

30. The method of claim 1, wherein the necrosis inhibitor is a compound of Formula IX:

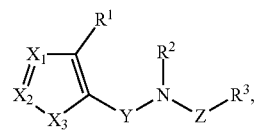

(IX)

or a pharmaceutically acceptable salt, an ester, or a prodrug thereof, wherein:

$X_1$ and $X_2$ are, independently, N or CR$^4$;

$X_3$ is selected from O, S, NR$^5$, or (CR$^5$)$_2$;

Y is selected from C(O) or CH$_2$; and

Z is (CR$^6$R$^7$)$_n$;

R$^1$ is selected from H, halogen, optionally substituted $C_1$-$C_6$alkyl, optionally substituted $C_1$-$C_6$cycloalkyl, or optionally substituted aryl;

R$^2$ is selected from H or optionally substituted $C_1$-$C_6$alkyl;

R$^3$ is optionally substituted aryl;

each R$^4$ is selected from H, halogen, carboxamido, nitro, cyano, optionally substituted $C_1$-$C_6$alkyl, or optionally substituted aryl;

R$^5$ is selected from H, halogen, optionally substituted $C_1$-$C_6$alkyl, or optionally substituted aryl;

each R$^6$ and R$^7$ is, independently, selected from H, optionally substituted $C_1$-$C_6$alkyl, or aryl; and n is 0, 1, 2, or 3.

* * * * *